(12) United States Patent
Sowemimo-Coker et al.

(10) Patent No.: US 11,911,471 B2
(45) Date of Patent: *Feb. 27, 2024

(54) ANAEROBIC BLOOD STORAGE AND PATHOGEN INACTIVATION METHOD

(71) Applicant: Hemanext Inc., Lexington, MA (US)

(72) Inventors: Samuel O. Sowemimo-Coker, Dix Hills, NY (US); Jeffrey Sutton, Medway, MA (US); Tatsuro Yoshida, West Newton, MA (US)

(73) Assignee: Hemanext Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,846

(22) Filed: Sep. 23, 2021

(65) Prior Publication Data

US 2022/0001013 A1  Jan. 6, 2022

Related U.S. Application Data

(62) Division of application No. 16/304,611, filed as application No. PCT/US2017/034410 on May 25, 2017, now Pat. No. 11,147,876.

(60) Provisional application No. 62/445,081, filed on Jan. 11, 2017, provisional application No. 62/342,756, filed on May 27, 2016.

(51) Int. Cl.
   *A61K 41/17* (2020.01)
   *A61K 35/18* (2015.01)
   *A61L 2/00* (2006.01)

(52) U.S. Cl.
   CPC ............ *A61K 41/17* (2020.01); *A61K 35/18* (2013.01); *A61L 2/0047* (2013.01); *A61L 2/0076* (2013.01); *A61L 2/0082* (2013.01); *A61L 2202/22* (2013.01)

(58) Field of Classification Search
   CPC ....... A61K 41/17; A61K 35/18; A61L 2/0047; A61L 2/0076; A61L 2/0082; A61L 2202/22
   See application file for complete search history.

(56) References Cited

U.S. PATENT DOCUMENTS

| | | |
|---|---|---|
| 3,064,647 A | 11/1962 | Earl |
| 3,361,041 A | 1/1968 | Grob |
| 3,489,647 A | 1/1970 | Kolobow |
| 3,668,837 A | 6/1972 | Gross |
| 3,668,838 A | 6/1972 | McNeil et al. |
| 3,803,810 A | 4/1974 | Rosenberg |
| 3,910,841 A | 10/1975 | Esmond |
| 3,942,529 A | 3/1976 | Waage |
| 4,075,091 A | 2/1978 | Bellhouse |
| 4,086,924 A | 5/1978 | Latham, Jr. |
| 4,093,515 A | 6/1978 | Kolobow |
| 4,131,200 A | 12/1978 | Rinfret |
| 4,162,676 A | 7/1979 | Talcott |
| 4,199,062 A | 4/1980 | Johnston et al. |
| 4,222,379 A | 9/1980 | Smith |
| 4,225,439 A | 9/1980 | Spranger |
| 4,228,032 A | 10/1980 | Talcott |
| 4,253,458 A | 3/1981 | Bacehowski et al. |
| 4,256,692 A | 3/1981 | Cover |
| 4,262,581 A | 4/1981 | Ferrell |
| 4,300,559 A | 11/1981 | Gajewski et al. |
| 4,314,480 A | 2/1982 | Becker |
| 4,342,723 A | 8/1982 | Sado et al. |
| 4,366,179 A | 12/1982 | Nawata et al. |
| 4,370,160 A | 1/1983 | Ziemelis |
| 4,381,775 A | 5/1983 | Nose' et al. |
| 4,386,069 A | 5/1983 | Estep |
| 4,398,642 A | 8/1983 | Okudaira et al. |
| 4,440,815 A | 4/1984 | Zomorodi et al. |
| 4,455,299 A | 6/1984 | Grode |
| 4,540,416 A | 9/1985 | Hattori et al. |
| 4,568,328 A | 2/1986 | King et al. |
| 4,572,899 A | 2/1986 | Walker et al. |
| 4,579,223 A | 4/1986 | Otsuka et al. |
| 4,585,735 A | 4/1986 | Meryman et al. |
| 4,609,383 A | 9/1986 | Bonaventura et al. |
| 4,629,544 A | 12/1986 | Bonaventura et al. |
| 4,639,353 A | 1/1987 | Takemura et al. |
| 4,654,053 A | 3/1987 | Sievers et al. |
| 4,659,549 A | 4/1987 | Hamada et al. |
| 4,670,013 A | 6/1987 | Barnes et al. |
| 4,701,267 A | 10/1987 | Watanabe et al. |

(Continued)

FOREIGN PATENT DOCUMENTS

| | | |
|---|---|---|
| AU | 2012279043 | 7/2016 |
| CA | 2477946 | 9/2003 |

(Continued)

OTHER PUBLICATIONS

U.S. Appl. No. 10/295,781, filed Nov. 15, 2002, Bitensky et al.
U.S. Appl. No. 62/131,130, filed Mar. 15, 2015, Wolf et al.
U.S. Appl. No. 62/151,957, filed Apr. 23, 2015, Yoshida et al.
U.S. Appl. No. 12/901,350, filed Oct. 8, 2010, Yoshida et al.
Agarwal et al., "Effect of pre-storage gamma irradiation on red blood cells," *Indian Journal of Medical Research* 122(5):385 (2005).
Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).

(Continued)

*Primary Examiner* — Kade Ariani
(74) *Attorney, Agent, or Firm* — Arnold & Porter Kaye Scholer

(57) ABSTRACT

A method for reducing hemolysis and microparticle formation during storage of pathogen reduced blood. Oxygen reduced blood compositions comprising SAGM and riboflavin having reduced hemolysis. Oxygen reduced blood compositions comprising SAGM and riboflavin having reduced microparticles. Oxygen and pathogen reduced blood compositions comprising CPAD and riboflavin having reduced hemolysis. Oxygen and pathogen reduced blood compositions comprising SAGM and riboflavin having reduced microparticles.

8 Claims, 12 Drawing Sheets

(56) References Cited

U.S. PATENT DOCUMENTS

| | | |
|---|---|---|
| 4,713,176 A | 12/1987 | Schoendorfer et al. |
| 4,731,978 A | 5/1988 | Martensson |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,798,728 A | 1/1989 | Sugisawa |
| 4,828,561 A | 5/1989 | Woodroof |
| 4,837,047 A | 6/1989 | Sato et al. |
| 4,859,360 A | 8/1989 | Suzuki et al. |
| 4,861,867 A | 8/1989 | Estep |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 4,986,837 A | 1/1991 | Shibata |
| 4,998,990 A | 3/1991 | Richter et al. |
| 5,000,848 A | 3/1991 | Hodgins et al. |
| 5,023,054 A | 6/1991 | Sato et al. |
| 5,037,419 A | 8/1991 | Valentine et al. |
| 5,120,659 A | 6/1992 | King et al. |
| 5,137,531 A | 8/1992 | Lee et al. |
| 5,139,668 A | 8/1992 | Pan et al. |
| 5,143,763 A | 9/1992 | Yamada et al. |
| 5,152,905 A | 10/1992 | Pall et al. |
| 5,192,320 A | 3/1993 | Anazawa et al. |
| 5,194,158 A | 3/1993 | Matson |
| 5,208,335 A | 5/1993 | Ramprasad et al. |
| 5,229,012 A | 7/1993 | Pall et al. |
| 5,254,248 A | 10/1993 | Nakamura et al. |
| 5,286,407 A | 2/1994 | Inoue et al. |
| 5,328,268 A | 7/1994 | LaFleur |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,368,808 A | 11/1994 | Koike et al. |
| 5,382,526 A | 1/1995 | Gajewski et al. |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,449,617 A | 9/1995 | Falkenberg et al. |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,686,304 A | 11/1997 | Codner |
| 5,691,452 A | 11/1997 | Gawryl et al. |
| 5,693,122 A | 12/1997 | Bermdt |
| 5,693,230 A | 12/1997 | Asher |
| 5,698,250 A | 12/1997 | DelDuca et al. |
| 5,709,472 A | 1/1998 | Prusik et al. |
| 5,744,056 A | 4/1998 | Venkateshwaran et al. |
| 5,730,989 A | 5/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,928,178 A | 7/1999 | Samolyk |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,068,152 A | 5/2000 | Meiners et al. |
| 6,076,664 A | 6/2000 | Yeager |
| 6,080,322 A | 6/2000 | Deniega et al. |
| 6,090,062 A | 7/2000 | Sood et al. |
| 6,097,293 A | 8/2000 | Galloway et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,287,284 B1 | 9/2001 | Woarburton-Pitt |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,479,252 B1 | 11/2002 | Barbera-Guillem et al. |
| 6,482,585 B2 | 11/2002 | Dottori |
| 6,494,909 B2 | 12/2002 | Greenhalgh |
| 6,527,957 B1 | 3/2003 | Denienga et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |

(56) References Cited

U.S. PATENT DOCUMENTS

| | | |
|---|---|---|
| 8,569,052 B2 | 10/2013 | Federspiel et al. |
| 8,864,735 B2 | 10/2014 | Sano et al. |
| 8,877,508 B2 | 11/2014 | Hyde et al. |
| 8,887,721 B2 | 11/2014 | Zapol et al. |
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 | 10/2017 | Yoshida et al. |
| 9,844,615 B2 | 12/2017 | Yoshida et al. |
| 10,603,417 B2 | 3/2020 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1 | 2/2003 | Ng et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0146671 A1 | 7/2004 | Szabo et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0207186 A1 | 9/2007 | Scanlon et al. |
| 2007/0240569 A1 | 10/2007 | Ooya |
| 2007/0276508 A1 | 11/2007 | Fischer et al. |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2008/0299538 A1 | 12/2008 | Goodrich et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0282662 A1 | 11/2010 | Lee et al. |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004937 A1 | 1/2013 | Yoshida et al. |
| 2013/0144266 A1 | 6/2013 | Borenstein et al. |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |
| 2018/0094269 A1 | 4/2018 | Miller et al. |
| 2019/0275152 A1 | 9/2019 | Sowemimo-Coker et al. |

FOREIGN PATENT DOCUMENTS

| | | |
|---|---|---|
| CN | 1195965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 102711865 A | 10/2012 |
| CN | 103732056 | 4/2014 |
| CN | 109195632 A | 1/2019 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 245 217 A2 | 10/2002 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | S57-3652 A | 1/1982 |
| JP | 58-194879 | 11/1983 |
| JP | 59-115349 | 7/1984 |
| JP | 61-109577 A | 5/1986 |
| JP | 63-63616 A | 3/1988 |
| JP | 01-013860 | 3/1989 |
| JP | 01-104271 A | 4/1989 |
| JP | 3-284263 | 12/1991 |
| JP | 5-503075 A | 5/1993 |
| JP | 5-503304 A | 6/1993 |
| JP | H05-148151 A | 6/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | H 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |

(56) References Cited

FOREIGN PATENT DOCUMENTS

| | | |
|---|---|---|
| JP | 2001-523225 | 11/2001 |
| JP | 2002-087971 | 3/2002 |
| JP | 2002-253936 A | 9/2002 |
| JP | 2002-541941 | 12/2002 |
| JP | 2003-010287 | 1/2003 |
| JP | 2004-089495 A | 3/2004 |
| JP | 2004-244044 | 9/2004 |
| JP | 2005-505552 A | 2/2005 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-518952 | 6/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-535235 | 11/2010 |
| JP | 2010-538735 | 12/2010 |
| JP | 2011 000132 A | 1/2011 |
| JP | 2011-92905 | 5/2011 |
| JP | 2011-516570 A | 5/2011 |
| JP | 2013-500794 | 1/2013 |
| JP | 2013-507226 | 3/2013 |
| JP | 2014-501501 | 1/2014 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/48963 A2 | 9/1999 |
| WO | WO 2000/011946 A2 | 3/2000 |
| WO | WO 2000/0062891 | 10/2000 |
| WO | WO 2003/020325 A2 | 3/2003 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006/050328 A1 | 5/2006 |
| WO | WO 2006/057473 A1 | 6/2006 |
| WO | WO 2006/088455 A1 | 8/2006 |
| WO | WO 2008/063868 | 5/2008 |
| WO | WO 2009/126786 A2 | 10/2009 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/006238 | 1/2014 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |
| WO | WO 2017/205590 A2 | 11/2017 |

OTHER PUBLICATIONS

Apstein et al., "Effect of erythrocyte storage and oxyhemoglobin affinity changes on cardiac function," *Am J. Physiol* 248: H508-15 (1985).

Aydogan et al., "Impaired erythrocytes deformability in $H(2)O(2)$-induced oxidative stress: protective effect of L-carnosine," *Clin Hemorheol Microcirc* 39: 93-8 (2008).

Babic, "In vitro function and phagocytosis of galactosylated platelet concentrates after longterm refrigeration," *Transfusion* 47: 442-51 (2007).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Influence of Rejuvenation on the Rheological Properties of Stored Erythrocytes," *VASA*, 23(4):305-311 (1994).

Becker et al., "Studies of platelet concentrates stored at 22 C nad 4 C," *Transfusion* 13: 61-8 (1973).

Benesch et al., "The effect of organic phosphates from the human erythrocyte on the allosteric properties of hemoglobin," *Biochem Biophys Res Commun* 26: 162-7 (1967).

Bensinger et al., "Prolonged maintenance of 2,3-DPG in liquid blood storage: Use of an internal $CO_2$ trap to stabilize pH," *J. Lab. Clin. Med.*, 89(3):498-503 (1977).

Benson et al., "Accumulation of Pro-Cancer Cytokines in the Plasma Fraction of Stored Packed Red Cells," *J Gastrointest Surg.*, 16:460-468 (2012).

Bersin et al., "Importance of oxygen-haemoglobin binding to oxygen transport in congestive heart failure," *Br Heart J* 70: 443-7 (1993).

Beutler et al., "Storage of red cell concentrates in CPD-A2 for 42 and 49 days," *The Journal of Laboratory and Clinical Medicine*, 102(1):53-62 (1983).

Bordbar et al., "Identified metabolic signature for assessing red blood cell unit quality is associated with endothelial damage markers and clinical outcomes," *Transfusion* 56: 852-62 (2016).

Borenstein et al., "Microfabrication Technology for Vascularized Tissue Engineering," *Biomedical Microdevices*, 4(3):167-175 (2002).

Brody et al., "Deformation and Flow of Red Blood Cells in a Synthetic Lattice: Evidence for an Active Cytoskeleton," *Biophysical Journal*, 68:2224-2232 (1995).

Browne et al., "The molecular pathobiology of cell membrane iron: the sickle red cell as a model" *Free Radic Biol Med* 24: 1040-8 (1998).

Browne et al., "Removal of erythrocyte membrane iron in vivo ameliorates the pathobiology of murine thalassemia," *J Clin Invest* 100: 1459-64 (1997).

Bryant et al., "Pathogen Inactivation the Definitive Safeguard for the Blood Supply," *Arch Pathol Lab Med* 131:719-733 (2007).

Burns et al., "Anaerobic Storage Improves the Mechanical Properties of Stored Red Blood Cells," *Transfusion* 52: 83A (2012).

Burns et al., "Artificial microvascular network: a new tool for measuring rheologic properties of stored red blood cells," *Transfusion*, 52(5):1010-1023 (2012).

(56) References Cited

OTHER PUBLICATIONS

Burns et al., "Deterioration of red blood cell mechanical properties is reduced in anaerobic storage," *Blood Transfus* 14: 80-8 (2016).
Buskirk et al., "Accumulation of Biologic Response Modifiers During Red Blood Cell Cold Storage," *Transfusion*, 49(Suppl3): 102A-103A (2009).
Cabrales et al., "Microvascular pressure and functional capillary density in extreme hemodilution with low-and high-viscosity dextran and a low-viscosity Hb-based 02 carrier," *American Journal of Physiology-Heart and Circulatory Physiology* 287: H363-H73 (2004).
Cabrales et al., "Plasma viscosity regulates systemic and microvascular perfusion during acute extreme anemic conditions," *Am J. Physiol Heart Circ Physiol* 291: H2445-52 (2006).
Cannon et al., "Damage control resuscitation in patients with severe traumatic hemorrhage: A practice management guideline from the Eastern.Association for the Surgery of Trauma," *J Trauma Acute Care Surg* 82: 605-17 (2017).
Cap et al., "Whole Blood Transfusion," *Military Medicine* 183, 9/10:44 (2018).
Cardo et al., "Pathogen inactivation of *Leishmania donovani infantum* in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Carmen, "The Selection of Plastic Materials for Blood Bags," *Transfusion Medicine Reviews*, 7(1): 1-10 (1993).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on December 11, 2012, from: http://www.rheoscan.com/products/products/products-01.html.
Chanutin et al., "Effect of organic and inorganic phosphates on the oxygen equilibrium of human erythrocytes," *Arch Biochem Biophys* 121: 96-102 (1967).
Chaplin et al., "The Proper Use of Previously Frozen Blood Cells for Transfusion," *Blood*, 59:1118-1120 (1982).
Chatpun et al., "Cardiac mechanoenergetic cost of elevated plasma viscosity after moderate hemodilution," *Biorheology* 47: 225-37 (2010).
Chatpun et al., "Cardiac systolic function recovery after hemorrhage determines survivability during shock," *J Trauma* 70: 787-93 (2011).
Chatpun et al., "Effects of plasma viscosity modulation on cardiac function during moderate hemodilution," *Asian J Transfus* Sci 4: 102-8 (2010).
Chilton et al., "Privacy Protection of Health Information: Patient Rights and Pediatrician Responsibilities," *Pediatrics*, 104(4):973-977 (1999).
Choi et al., "Influence of storage temperature on the responsiveness of human platelets to agonists," *Ann Clin Lab Sci* 33: 79-85 (2003).
Chouchani et al., "Ischaemic accumulation of succinate controls reperfusion inquy through mitochondrial ROS," *Nature* 515: 431-5 (2014).
Coene, "Paired analysis of plasma proteins and coagulant capacity after treatment with three methods of pathogen reduction," *Transfusion* 54: 1321-31 (2014).
Cognasse et al., "The role of microparticles in inflammation and transfusion: A concise review," *Transfus. Apher. Sci.* 53(2):159-167 (2015).
Cokelet et al., "Fabrication of in Vitro Microvascular Blood Flow Systems by Photolithography," *Microvascular Research*, 46:394-400 (1993).
Corbin, "Pathogen Inactivation of Blood Components: Current Status and Introduction of an Approach Using Riboflavin as a Photosensitizer," *International Journal of Hematology Supplement* 11 76:253-257 (2002).
Cotton et al., "A Randomized Controlled Pilot Trial of Modified Whole Blood Versus Component Therapy in Severely Injured Patients Requiring Large Volume Transfusions," *Annals of Surgery* 258(4) (2013).

Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
D'Alessandro et al., "Heterogeneity of blood processing and storage additives in different centers impacts stored red blood cell metabolism as much as storage time: lessons from REDS-11I-Omics," *Transfusion* 59: 89-100 (2019).
D'Alessandro et al., "Time-course investigation of SAGM-stored leukocyte-filtered red bood cell concentrates: from metabolism to proteomics," *Haematologica* 97: 107-15 (2012).
D'Alessandro et al., "Red blood cell metabolism under prolonged anaerobic storage," *Mol Biosyst* 9: 1196-209 (2013).
D'Alessandro et al., "Red blood cell metabolic responses to refrigerated storage, rejuvenation, and frozen storage," *Transfusion* 57: 1019-30 (2017).
D'Alessandro et al., "Metabolomics of AS-5 RBC supernatants following routine storage," *Vox Sang* (2014).
D'Alessandro et al., "An update on red blood cell storage lesions, as gleaned through biochemistry and omics technologies," *Transfusion* 55: 205-19 (2015).
D'Alessandro et al., "Red blood cell storage and clinical outcomes: new insights," *Blood Transfus* 15: 101-3 (2017).
D'Alessandro et al., "Plasma succinate is a predictor of mortality in critically injured patients," *Journal of Trauma and Acute Care Surgery* 83: 491-5 (2017).
D'Alessandro et al., "Plasma First Resuscitation Reduces Lactate Acidosis, Enhances Redox Homeostasis, Amino Acid and Purine Catabolism in a Rat Model of Profound Hemorrhagic Shock," *Shock* 46: 173-82 (2016).
D'Alessandro et al., "Anaerobic storage Condition enhances GSH Levels while Maintaining Pentose Phosphate Pathway Activity," *Transfusion* 56: 51A (2016).
D'Alessandro et al., "Red blood cell storage in additive solution-7 preserves energy and redox metabolism: a metabolomies approach," *Transfusion* 55: 2955-66 (2015).
D'Alessandro et al., "Routine storage of red blood cell (RBC) units in additive solution-3: a comprehensive investigation of the RBC metabolome," *Transfusion* 55: 1155-68 (2015).
D'Alessandro et al., "Omics markers of the red cell storage lesion and metabolic linkage," *Blood Transfus* 15: 137-44 (2017).
D'Alessandro et al., "AltitudeOmics: Red Blood Cell Metabolic Adaptation to High Altitude Hypoxia," *J Proteome Res* 15: 3883-95 (2016).
D'Alessandro et al., "Citrate metabolism in red blood cells stored in additive solution-3," *Transfusion* 57: 325-36 (2017).
D'Alessandro et al., "Metabolic effect of alkaline additives and guanosine/glueonate in storage solutions for red blood cells," *Transfusion* 58: 1992-2002 (2018).
D'Alessandro et al., "Effects of aged stored autologous red blood cells on human plasma metabolome," *Blood Adv* 3: 884-96 (2019).
D'Alessandro et al., "Hitchhiker's guide to the red cell storage galaxy: Omics technologies and the quality issue," *Transfus Apher Sci* 56: 248-53 (2017).
D'Amici, et al., "Red blood cell storage in SAGM and AS3: a comparison through the membrane two-dimensional electrophoresis proteome," *Blood Transfusion = Trasfusione del sangue* 10 Suppl 2: s46-54 (2012).
De Angelis et al., "Erythrocyte Shape Control in Stored Blood: The Effect of Additive Solutions on Shape Recovery,"*Haematologica*, 73:7-12 (1988).
Deible et al., "Molecular barriers to biomaterial thrombosis by modification of surface proteins with polyethylene glycol," *Biomaterials*, 19:1885-1893 (1998).
De Korte et al., "Prolonged maintenance of 2,3-diphosphoglycerate acid and adenosine triphosphate in red blood cells during storage," *Transfusion*, 48:1081-1089 (2008).
De Venuto et al., "Rejuvenation of Human Red Blood Cells During Liquid Storage," *Transfusion*, 14(4):338-344 (1974).
Delgado et al., "Platelet Function in Stored Whole Blood Measured by a Shear- and Von Willebrand Factor-Dependent Methodology is Retained During Storage at 4° C. for up to 7 Days," *Transfusion* 51: 65A (2011).

(56) References Cited

OTHER PUBLICATIONS

Dennis et al., "Transfusion of 2,3 DPG-enriched red blood cells to improve cardiac function," *Ann Thorac Surg* 26: 17-6 (1978).
Dennis et al., "Improved myocardial performance following high 2-3 diphosphoglycerate red cell transfusions," *Surgery* 77: 741-7 (1975).
De Wolski et al., "Metabolic pathways that correlate with post-Transfusion circulation of stored murine red blood cells," *Haematologica* 101: 578-86 (2016).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phoisphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in viva recovery," *Transfusion*, 49(3):458-464 (2009).
Dumont et al., "Performance of Anaerobic Stored Red Blood Cells Prepared Using a Prototype 02 & CO2 Depletion and Storage System," *Transfusion* 51s: SP89 (2011).
Dumont et al., "Randomized cross-over in vitro and in vivo evaluation of a prototype anaerobic conditioning and storage system vs. standard aerobic storage," *Vox Sang* 103: 123 (2012).
Dumont et al., "$CO_2$-dependent metabolic modulation in red cells stored under anaerobic conditions," *Transfusion* 56(2): 392-403 (2016)(epub 2015).
Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
Erickson et al., "Evaluation of in vitro Quality of Stored RBC after Treatment with S303 Pathogen Inactivation at Varying Hematocrits," *Transfusion DUP—General Collection* 48(2) Supplement (2008).
European Search Report completed on Feb. 11, 2005, in European Patent Application No. 02 78 2307.9.
European Search Report Jun. 18, 2019, in European Patent Application No. 19163305.6.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Extended European Search Report dated Oct. 9, 2018, in European Patent Application No. 16784043.8.
Extended European Search Report dated Apr. 16, 2019, in European Patent Application No. 16845192.0.
Extended European Search Report dated Jun. 5, 2019, in European Patent Application No. 19158815.1.
Ezuki et al., "Survival and recoery of apheresis platelets stored in a polyolefin container with high oxygen permeability," *Vox Sanguinis* 94:292-298 (2008).
Fahraeus et al., "The Viscosity of the Blood in Narrow Capillary Tubes," *Am. J. Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities in Vitro and in Vivo by the Human Anti-Lipid a Monoclonal Antibody SdJS-1.17.15," *Infection and Immunity*, 61(9):3873-3878 (1993).
Farber et al., "Effect of decreased 02 affinity of hemoglobin on work performance during exercise in healthy humans," *J Lab Clin Med* 104: 166-75 (1984).
Fast et al., "Inactivation of Human White Blood Cells in Red Blood Cell Products Using the MIRASOL® System for Whole Blood," *Blood* Abstract #2897 110(11)(pt. 1) (2007).
Fatouros et al., "Recombinant factor VII SQ—influence of oxygen, metal ions, pH and ionic strength on its stability in aqueous solution," *International Journal of Pharmaceutics*, 155(1):121-131 (1997).
Feys, "Oxygen removal during pathogen inactivation with riboflavin and UV light preserves protein function in plasma for Transfusion," *Vox Sang* 106: 307-15 (2013).
Frame et al., "A System for Culture of Endothelial Cells in 20-50-μm Branching Tubes," *Microcirculation*, 2(4):377-385 (1995).
"Friction Factor for Flow in Coils and Curved Pipe," Neutrium Available on the world wide web at neutrium.net/fluid_flow/friction-factor-for-flow-in-coils-and-curved-pipe/ (2017).
Friesenecker et al., "Arteriolar vasoconstrictive response: compelling the effects of arginine vasopressin and norepinephrine," *Crit Care* 10: R75 (2006).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gardner, "Problems of Multiple Transfusions," *Official Journal of the California Medical Associate*, 83(2):93-97 (1958).
Gehrke et al., "Metabolomics evaluation of early-storage red blood cell rejuvenation at 4 degrees C and 37 degrees C," *Transfusion* 58: 1980-91 (2018).
Gevi et al., "Alterations of red blood cell metabolome during cold liquid storage of erythrocyte concentrates in CPD-SAGM," *J Proteomics* 76 Spec No. 168-180 (2012).
Gifford et al, "Parallel Microchannel-Based Measurements of Individual Erythrocyte Areas and Volumes," *Biophysical Journal*, 84:623-633 (2003).
Gifford et al, "A detailed study of time-dependent changes in human red blood cells: from reticulocyte maturation to erythrocyte senescence," *British Journal of Haematology*, 135:395-404 (2006).
Golan et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 1990.
Goodrich, "The Use of Riboflavin for the Inactivation of Pathogens in Blood Products," *Vox Sanguinis* Suppl. 2 78:211-215 (2000).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Haddaway et al., "Hemostatie properties of cold-stored whole blood leukoreduced using a platelet-sparing versus a non-platelet-sparing filter," *Transfusion* (2019).

(56) References Cited

OTHER PUBLICATIONS

Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-l red blood cells," *Br J. Haematol*, 57(3):467-478 (1984).
Hebbel, et al., Oxidation-induced changes in microrheologic properties of the red blood cell membrane. *Blood* 1990;76: 1015-20.
Hebbel, "Auto-oxidation and a membrane-associated 'Fenton reagent': a possible explanation for development of membrane lesions in sickle erythroeytes," *Clin Haematol* 14: 129-40 (1985).
Henschler et al., "Development of the S-303 Pathogen Inactivation Technology for Red Blood Cell Concentrates," *Transfusion Medicine and Hemotherapy* 38(1):33-42 (2011).
Hershko, "Mechanism of iron toxicity and its possible role in red cell membrane damage," *Semin Hematol* 26: 277-85 (1989).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hess et al., "Advances in military, field, and austere Transfusion medicine in the last decade," *Transfus Apher Sci* 49: 380-6 (2013).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C.," *Vox Sang*, 51:27-34 (1986).
Högman et al., "Effects of oxygen and mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Hornsey et al., "Cold storage of pooled, buffy-coat-derived, leucoreduced platelets in plasma," *Vox Sang* 95 26-32 (2008).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/U2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (dated Nov. 26, 2012).
International Search Report for PCT/US2016/021794 dated Jul. 18, 2016.
International Search Report for PCT/US2016/033151 dated Oct. 13, 2016.
International Search Report for PCT/US2016/051115 dated Nov. 21, 2016.
International Search Report for PCT/US2017/034410 dated Dec. 22, 2017.
International Search Report for PCT/US2020/057754 dated Feb. 15, 2021.
Irseh et al., "Pathogen inactivation of platelet and plasma blood components for transfusion using the Intercept Blood SystemTM," *Transfusion Medicine and Hemotherapy*, 38:19-31 (2011).
Jagannathan et al., "Oxidative stress under ambient and physiological oxygen tension in tissue culture," *Curr Pharmacol Rep* 2: 64-72 (2016).
Jain et al., "Determinants of Leukocyte Margination in Rectangular Microchannels," *PLoS One*, 4(9):1-8 (2009).
Janetzko et al., "Pathogen reduction technology (Mirasol®) treated singledonor platelets resuspended in a mixture of autologous plasma and PAS," *Vox Sanguinis* 97:234-239 (2009).
Jarman et al., "Rural risk: Geographic disparities in trauma mortality," *Surgery* 160: 1551-9 (2016).
Jarolim et al., "Effect of hemoglobin oxidation products on the stability of red cell membrane skeletons and the associations of skeletal proteins: correlation with a release of them in," *Blood* 76: 2125-31 (1990).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jenkins et al., "Trauma hemostasis and oxygenation research position paper on remote damage control resuscitation: definitions, current practice, and knowledge gaps," *Shock* 41 Suppl 1: 3-12 (2014).
Jesch et al., "Oxygen dissociation after Transfusion of blood stored in ACD or CPD solution," *J Thorac Cardiovasc Surg* 70: 35-9 (1975).
Jiang et al., "Microfluidic synthesis of monodisperse PDMS mierobeads as discrete oxygen sensors," *Soft Matter*, 8:923-926 (2011).
Jo et al., "Surface modification using silanated poly(ethylene glycol)s," *Biomaterials*, 21:605-616 (2000).
Jobes et al., "Toward a definition of "fresh" whole blood: an in vitro characterization of coagulation properties in refrigerated whole blood for Transfusion," *Transfusion* 51: 43-51 (2011).
Johnson et al., "Regulation of blood flow in single capillaries," *American Journal of Physiology*, 212:1405-1415 (1967).

(56) References Cited

OTHER PUBLICATIONS

Jy et al., "Release of Microparticles During Blood Storage Is Influenced by Residual Platelets, Leukocytes and Oxygen Levels," *Blood* 120: 3435 (2012).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kerger et al., "Systemic and subcutaneous microvascular pO2 dissociation during 4-h hemorrhagic shock in conscious hamsters," *Am J. Physiol* 270: H827-H36 (1996).
Khorana et al., "Blood Transfusions, thrombosis, and mortality in hospitalized patients with cancer," *Arch Intern Med* 168: 2377-81 (2008).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Kohli et al., "Packed red cells versus whole blood transfusion for severe paediatric anaemia, pregnancy-related anaemia and obstetric bleeding: an analysis of clinical proactice buidelines from sub-Saharan Africa and evidence underpinning recommendments," *Tropical Medicine and International Health* 24(1):11-22 (2019).
Korsten et al., "Determination of %502 in More Than 1300 Fresh Erythrocyte Concentrates by Resonance Raman Spectroscopy," *Transfusion* 58: 215A (2018).
Kotwal et al., "The Effect of a Golden Hour Policy on the Morbidity and Mortality of Combat Casualties," *JAMA Surg* 151: 15-24 (2016).
Kreuger et al., "A clinical evaluation of citrate-phosphate-dextrose-adenine blood," *Vox Sang* 29: 81-9 (1975).
Krogh, "Studies on the physiology of capillaiies. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthaloeyanine/porous glass composite membrane for oxygen separation," *Journal of Membrane Science*, 286(1-2):12-14 (2006).
Kwan et al., "Microfluidic analysis of cellular deformability of normal and oxidatively damaged redd blood cells," *Am J Hematol* 88: 682-9 (2013).
Kynar Flex Product Catalog, downloaded May 20, 2015 from Kynar.com.
Liu et al., "Beneficial Role of Erythrocyte Adenosine A2B Receptor-Mediated AMP-Activated Protein Kinase Activation in High-Altitude Hypoxia," *Circulation* 134: 405-21 (2016).
Lowndes, "Blood Interference in fluorescence spectrum: Experiment, analysis and comparison with intraoperative measurements on brain tumor," *Bachelor Thesis*, Linköping University, pp. 1-42 (2010).
Lozono et al., "Pathogen inactivation: coming of age," *Curr Opin Hematol* 20(6):540-545 (2013).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Lundblad, "Factor VIII—Reducing agents, copper ions, and stability," http://lundbladbiotech.com.
Manno et al., "Comparison of the hemostatic effects of fresh whole blood, stored whole blood, and components after open heart surgery in children," *Blood* 77: 930-6 (1991).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C.," *Transfusion*, 26(6):500-505 (1986).
Meryman et al., "Extending the storage of red cells at 4° C.," *Transfus. Sci.*, 15(2):105-115 (1994).
Miller, "New evidence in trauma resuscitation-is 1: 1: 1 the answer?" *Perioperative medicine* 2: 13 (2013).
Moll et al., "Dean vortices applied to membrane process. Part 11: Numerical approach," *Journal of Membrane Science*, 288:321-335 (2007).
Mollison, "The Introduction of Citrate as an Anticoagulant for Transfusion and of Glucose as a Red Cell Preservative," *British Journal of Haematology* 108:1318 (2000).
Moroff et al., "Factors Influencing Changes in pH during Storage of Platelet Concentrates at 20-24° C.," *Vox Sanguinis*, 42(1):33-45 (1982).
Moroff et al., "Proposed standardization of methods for determining the 24-hour survival of stored red cells," *Transfusion*, 24:109-114 (1984).
Moroff et al., "Concepts about current conditions for the preparation and storage of platelets," *Transfus Med Rev* V(1):48-59 (1991).
Mufti, "Treatment of whole blood (WB) and red blood cells (RBC) with S-303 inactivates pathogens and retains in vitro quality of stored RBC," *Biologicals* 38:14-19 (2010).
Murphy et al., "Platelet storage at 22° C.: role of gas transport across plastic containers in maintenance of viability," *Blood* 46(2):209-218 (1975).
Murphy et al., "Increased Mortality, Postoperative Morbidity, and Cost After Red Blood Cell Transfusion in Patients Having Cardiac Surgery," *Circulation*, 116:2544-2552 (2007).
Musante et al., "Active Focal Segmental Glomeruloselerosis is Associated with Massive Oxidation of Plasma Albumin," *Journal of the American Society of Nephrology*, 18(3):799-810 (2007).
Mussano et al., "Cytokine, chemokine and growth factor profile of Platelet Rich Plasma," *Universita Degli Studi Di Tornio* 2016.
Nair et al., "Cold-Stored Platelets in PAS Exhibit Superior Hemostatic Potential" *Blood* 126: 772 (2015) Abstract.
Nemkov et al., "Metabolomics in Transfusion medicine," *Transfusion* 56: 980-93 (2015).
Nemkov et al., "Hypoxia modulates the purine salvage pathway and decreases red blood cell and supernatant levels of hypoxanthine during refrigerated storage," *Haematologica* 103: 361-72 (2018).
Nemkov et al., "Metabolism of Citrate and Other Carboxylic Acids in Erythrocytes as a Function of Oxygen Saturation and Refrigerated Storage," *FrontMed* (Lausanne) 4: 175 (2017).
Nessen et al., "Fresh whole blood use by forward surgical teams in Afghanistan is associated with improved survival compared to component therapy without platelets," *Transfusion* 53:107S-113S (2013).
Ng et al., "Components for integrated poly(dimethylsiloxane) microfluidic systems," *Electrophoresis*, 23:3461-3473 (2002).
Nilsson et al., "Association between venous thromboembolism and perioperative allogeneic Transfusion," *Arch Surg* 142: 126-32; discussion 33 (2007).
Ohkuma et al., "The preservative-exchange method using a sextuple-bag system for a 10-week storage period of red blood cells," *Transfusion Medicine*, 1:257-262 (1991).
Paglia et al., "Biomarkers defining the metabolic age of red blood cells during cold storage," *Blood* 128: e43-50 (2016).
Paillous et al. "Mechanisms of photosensitized DNA cleavage," *J. Photochem. Photobiol. B: Biol.* 20:203-209 (1993).
Pallotta et al., "Storing red blood cells with vitamin C and N-acetylcysteine prevents oxidative stress-related lesions: a metabolomics overview," *Blood Transfus* 12: 376-87 (2014).

(56) References Cited

OTHER PUBLICATIONS

Pallotta et al., "Supplementation of anti-oxidants in leucofiltered erythrocyte concentrates: assessment of morphological changes through scanning electron microscopy," *Blood Transfus* 12: 421-4 (2014).
Parkkinen et al., "Plasma ascorbate protects coagulation factors against photooxidation," *Thromb Haemost* 75(2):292-297 (1996).
Peirce et al., "The Membrane Lung: Studies with a New High Permeability Co-Polymer Membrane," *Trans. Amer. Soc. Artif. Int. Organs* vol. XIV:220-226 (1968).
Pelletier et al., "Pathogen inactivation techniques," *Best Practice & Research Clinical Haematology* 19(1):205-242 (2006).
Picker et al., "Current methods for the reduction of blood-borne pathogens: a comprehensive literature review," *Blood Transfusion* 11:343-348 (2013).
Pidcoke et al., "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Poxton, "Antibodies to lipopolysacchacharide," *Journal of Immunological Methods*, 186:1-15 (1995).
Prefiltration before membrane filtration, hydrophobic, 25 µm 142 mm, retrieved on Aug. 26, 2014, from: www.emdmillipore.com/US/en/product/Prefiltration-before-membrane-filtration.
Pries et al., "Biophysical aspects of blood flow in the microvasculature," *Cardiovascular Research*, 32:654-667 (1996).
Prowse et al., "Commercially available blood storage containers," *Vox Sanguinis* 106(1): 1-13 (2014).
Prudent, et al., "Oxygen in Red Blood Cell Concentrates Influence of Donor's Characteristics, Location and Blood Processing," *Vox Sang* 113: 116 (2018).
Przepiorka et al. "Use of Irradiated Blood components: Practice Parameter," *Am J Clin Pathol* 106(1):6-11 (1996).
Ramstack et al., "Shear-induced activation of platelets," *J. Biomech.*, 12:113-125 (1979).
Reisz et al., "Red blood cells in hemorrhagic shock: a critical role for glutaminolysis in fueling alanine transamination in rats," *Blood Advances* 1:1296-305 (2017).
Reisz et al., "Methylation of protein aspartates and deamidated asparagines as a function of blood bank storage and oxidative stress in human red blood cells," *Transfusion* 58: 2978-91 (2018).
Reisz et al., "Metabolic Linkage and Correlations to Storage Capacity in Erythrocytes from Glucose 6-Phosphate Dehydrogenase-Deficient Donors," *FrontMed* (Lausanne) 4: 248 (2017).
Reisz et al., "Oxidative modifications of glyceraldehyde 3-phosphate dehydrogenase regulate metabolic reprogramming of stored red blood cells," *Blood* 128: e32-42 (2016).
Reynolds et al., "S-nitrosohemoglobin deficiency: A mechanism for loss of physiological activity in banked blood," *Proceedings of the National Academy of Sciences*, 104(43):17058-17062 (2007).
Risbano et al., "Effects of Aged Stored Autologous Red Blood Cells on Human Endothelial Function," *Am J Respir Crit Care Med* 192: 1223-33 (2015).
Rock et al., "Nutricel as an additive solution for neonatal transfusion," *Transfusion Science*, 20:29-36 (1999).
Rolfsson et al., "Metabolomics comparison of red cells stored in four additive solutions reveals differences in citrate anticoagulant permeability and metabolism," *Vox Sang* (2017).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Scott et al., "Effect of excess alpha-hemoglobin chains on cellular and membrane oxidation in model beta-thalassemic erythrocytes," *J Clin Invest* 91: 1706-12 (1993).
Seghatehian et al., "Pathogen-reduction systems for blood components: The current position and future trends," *Transfusion and Apheresis Science* 35:189-196 (2006).
Seghatchian, "Pathogen inactivation of whole blood and red cell components: An overview of concept, design, developments, criteria of acceptability and storage lesion," *Transfusion and Apheresis Science* 49:357-363 (2013).
Seok et al., "Genomic responses in mouse models poorly mimic human inflammatory diseases," *Proceedings of the National Academy of Sciences* 110:3507-12 (2013).
Sivertsen et al., "Preparation of leukoreduced whole blood for Transfusion in austere environments; effects of forced filtration, storage agitation, and high temperatures on hemostatic function," *J Trauma Acute Care Surg* 84: S93-S103 (2018).
Shalev et al., "Extremely high avidity association of Fe(III) with the sickle red cell membrane," *Blood* 88: 349-52 (1996).
Shapiro, "To filter blood or universal leukoreduction: what is the answer?," *Critical Care* 8(Suppl 2): S27-draftS30 (2004).
Sheffield et al., "Changes in coagulation factor activity and content of di(2-ethylhexyl) phthate in frozen plasma units during refrigerated storage for up to 5 days after thawing," *Transfusion,* 52:494-502 (2012).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Snyder et al., "In vitro and in vivo evaluation of a whole blood platelet-sparing leukoreduction filtration system," *Transfusion* 50: 2145-51 (2010).
Sohmer et al., "Phosphoenolypyruvate (PEP) Effects on Fresh and Stored Red Blood Cells," *Proceedings of the Society for Experimental Biology and Medicine*, 171:24-33 (1982).
Spinella et al., "Prehospital hemostatic resuscitation to achieve zero preventable deaths after traumatic injury," *Curr Opin Hematol* (2017).
Spinella et al., "Whole blood: back to the future," *Curr Opin Hematol* 23: 536-42 (2016).
Spinella et al., "Whole blood for hemostatic resuscitation of major bleeding," *Transfusion* 56:S190-S202 (2016).
Steurer et al., "Trauma and Massive Blood Transfusions," *Curr. Anesthesial. Rep* 4:200-208 (2014).
Strandenes et al., "Emergency Whole-Blood Use in the Field: a Simplified Protocol for Collection and Transfusion," *Shock* 41(Suppl 1):76-83 (2014).
Strandenes et al., "Low Titer Group O Whole Blood in Emergency Situations," *SCHOCK* 41(Suppl 1): 70-75 (2014).
Su et al., "Impermeable barrier films and protective coatings based on reduced graphene oxide," *Nature Communications* 5 Article No. 4843 (2014).
Sun et al., "Purinergic control of red blood cell metabolism: novel strategies to improve red cell storage quality," *Blood Transfus* 15: 535-42 (2017).
Sun, et al., "Sphingosine-1-phosphate promotes erythrocyte glycolysis and oxygen release for adaptation to high-altitude hypoxia," *Nat Commun* 7: 12086 (2016).
Supplementary European Search Report dated Jan. 20, 2015 in European Patent Application No. 12822378.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:1272-281 (1997).
Szymanski et al., "Effect of rejuvenation and frozen storage on 42-day-old AS-1 RBCs," *Transfusion*, 41:550-555 (2001).
Tannahill et al., "Succinate is an inflammatory signal that induces IL-1beta through HIF-1alpha" *Nature* 496: 238-42 (2013).

(56) References Cited

OTHER PUBLICATIONS

Teisseire et al., "Induced low P50 in anesthetized rats: blood gas, circulatory and metabolic adjustments," *Respir Physiol* 58: 335-44 (1984).
Tinmouth et al., "The Clinical Consequences of the Red Cell Storage Lesion," *Transfusion Medicine Reviews*, 15(2):91-107 (2001).
Tolinski, "Getting the Most out of Polypropylene, Polythylene and TPO," *Additives for Polyolefins*, Second Edition 2015.
Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from The Engine and the Atmosphere: An Introduction to Engineering by Z. Warhaft, Cambridge University Press, (1997).
Tsai et al., "Microvascular perfusion upon exchange Transfusion with stored red blood cells in normovolemic anemic conditions," *Transfusion* 44: 1626-34 (2004).
Tsantes et al., "Redox imbalance, macrocytosis, and RBC homeostasis," *Antioxid Redox Signal* 8: 1205-16 (2006).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "Improved oxygen delivery to the myocardium during hypothermia by perfusion with 2,3 DPG-enriched red blood cells," *Am Thorac Surg* 30: 527-35 (1980).
Valeri, "Circulation and hemostatie effectiveness of platelets stored at 4 C or 22 C: studies in aspirintreated normal volunteers," *Transfusion* 16: 20-3 (1976).
Valeri, "Hemostatic effectiveness of liquid-preserved and previously frozen human platelets," *N Engl J Med* 290: 353-8 (1974).
Valeri et al., "The survival, function, and hemolysis of human RBCs stored at 4° C. in additive solution (AS-l, AS-3, or AS-S) for 42 days and then biochemically modified, frozen, thawed, washed, and stored at 4° C. in sodium chloride and glucose solution for 24 hours," *Transfusion*, 40:1341-1345 (2000).
Van Buskirk et al., "Comparison of Cytokine, Cell-free Hemoglobin, and Isoprostane Accumulations in Packed Red Blood Cells During Novel Anaerobic and Conventional Cold Storage," Transfusion 54S: SP53 (2014).
Van Buskirk et al., "Comparison of microparticles production in packed red blood cells stored under anaerobic and conventional cold storage condition," *Vox Sang* 105 (S1): 150 (2007).
Van Buskirk et al., "Evaluation of Select Red Blood Cell Biochemical and Coagulation Properties in Whole Blood Stored Using a Novel Anaerobic Storage Platform," *Transfusion* 56: 54A (2016).
Van der Meer et al., "Platelet preservation: Agitation and containers," *Transfusion and Apheresis Science* 44:297-304 (2011).
Van Slyke, "An Apparatus for Determination of the Gases in Blood and Other Solutions," *Chemistry* 7:229-231 (1921).
Voigt et al., "Effects of a restrictive Blood Transfusion protocol on acute pediatric burn care: Transfusion threshold in pediatric burns," *J Trauma Acute Care Surg* 85: 1048-54 (2018).
Vrielink et al., "Transfusion-transmissible infections," *Current Opinion in Hematology* 5:396-405 (1998).
Wallvik et al., "Platelet Concentrates Stored at 22° C. Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Wang et al., "The contribution of oxidative stress to platelet senescence during storage" *Transfusion* (2019).
Weinberg et al., "Transfusions in the Less Severely Injured: Does Age of Transfused Blood Affect Outcomes?," *The Journal of Trauma*, 65(4):794-798 (2008).

Wilding et al., "Manipulation and Flow of Biological Fuids in Straight Channels Micromachined in Silicon," *Clinical Chemistry*, 40(1):43-47 (1994).
Williams, "Blood Transfusion on Cruise Ships; A 36 Month Review of Preliminaly Data," *THOR Trauma Hemostasis & Oxygenation Research Network, RDCR Symposium*, Bergen (2013).
Williams et al., "Transfusion of Anaerobically Stored Red Blood Cells Improves Recovery in Experimental Rat Hemorrhagic Shock Model," *Transfusion* 57: 33A (2017).
Williams et al., "Transfusion of Anaerobically Stored Red Blood Cells Improves Recovery in Experimental Rat Hemorrhagic Shock Model," *Shock Abstract* (2019).
Winter, "Red blood cell in vitro quality and function is maintained after S-303 pathogen inactivation treatment," *Transfusion* 54:1798-1807 (2014).
Wolfe et al., "Molecular defect in the membrane skeleton of blood bank-stored red cells. Abnormal spectrin-protein 4.1-actin complex formation," *J Clin Invest* 78: 1681-6 (1986).
Wolfe, "Oxidative injuries to the red cell membrane during conventional blood preservation," *Semin Hematol* 26: 307-12 (1989).
Wood et al., "The Viability of Human Blood Stored in Phosphate Adenine Media," *Transfusion* 7 , 401-408 (1967).
Woodson, "Functional consequences of altered blood oxygen affinity," *Acta Biol Med Ger* 40: 733-6 (1981).
Wu et al., "Polymer microchips bonded by $O_2$-plasma activation," *Electrophoresis*, 23:782-790 (2002).
Yalcin et al., "Increased hemoglobin 02 affinity protects during acute hypoxia," *Am J. Physiol Heart Circ Physiol* 303: H271-81 (2012).
Yazer et al., "Coagulation factor levels in plasma frozen within 24 hours of phlebotomy over 5 days of storage at 1 to 6° C.," *Transfusion*, 48:2525-2530 (2008).
Yhap et al., "Decreased oxygen uptake with stored blood in the isolated hindlimb" *J Appl Physiol* 38: 882-885 (1975).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Yoshida et al., "Oxygen content—uncontrolled and overlooked parameter associated with stored red cell concentrate: Unexpectedly wide distribution," *Vox Sang* 112: P-244 (2017) Abstract.
Yoshida et al., "Enhancing uniformity and overall quality of red cell concentrate with anaerobic storage," *Blood Transfus* 15: 172-81 (2017).
Yoshida et al., "Toward a comprehensive biochemical model of human erythrocyte: relationship between metabolic and osmotic state of the cell and the state of hemoglobin," *Prog Clin Biol Res* 319: 179-93; discussion 94-6 (1989).
Yoshida et al., "Unexpected Variability of Hemoglobin Oxygen Saturation in Packed Red Blood Cells upon Donation Suggests Uncontrolled and Overlooked Parameter Associated with the Development of the Storage Lesion," *Transfusion* 57 (2017).
Yoshida et al., "Red blood cell storage lesion: causes and potential clinical consequences" *Blood Transfus* 17: 27-52 (2019).
Yoshida et al., "Reduction of Microparticle Generation During Anaerobic Storage of Red Blood Cells," *Transfusion* 52: 83A (2012).
Yuasa et al., "Improved extension of platelet storage in a polyolefin container with higher oxygen permeability," *British Journal of Hematology* 126:153-159 (2004).
Zaroulis, et al., "Lactic acidemia in baboons after Transfusion of red blood cells with improved oxygen transport function and exposure to severe arterial hypoxemia," *Transfusion* 19: 420-5 (1979).
Zavizion et al., "Inactivation of mycoplasma species in blood by INACTINE PEN110 process," *Transfusion* 44:286-293 (2004).
Zhang et al., "Modification of Si(100) surface by the grafting of poly(ethylene glycol) for reduction in protein adsorption and platelet adhesion," *J Biomed Mater Res*, 56:324-332 (2001).

(56) References Cited

OTHER PUBLICATIONS

Zielinski et al., "Back to the future: The renaissance of whole-blood transfusions for massively hemorrhaging patients," *Surgery* 155(5) 883-886 (2014).
Zielinski, et al., "Prehospital Blood Transfusion programs: Capabilities and lessons learned," *J Trauma Acute Care Surg* 82: S70-s8 (2017).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Zingarelli et al., "Part 1: Minimum Quality Threshold in Preclinical Sepsis Studies (MQTiPSS) for study design and humane modeling endpoints," *Shock* 51: 10-22 (2019).
Zink et al., "Noninvasive Evaluation of Active Lower Gastrointestinal Bleeding: Comparison Between Contrast-Enhanced MDCT and 99mTcLabeled RBC Scintigraphy," *American Journal of Roentgenology* 191: 1107-14 (2008).
Zinkham et al., "Carboxyhemoglobin levels in an unstable hemoglobin disorder (Hb Zurich): effect on phenotypic expression," *Science* 209: 406-8 (1980).
Zolla et al., "Classic and alternative red blood cell storage strategies: seven years of '-omics' investigations," *Blood Transfus* 13:21-31 (2015).
Horowitz, "Oxygen Concentration of Blood: PO2, Co-Oximetry, and More," Retrieved from the internet: https://www[dot]aacc[dot]org/~/media/files/meetings-and-events/resources-from-past-events/conference/2013/professional-practice/april-28/gc_oxygen-concentration_of_blood_apr_28_2013.pdf?la=en (2013).
Basu et al., "Overview of blood components and their preparation," Indian J Anaesth 58:529-537 (2014).
Ben-Hur et al., "Virus inactivation in red cell concentrates by photosensitization with phthalocyanines: protection of red cells but not of vesicular stomatitis virus with a water-soluble analogue of vitamin E," *Transfusion* 35:401-406 (1995).
Ben-Hur et al., "Photochemical Decontamination of Red Cell Concentrates with the Silicon Phthalocyanine PC4 and Red Light," *Dev Biol* (Basel) 102:149-156 (1999).
Chatpun et al., "Effects of plasma viscosity modulation on cardiac function during moderate hemodilution," *Asian J Transfus* Sci 4:102-108 (2010).

Extended European Search Report dated Aug. 2, 2022 in European Application No. 22151803.8.
Horowitz et al., "Inactivation of viruses in blood with aluminum phthalocyanine derivatives," *Transfusion* 31(2):102-108 (1991).
Lin et al., "Photochemical treatment of platelet concentrates with amotosalen and long-wavelength ultraviolet light inactivates a broad spectrum of pathogenic bacteria," *Transfusion* 44:1496-1504 (2004).
Prince et al., "Strategies for Evaluation of Enveloped Virus Inactivation in Red Cell Concentrates Using Hypericin," *Photochem Photobiol* 71(2):188-195 (2000).
Sandler, "The status of pathogen-reduced plasma," *Transfus Apher Sci* 43:393-399 (2010).
Skripchenko et al., "Thiazole orange, a DNA-binding photosensitizer with flexible structure, can inactivate pathogens in red blood cell suspensions while maintainng RBC storage properties." *Transfusion* 46:213-219 (2006).
Skripehenko et al., "In vivo recovery and survival of red cells after photodynamic treatment with thiopyiylium and red light using a canine model," *Vox Sang* 92(2):157-159 (2007).
Stassinopoulos et al., "Baterial inactivation in leukoreduced PRBC treated with HELINX," *Transfusion* 40(Suppl):38S (abstract S139-0401) (2000).
Van 'tEvre et al., "The concentration of glutathione in hyman erythrocytes is a heritable trait," *Free Radic Biol Med* 65:742-749 (2013).
Wagner et al., "Red cell alterations associated with virucidal methylene blue phototreatment," *Transfusion* 33(1):30-36 (1993).
Wagner et al., "Preservation of red cell properties after virucidal phototreatment with dimethylmethylene blue," *Transfusion* 38:729-737 (1998).
Wagner et al., "Developing pathogen reduction technologies for RBC suspensions," *Vox Sanguinis* 100:112-121 (2011).
Wagner et al., "Use of a flow-cell system to investigate virucidal dimethylmethylene blue phototreatment in two RBC additive solutions," *Transfusion* 42:1200-1205 (2002).
Seltsam, "UVC irradiation for pathogen reduction of platelet concentrates and plasma," Transfus Med Hemother 38:43-54 (2011).
Chinese Search Report dated Aug. 8, 2023, issued in Chinese Appln. 202080090492.1.
U.S. Appl. No. 16/304,611, filed Nov. 26, 2018, which issued as U.S. Pat. No. 11,147,876 on Oct. 19, 2021.
U.S. Appl. No. 16/412,084, filed May 14, 2019, which issued as U.S. Pat. No. 10,583,192 on Mar. 10, 2020.

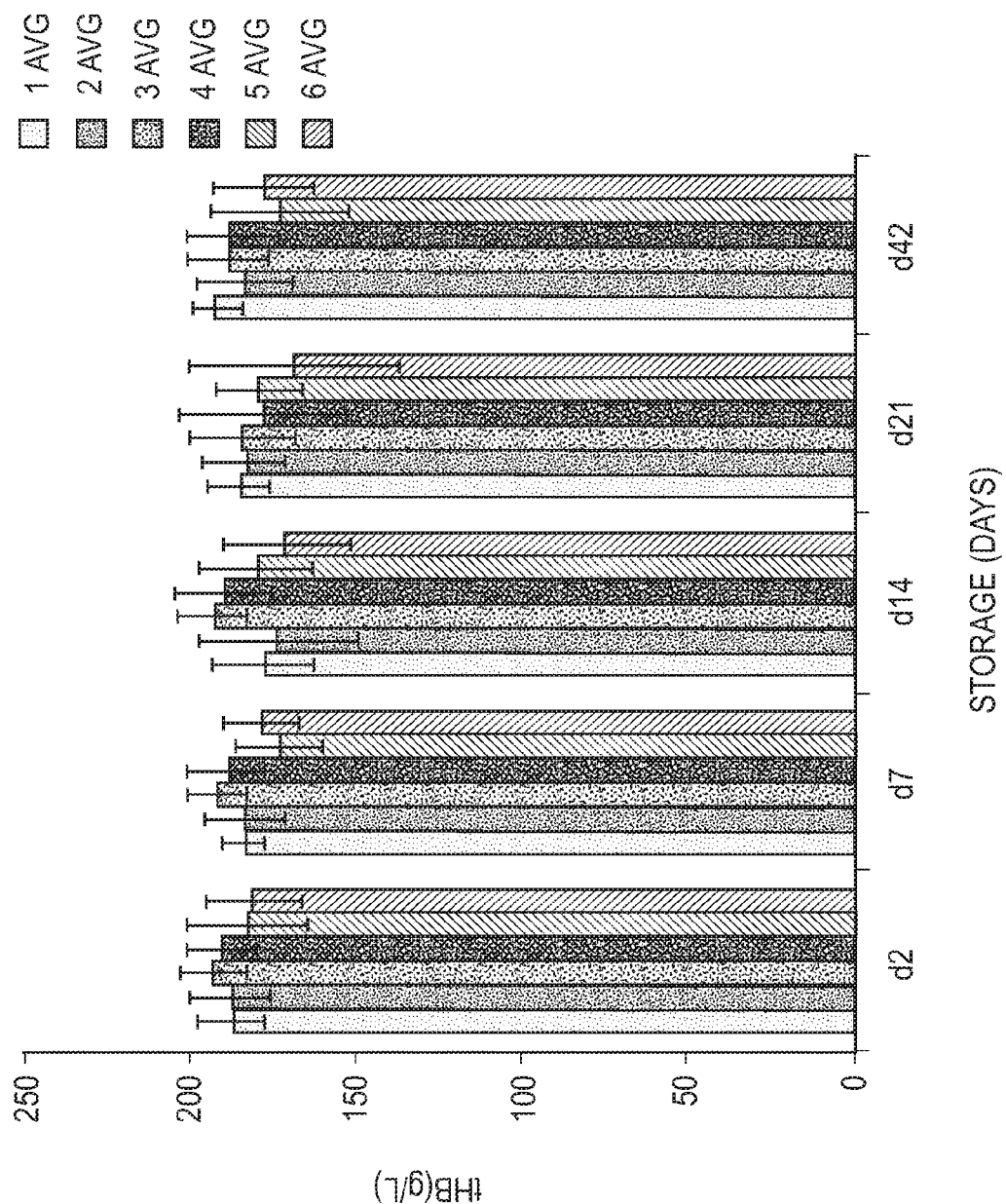

ANAEROBIC BLOOD STORAGE AND PATHOGEN INACTIVATION METHOD

CROSS-REFERENCE TO RELATED APPLICATIONS

This application a divisional of U.S. application Ser. No. 16/304,611, filed Nov. 26, 2018 (now U.S. Pat. No. 11,147,876, issued Oct. 19, 2021), which is a U.S. National Stage application of International Patent Application No. PCT/US2017/034410, filed May 25, 2017, which claims benefit of U.S. Provisional Application No. 62/342,756, filed May 27, 2016, and U.S. Provisional Application No. 62/445,081, filed Jan. 11, 2017, each of which are incorporated by reference in their entireties.

FIELD OF THE INVENTION

The present disclosure relates methods to improve the quality and safety of blood and blood products for use in transfusion medicine.

BACKGROUND OF THE INVENTION

The use of blood and blood components for transfusion is a common practice in current medicine, but presents a risk to patients with respect to the potential for exposure to immunogenic and pathogenic contaminants. The practice of storing the collected blood and blood components for up to several weeks exacerbates this risk. Whole blood is typically processed by filtration to remove leukocytes (leukoreduction), then centrifuged to separate the 3 major blood components of plasma, platelets, and red blood cells. The leukoreduced packed red blood cells (LRpRBC) are then typically suspended in an additive solution, such as AS-1 (Adsol®), AS-3)(Nutricel®, AS-5 (Optisol®), and AS-7 (SOLX®) in the United States, or SAGGM or PAGGSM in the EU, to prolong storage life before refrigerated storage for up to 42 days. Plasma is typically frozen within 24 hours of phlebotomy and separation ("Fresh Frozen Plasma"—FFP or FP24). The FFP is thawed before use and must be used within 5 days of thawing. Platelets (PLT) are collected by apheresis or by pooling the PLT fractions separated from multiple units of whole blood. PLT collected by apheresis are typically suspended in additive solutions such as PAS-C (Intersol®) or PAS-F (Isoplate®) in EU (not yet in US). PLT are kept agitated at room temperature to prevent PLT activation and must be used within 5 to 7 days of collection. While all blood components are susceptible to donor viral and bacterial contamination, due to the storage conditions, PLT are more susceptible to bacterial contamination and proliferation than other blood components.

Recent advances in the art have provided for the inactivation of bacterial and viral pathogens by utilizing UV light to irradiate the blood components with photosensitizers prior to storage (see for example the psoralen-based INTERCEPT® system, the riboflavin-based MIRASOL®) system), and also without photosensitizers (THERAFLEX® UV-Platelet system). These systems cross-link and inactivate the DNA in the pathogenic species and thereby reduce the risk they pose to the patient. The INTERCEPT® system uses amotosalen HCl (a synthetic psoralen) and UV-A light delivered at a radiant exposure of 3 J/cm$^2$ to cross-link the pathogen DNA, with the removal or reduction of residual amotosalen and photoproducts after treatment. The Mirasol® system uses riboflavin and UV light centered near 313 nm to target absorption by riboflavin-nucleotide complexes. Systems without photosensitizers typically use UV-C light at 254 nm. Long-term effects of some photosensitizers and photoproducts in these systems remain to be established.

Other advances in the art include the use of S-303 (Cerus Corporation, Concord, CA), an alkylating agent based on quinacrine mustard that includes a frangible anchoring group, to crosslink nucleic acids and inactivate infectious bacteria and other pathogens (see Henschler et al. "Development of the S-303 pathogen inactivation technology for red blood cell concentrates," *Transfus Med Hemother* 38:33-42 (2011) ("Henschler 2011")). Not to be limited by theory, it is thought that there are two reactions that form the basis of the S-303 pathogen inactivation process. The first reaction is the formation of covalent DNA and RNA adducts by reaction with the S-303 molecule. This first reaction is complete within approximately 30 minutes. The second reaction is the degradation of excess S-303 into the less toxic byproduct, S-300. This decomposition occurs concurrently with the adduct reaction and is complete within 16-18 hours.

While not limited to any particular theory, the formation of covalent DNA and RNA adducts with S-303 is thought to be based on the intercalation of the molecule with a nucleic acid polymer (e.g., DNA or RNA). As currently understood, when S-303 is added to the RBCs, it rapidly (within seconds to minutes) passes through the membranes, including those of cells and viral envelopes due to its amphipathic character and intercalates into the helical regions of nucleic acid. It is hypothesized that the presence of a frangible anchor on the molecule assists in the intercalation process by the attraction of the positively charged amine groups on the molecule to the negative charges in the nucleic acid chains of DNA or RNA. Close proximity of the S-303 molecule allows for thermal cycloaddition reactions to rapidly occur, covalently bonding the S-303 molecule to the DNA or RNA. It is believed that the covalent linkage prevents replication or translation processes from occurring and further halts the production of additional pathogens. During the process of forming the covalent adduct, the frangible anchor is removed by hydrolysis, yielding the less toxic compound S-300.

The spontaneous decomposition of S-303 to the less toxic 5300 is the second reaction in the pathogen inactivation process. An excess of S-303 (approximately 0.2 mM) is normally added to the RBCs to provide enough reagent to completely react with all of the DNA and RNA in the sample. However, S-303 is a toxic compound so in order to safely transfuse the resulting product, residual S-303 must be removed. In the Cerus pathogen inactivation process, this is mainly achieved by allowing the S-303 to degrade to S-300, a compound with significantly less toxicity. The degradation process occurs by hydrolysis; the hydrolysis of S-303 is triggered by the shift in pH from low to high when the S-303 reagent is initially mixed with the RBCs. The decomposition kinetics of the residual S-303 are rapid at concentrations above 10 nM/L with half-life of about 20 minutes.

As currently understood, S-303 also has the potential to react with other nucleophiles in a unit of RBCs, including small molecules such as phosphates, water and macromolecules such as proteins. While not limited to any particular theory, to reduce these nonspecific interactions with proteins, 20 mM of glutathione (GSH) is simultaneously added to the RBCs during the pathogen inactivation process. (See Henschler 2011). Glutathione (GSH) is a naturally occurring antioxidant present in most cells at an intracellular concentration of about 5 mM. As currently understood, GSH distributes only in the extracellular plasma space, while the S-303 diffuses across membranes and equilibrates inside and outside of cells. This allows GSH to quench extracellular reactions of S-303 without a significant impact on the pathogen inactivation (See Olcina et al. Hypoxia and the DNA damage response. *Hypoxia and Cancer in Cancer Drug Discovery and Development* 2014; Chapter 2:21-30; Melillo G (ed)).

Recent advances in the art also include the use of anaerobically stored packed red blood cells in additive solution to reduce the amount of storage lesions commonly associated with the use of older blood (see Bitensky, et al. U.S. Pat. No. 5,789,152; Bitensky, et al. U.S. Pat. No. 6,162,396; and Bitensky, et al. U.S. Pat. No. 8,071,282). These storage lesions are thought to be derived from the metabolic processes and byproducts that result from storing the blood without the normal physiological environment of the circulatory system, and that the removal or reduction of available oxygen in the stored blood reduces the creation of damaging oxidative species within the red blood cell during storage.

Hemolysis is recognized as an important indicator of blood quality and safety. During storage, hemolysis levels increase over time and it the presence of the free hemoglobin is an indicator that the blood has exceeded its shelf life. From this, regulations and guidelines have developed that limit the acceptable storage times for units of blood products that can be used for transfusions. The importance of hemolysis for blood safety has led Europe to set an upper limit of 0.8% before the blood must be discarded. The FDA recommends that the level of hemolysis not exceed 1.0%. Thus, methods that reduce hemolysis extend the safe shelf life of the blood, decreasing costs and increasing blood availability.

Another indicator of stored blood health and safety are microparticles. See, Cognasse et al., "The role of microparticles in inflammation and transfusion: A concise review," Transfus. Apher. Sci. 53(2):159-167 (2015). Microparticles (Mps) are produced by red cells, leukocytes, platelets and endothelial cells. Microparticles are thought to be produced as result of normal physiology, apoptosis, or cell damage. Generally, they are described as particles less than 1000 nm. A lower range is sometimes indicated at 50 nm but there is no clear definition or agreement regarding the lower limit. Usually, a flow cytometer in conjunction with fluorescent surface antibody is used for quantification, but there is no generally accepted method for MP measurement, and measurements can depend on the instrument used. See Poncelet et al., "Tips and tricks for flow cytometry-based analysis and counting of microparticles," Transfus. Apher. Sci. 53(2): 110-126 (2015). Composition of Mps reflect the parent cell from which they are derived, although only selected molecules are included or exposed on the surface of the resulting MPs. Some of the MPs are considered highly thrombogenic (especially MPs of platelet origin). Generally Mps in stored RBC components are harmful to recipients as sources for immune modulation, hyper coagulation, nitric oxide scavenging (poor blood perfusion), or development of alloimmunity. Accordingly, methods that result in reduced levels of microparticles provide for improved stored blood health and safety.

Here we demonstrate that reduced oxygen in whole blood provides for unexpected reductions in the amount of hemolysis and microparticle production when treating blood products to reduce a disease-causing viruses, bacteria, and multi-cellular parasites, and reduce white blood cells. The methods provided in the present specification provide for extending the usable life of pathogen reduced blood products by reducing hemolysis.

Pathogen inactivation of blood and blood products has been developed to improve their safety. Although a variety of bacteria, viruses and parasites can be inactivated, research studies demonstrate the negative impact to blood components. Currently, plasma and platelet concentrates can be treated with pathogen inactivation systems; however, red blood cell treatment is still under development. Pathogen inactivation of whole blood after donation would provide the advantage that all products derived are pathogen inactivated along with destruction of residual white cells. However, recent studies demonstrated that the quality of red blood cells derived from whole blood illumination using the riboflavin/UV light technology (Mirasol, TerumoBCT) is significantly reduced compared to the untreated study arm to the extent that it would require a shortening if the shelf life under standard storage conditions. The hallmark of these analyses is the accelerated development of hemolysis which reaches the current acceptance level of 0.8% at about day 30 of blood bank storage. The creation of reactive oxygen species (ROS) during the UV illumination is one the contributors to hemolysis.

Here we demonstrate that reduction of oxygen from whole blood prior to treatment for pathogens using the Mirasol system improves the blood quality. The Hemanext™ system (New Health Sciences) designed to remove oxygen from whole blood and red cell concentrates combined with pathogen reduction results in improved red blood cell quality compared to pathogen reduction under non-oxygen reduced conditions. Hemanext™ processing combined with Mirasol pathogen reduction treatment results in blood having less than 0.8% blood hemolysis after 42 days of storage under oxygen reduced conditions.

SUMMARY OF THE INVENTION

The present disclosure provides a method for inactivating blood pathogens and reducing hemolysis during storage by removing oxygen from a blood product, adding riboflavin to a final concentration of between 40 to 60 µM, and irradiating the riboflavin containing blood product with UV light between 265-400 nm.

The present disclosure provides for a method reducing microparticle formation and inactivating blood pathogens by removing oxygen from a blood product, adding riboflavin to a concentration of between 40 to 60 µM and irradiating the riboflavin containing blood product with UV light between 265-400 nm.

The present disclosure provides for oxygen reduced whole blood comprising whole blood collected in CPD, having between 40 to 60 µM riboflavin, having an oxygen saturation (SO2) of less than 25%, and having a pCO2 of 90 mmHg or less at 37° C., wherein the oxygen reduced whole blood has been irradiated with UV light between 265 to 400 nm The present disclosure provides for oxygen and carbon dioxide reduced whole blood comprising whole blood collected in CPD, having between 400 to 60 µM riboflavin, having an oxygen saturation (SO2) of less than 25%, and having a pCO2 of 20 mmHg or less at 37° C., wherein the oxygen reduced whole blood has been irradiated with UV light between 265 to 400 nm.

The present disclosure provides for a method for inactivating blood pathogens and reducing hemolysis by removing oxygen from a blood product, adding S-303 to a final concentration of 0.2 mM, and adding GSH to a final concentration of between 2 to 20 mM.

The present disclosure provides for a method for inactivating blood pathogens and reducing microparticle production by removing oxygen and carbon dioxide from a blood product, adding S-303 to a final concentration of 0.2 mM, and adding GSH to a final concentration of between 2 to 20 mM.

The present disclosure provides for oxygen reduced red blood cells having a final concentration of approximately 0.2 mM S-303, having an oxygen saturation (SO2) of less than 25%, and having a pCO2 of 90 mmHg or less at 37° C.

BRIEF DESCRIPTION OF THE DRAWINGS

The present disclosure is disclosed with reference to the accompanying drawings, wherein:

FIG. 6A to 6G are graphs presenting the results of an experiment according to the present disclosure comparing the osmotic fragility (6A), potassium (6B), total hemoglobin (6C), oxygen saturation (6D), glucose (6E), lactate (6F) and pH (6G) of control whole blood with sterile saline (1 avg), control whole blood with riboflavin (2 avg), oxygen reduced packed RBCs with sterile saline (3 avg), oxygen reduced pRBCs with riboflavin (4 avg), oxygen reduced whole blood with sterile saline (5 avg), and oxygen reduced whole blood with riboflavin (6 avg).

Corresponding reference characters indicate corresponding parts throughout the several views. The examples set out herein illustrate aspects of the present specification but should not be construed as limiting the scope of the present specification in any manner.

DETAILED DESCRIPTION

Figure 1:
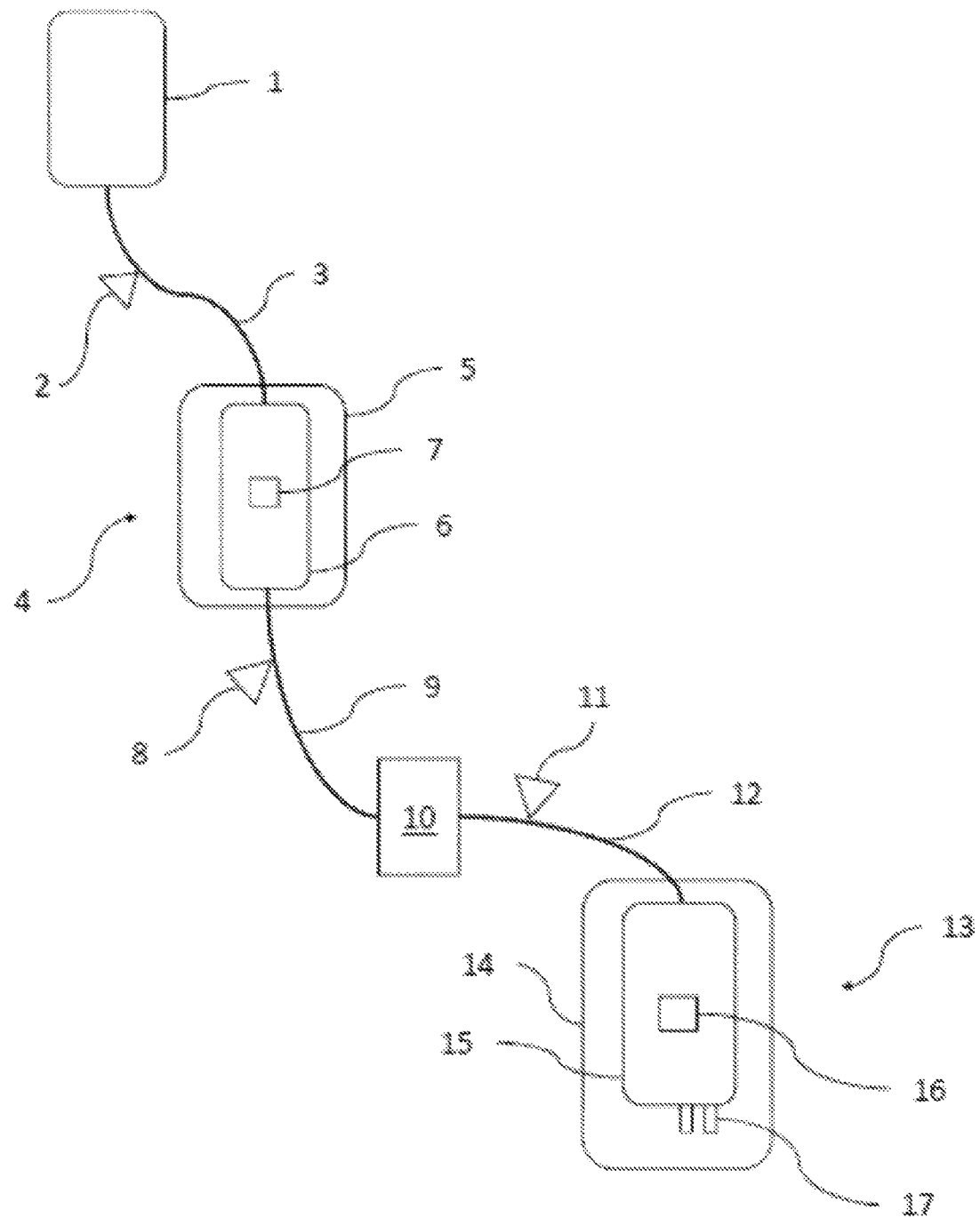
FIG. 1 presents a diagram illustrating a blood bag collection and storage system according to an aspect of the present specification.

Here we show that the harmful side effects of irradiating blood samples with UV light can be mitigated by reducing the amount of oxygen present in the sample. Not to be limited by theory, it is thought that the reduction in oxygen decreases the generation of reactive oxygen species (ROS). The reduction of ROS is thought to increase the beneficial aspects of UV light irradiation for pathogen inactivation in blood samples, whether the sample be whole blood or any blood component, such as plasma, platelets, or red blood cells.

In accordance with aspects of the present specification, a blood processing and storage system may collect, separate, deoxygenate, and irradiate blood components with UV light prior to storage. The blood processing system may be a gravity driven bag system, such as is commonly used in whole blood leukoreduction. In some aspects the blood processing system may be an apheresis system of either the continuous or discontinuous flow type, as is commonly known in the art, wherein the blood is collected and separated into desired components and the desired components are then deoxygenated and irradiated in accordance with the present specification prior to storage. In some aspects the blood is collected and deoxygenated before separation and UV irradiation of the desired blood component before storage. In some aspects the blood is collected and separated before deoxygenation and UV irradiation of the desired blood component before storage. In some aspects the blood is collected, deoxygenated, and UV irradiated before separation and storage of the desired blood components.

It will be appreciated by one of ordinary skill in the art that the following examples and drawings are intended for illustration only and are not meant to be limiting as to the scope of the invention. For the purposes of the present specification and description, the following definitions and terms are understood to have their common meaning. The term "UV" refers to ultraviolet light, having a wavelength of about 220 nm to about 400 nm, and generally includes the peak from a mercury arc lamp at 405 nm. The term "blood sample" is meant to refer to a sample of blood from an animal or human, and includes whole blood and components of whole blood, including red blood cells (RBC), platelets (PLT), plasma, leukocytes, proteins commonly found in blood, such as albumin, enzymes, clotting factors, and also includes combinations of such components commonly found in blood, such as partially separated fractions of whole blood, recombined components previously separated, and includes freshly collected or stored blood samples. The term "apheresis" is meant to have its common meaning in the art and includes the collection and separation of blood by both continuous and discontinuous methods, as are commonly known in the art. The term "apheresis system" is meant to have its common meaning in the art and includes devices and systems for the collection and separation of blood by both continuous and discontinuous methods, as are commonly known in the art. The term "blood container" is meant to refer to any container made from polymeric materials for the purpose of storing blood, regardless of the duration of storage, and includes the generic term "blood bag" as is commonly used in the art. The term "PVC" is meant to refer to the polymer comprised of polyvinylchloride, and includes PVC with any added materials, such as plasticizers, stabilizers, inhibitors, and other materials commonly known in the art and used in the manufacture of PVC.

FIG. 1 shows an aspect of the present specification comprising a blood collection bag 1, a blood processing bag 4, a UV irradiation chamber 10, and a blood storage bag 13. The blood collection bag 1 is commonly known in the art and typically made from flexible plastic, such as polyvinyl chloride (PVC), but can be made from other polymer materials such as urethane, silicone, or other biocompatible materials. The blood collection bag 1 has a blood transfer line 3. The blood transfer line 3 is also made from flexible plastic as is commonly known in the art, and is typically made from PVC, but can also be made from other biocompatible polymeric materials. The blood transfer line 3 is fitted with a flow control device 2, such as a pinch clamp, a ratchet clamp, or a frangible seal to prevent the flow of blood from the collection bag 1 through the transfer line 3 into the processing bag 4 until such flow and transfer of blood is desired. In some aspects the flow control device is designed to control the rate of flow.

The processing bag 4 is comprised of an outer barrier bag 5 and an inner blood bag 6, wherein the outer barrier bag 5 is substantially impermeable to oxygen. Materials suitable for construction of the barrier bag 5 are commonly known in the art and include metallic foils, such as aluminum foil, polymer films having suitable barrier properties, such as ethyl vinyl alcohol (EVA), polyvinyl alcohol (PVA), polyacrylonitrile (Barex®), cyclic polyolefins, polychlorotrifluoroethylene (PCTFE or Aclar®)), polyvinylidene chloride (PVDC), polymer films with coatings to provide suitable barrier properties, such as by coating polyethylene or nylon film with a coating of silicon oxide, aluminum oxide, or multilayer films comprising a combination of polymer films and/or coatings to provide suitable barrier properties. In aspects the barrier bag is made from RollPrint ClearFoil® Z film or Renolit Solmed Wrapflex® film. Exemplary methods for the production of processing bags are provided in International Patent Application No. PCT/US2016/021794, filed Mar. 10, 2016, hereby incorporated by reference in its entirety.

The inner blood bag 6 is made from flexible polymer materials having high oxygen transfer properties that are commonly known in the art, and include PVC, urethanes, silicones, polyethylene, polypropylene, polyethersulfone, polyvinylidene fluoride (PVDF). In an aspect the inner blood bag 6 is made from silicone, such as for example Wacker Silpuran® 30-um thick silicone film. In another aspect the inner blood bag 6 is made from Millipore GVHP29325 PVDF membrane. An oxygen absorbing sorbent material 7 is disposed between the outer barrier bag 5 and the inner blood bag 6. The oxygen absorbing sorbent material 7 is commonly known in the art and is typically comprised of an iron-based sorbent material, such as the Mitsubishi Ageless® series of oxygen absorbers, or other oxygen absorbing materials or systems, such as ascorbate/metallic salt systems, metal catalysts such as platinum, or oxygen absorbing polymers such as nylon MXD6. In some aspects the outer barrier bag 5 and inner blood bag 6 can be laminated together with the oxygen absorbing material 7 disposed within the laminated structure, such as the Mitsubishi Ageless® OMAC® film.

The oxygen absorbing sorbent material 7 is typically disposed in a breathable sachet and is adapted to absorb the oxygen in the gas headspace between the outer barrier bag 5 and the inner blood bag 6. In some aspects the oxygen absorbing sorbent material 7 is affixed to a plastic mesh structure (not shown) to provide for spacing between the inner and outer bags and thus provide for enhanced gas transfer in the gas headspace. In some aspects a plurality of oxygen absorbing sachets are disposed in the gas headspace. In aspects the oxygen absorbing sorbent material 7 is formulated to be fast acting and absorb high levels of oxygen quickly, with a capacity to absorb the entire oxygen content of a full unit of blood. In aspects the oxygen absorbing capacity of the oxygen absorbing sorbent material 7 is at least 100 cc oxygen, and more preferably at least 200 cc. In some aspects an oxygen indicator tab (not shown) is disposed in the gas headspace to indicate by color the presence or absence of oxygen at a particular level, such as for example the Sorbent Systems Tell-Tab®. Additional details of processing bags 4 and inner blood bags 6 suitable for the present specification are provided in International Patent Application No. PCT/US2016/021794, filed Mar. 10, 2016.

The fluid path of the inner blood bag 6 is connected to UV irradiation chamber 10 by blood transfer line 9 having a flow control device 8, such as a pinch clamp, a ratchet clamp, or a frangible seal to prevent the flow of blood from the inner blood bag 6 through the transfer line 9 into the UV irradiation chamber 10 until such flow and transfer of blood is desired. In some aspects the flow control device is designed to control the rate of flow. The UV irradiation chamber 10 is further fluidly connected to a blood storage bag 13 by a blood transfer line 12 having a flow control device 11, such as a pinch clamp, a ratchet clamp, or a frangible seal to prevent the flow of blood from the UV irradiation chamber 10 through the transfer line 12 into the blood storage bag 13 until such flow and transfer of blood is desired. In some aspects the flow control device 11 is designed to control the rate of flow, and in some aspects the flow control device is in communication with the UV lamp to provide for a controlled irradiation exposure of the blood sample contained within the UV irradiation chamber.

The UV irradiation chamber 10 further comprises a UV lamp (not shown) that is operatively connected to a source of power (not shown), and provides for UV irradiation of the blood contained within or passing through the chamber. In some aspects the UV irradiation chamber is adapted to receive a section of blood transfer tubing 9 and irradiate UV light through the tubing. It will be appreciated by those of ordinary skill in the art that most plastics absorb UV light at lower wavelengths and would be unsuitable for using lower wavelength UV light for processing, such as UV-C light at 254-nm, but for certain photosensitizers absorbing at higher wavelengths, such as UV-B (~290-320 nm) or UV-A (~320-400 nm) thin sections of plastic may be suitable. Thus, in some aspects a portion of blood transfer tubing 9 is adapted to be very thin in wall thickness to be adapted into UV irradiation chamber 10 to provide for enhanced light penetration through the plastic tubing into the blood sample. In some aspects the wall thickness of the portion of transfer tubing in the UV irradiation chamber is about 0.1 to about 1.0 mm, and in aspects the transfer tubing wall thickness is about 0.2 to about 0.5 mm thick.

In some aspects the UV irradiation chamber 10 is adapted to have a UV-C transparent portion, such as a section of quartz ($SiO_2$) or sapphire ($Al_2O_3$) material in fluid communication with blood transfer tubing 9 and blood transfer tubing 12. In some aspects the blood transfer line 9 is adapted to have a UV-C transparent portion, such as a section of quartz ($SiO_2$) or sapphire ($Al_2O_3$) tubing nested between blood transfer tubing 9 and blood transfer tubing 12, such that the UV-C transparent portion can be easily inserted into UV irradiation chamber 10. In some aspects the UV irradiation chamber 10 is fabricated from a UV-C transparent material, such as quartz ($SiO_2$) or sapphire ($Al_2O_3$), and is connectively adapted to and in fluid communication with blood transfer tubing 9 and blood transfer tubing 12. In some aspects the UV irradiation chamber 10 is fabricated from a material that is not transparent to UV-C, but is transparent to UV-A and or UV-B wavelengths, such as glass or polymers such as polycarbonate, acrylic, PVC, urethane and others, and is connectively adapted to and in fluid communication with blood transfer tubing 9 and blood transfer tubing 12. In some aspects the UV irradiation chamber 10 is fabricated from a polymeric material, such as silicone that is sufficiently transparent to UV-C, UV-A and UV-B wavelengths to be effective at transmitting UV light into the lumen of the irradiation chamber.

The blood storage bag 13 is comprised of an outer barrier bag 14 and an inner blood bag 15, wherein the outer barrier bag 14 is substantially impermeable to oxygen. Suitable blood storage bags 13 are described in International Patent Application No. PCT/US2016/029069, filed Apr. 22, 2016, and hereby incorporated by reference in its entirety. Briefly, materials suitable for construction of the outer barrier bag 14 are provided; the outer barrier bag 14 is substantially equivalent to outer barrier bag 5. The inner blood bag 15 is substantially equivalent to blood collection bag 1 described above, except that it further comprises spike ports 17, wherein spike ports 17 are commonly known in the art of transfusion medicine and are adapted for sterile connection of an infusion spike to receive the blood contained within the inner blood bag 15 at the time of patient use. The blood storage bag 13 further comprises an oxygen absorbing material 16 disposed between outer barrier bag 14 and inner blood bag 15. In aspects the oxygen absorbing material 16 is formulated to function at refrigerated temperatures for extended periods of time and absorb low levels of oxygen.

Figure 2:
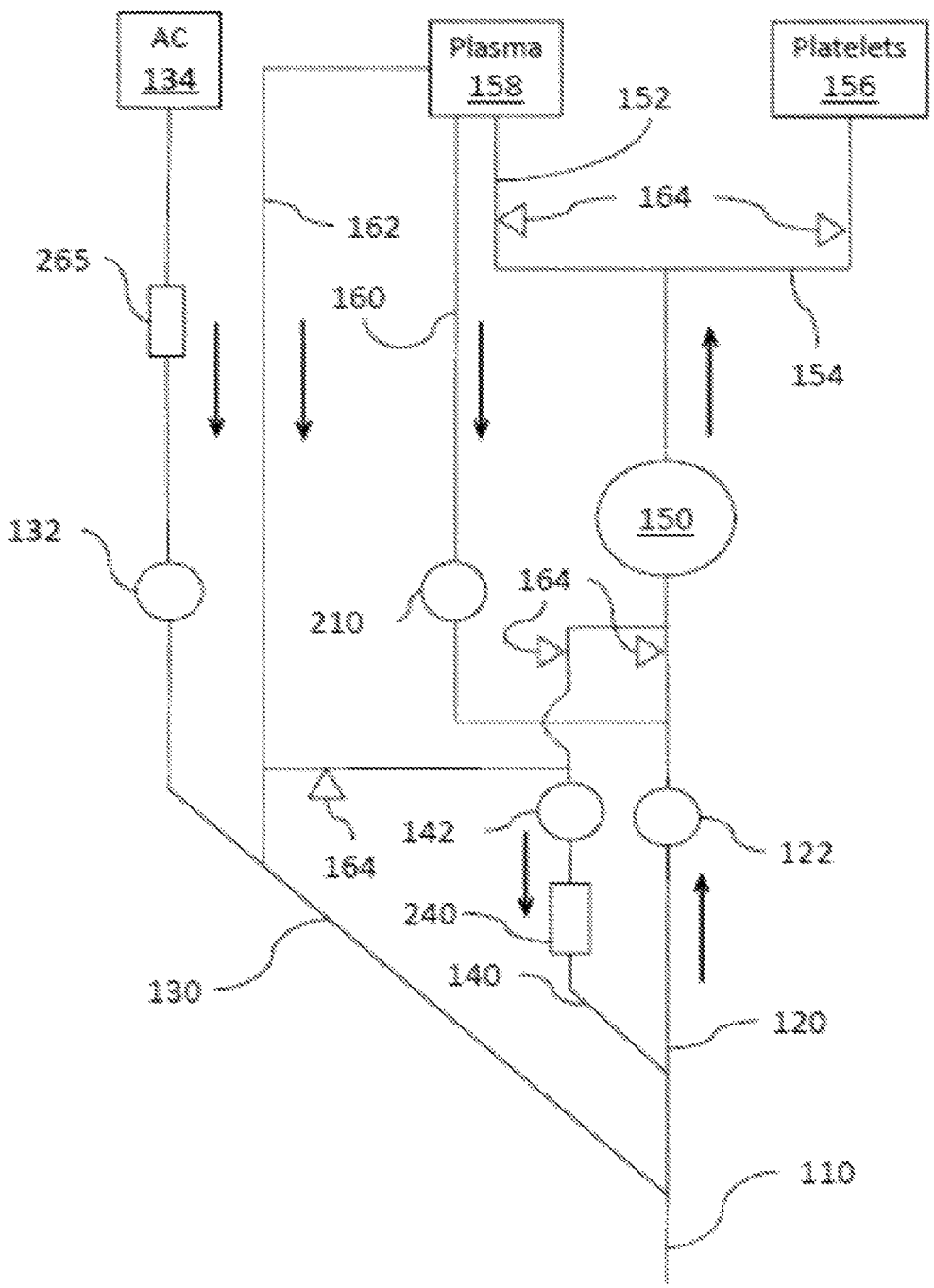
FIG. 2 presents a diagram illustrating a discontinuous apheresis system according to an aspect of the present specification.

FIG. 2 shows a discontinuous three-line apheresis system, wherein whole blood is withdrawn from a subject through a venous-access device 110 that may be inserted into the subjects arm. The blood draw line 120 fluidly connects the venous-access device 110 to a blood component separation device 150 for separation of the blood components. A draw pump 122 located on the draw line 120 controls the direction, rate, and duration of the flow through the draw line 120.

As the whole blood is being withdrawn from the subject, anticoagulant can be added to the whole blood to prevent the blood from coagulating within the lines or within the blood component separation device 150. To that end, the system includes an anticoagulant line 130 fluidly connected to an anticoagulant source 134 (e.g., a bag of anticoagulant) at one end, and the venous-access device 110 (or the draw line 120) at the other end. An anticoagulant pump 132, through which the anticoagulant line 130 passes, controls the flow through the anticoagulant line 130 and the amount of anticoagulant introduced into the whole blood. The anticoagulant pump 132 operates proportionately to the draw pump 122 to ensure that the proper amount of anticoagulant is added to the whole blood. The anticoagulant is typically introduced into the whole blood as close as possible to the venous-access device 110. The lines/conduits typically include a clamp valve 164 to stop the flow within the line.

Once the desired amount of anticoagulated whole blood is withdrawn from the subject and contained within the blood component separation device 150, the blood component separation device separates the whole blood into several blood components, typically plasma, platelets, red blood cells, and, optionally, white blood cells.

Some aspects of the blood processing system 100 include a transfer pump 210 and a dilution/extraction line 160 connected to the plasma bag 158. The transfer pump 210 and dilution/extraction line 160 can be used for a variety of purposes including dilution of the anticoagulated drawn blood being introduced into the blood component separation device. For example, if the user wishes the drawn blood to have a higher plasma content, the system can dilute the withdrawn blood by turning on the transfer pump and introducing plasma from the plasma bag 158 into the withdrawn blood within the draw line 120. Additionally or alternatively, the transfer pump may be used during surge elutriation to introduce plasma from the plasma bag 158 into the blood component separation device 150 to extract the platelets (or other blood component).

After the blood sample is separated in the blood component separation device 150 and the desired components are removed and stored in the appropriate storage container 156 or 158, the system returns un-extracted and/or unwanted components back to the subject via dedicated lines.

Figure 3:
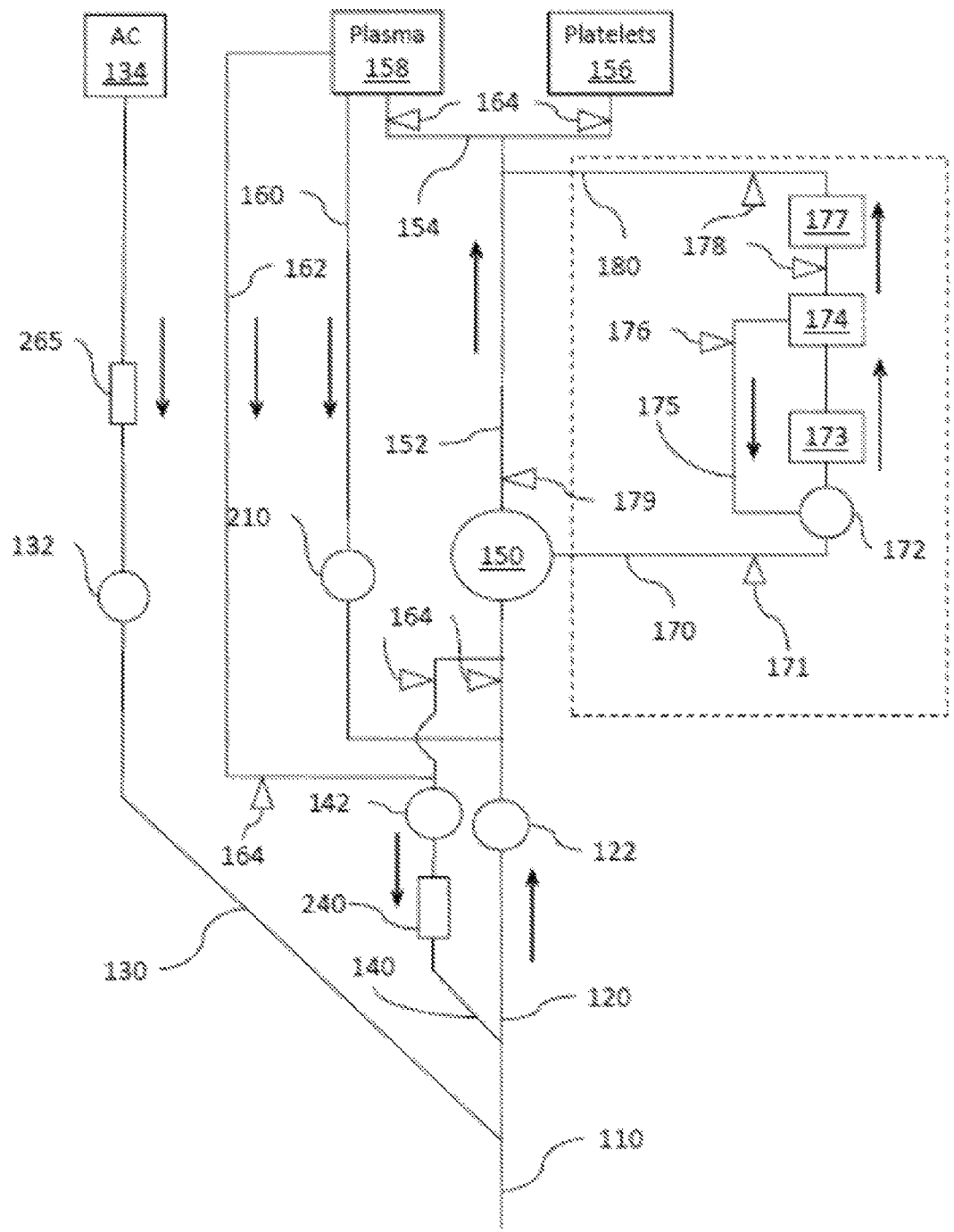
FIG. 3 presents a diagram illustrating a discontinuous apheresis system according to an aspect of the present specification.

FIG. 3 shows an aspect of the present specification for use with a discontinuous three-line apheresis system, wherein the improved portion is shown within the dashed lines. In particular, the apheresis blood processing system 100 further comprises fluid transfer pump 172, deoxygenation device 173, processing reservoir 174, and UV irradiation chamber 177, which are fluidly connected by transfer line 170 and recirculating line 175. The control of fluid flow in transfer line 170 and recirculating line 175 is maintained by control over flow control valves 171, 176, 178, and 179 acting in cooperation to direct the fluid into the desired devices.

Upon completion of separation of the blood components in blood separation device 150, the flow of the desired blood component is directed into transfer line 170 of the present specification by closing flow control valve 179 and opening flow control valve 171 of the present specification. Thus, the desired blood component is directed to the transfer pump 172 of the present specification rather than the transfer line 152 and ultimately plasma bag 158 or platelet bag 156. The flow of fluid in transfer line 170 can be directed by fluid flow from transfer pump 122 or transfer pump 210, or by transfer pump 172 of the present specification, or a combination thereof.

The flow of fluid in transfer line 170 is controlled by flow control valve 171 and flows into transfer pump 172 and continues to flow into deoxygenation device 173 and processing reservoir 174, as shown by the arrow in the drawing. During the deoxygenation process flow control valves 178 would be closed and flow control valve 176 disposed on recirculation line 175 would be open, thereby allowing fluid to be recirculated by transfer pump 172 through deoxygenation device 173, processing reservoir 174 and recirculation line 175 until the desired level of oxygen is achieved in the fluid. In some aspects the deoxygenation device 173 is comprised of hollow porous fibers commonly known in the art and used for fluid degassing, such as Membrana Liqui-Cel® and MiniModule® devices, and for blood oxygenation in cardiopulmonary bypass perfusion such as the Medtronic Affinity® series oxygenators and Sorin Inspire® series oxygenators. In some aspects deoxygenation device 173 is operably connected to a supply of nitrogen gas (not shown) to provide the hollow porous fibers with nitrogen gas to remove the oxygen from the blood. In some aspects deoxygenation device 173 is operably connected to a means of measuring the oxygen content of the fluid contained therein (not shown) to provide a means for determining when the fluid sample has been deoxygenated to a level of about 25% oxygen or less, and in aspects to about 10% oxygen or less. In some aspects the transfer pump is operably connected to a means of control for powering off the pump after a predetermined period of time that has been experimentally shown to be efficacious for the volume of fluid being treated.

After the fluid sample has been adequately deoxygenated, the blood sample is pumped through UV irradiation chamber 177 by pump 172 by opening flow control valves 178. The blood sample is irradiated with UV light from a suitable UV light source (not shown). The UV light source can be contained within the UV irradiation chamber 177 and operatively connected to a source of power (not shown), or the UV light source can be operatively connected to UV irradiation chamber, such as by a light pipe or mirror (not shown). The UV light source is known in the art and is selected based on the desired spectral output and chemistry involved in the treatment of the blood component, and can be selected from the group comprising a mercury arc lamp, a xenon lamp, a flash lamp, a deuterium lamp, a halogen lamp, a tungsten lamp, a fluorescent lamp, and a UV-emitting LED.

The flow of fluid in the UV irradiation chamber is preferably controlled such that a target radiant exposure of UV light is achieved in the fluid, either by a timed UV irradiation of a static sample contained within UV irradiation chamber 177, or by the controlled flow of a dynamic sample passing through UV irradiation chamber 177 and controlled by flow valves 178. In some aspects the radiant exposure of UV light is about 1-8 $J/cm^2$, and in aspects is about 3 $J/cm^2$. The deoxygenated and UV irradiated blood component then flows through transfer line 180 into transfer line 152 for collection and storage. Having been treated to reduce pathogens and deoxygenated to a level of less than about 25% oxygen according to the present specification, the blood component is transferred into a blood storage bag. In some aspects the transfer line 180 includes a component absorption device (not shown) to provide for the reduction of excess photosensitizer and photoproducts, such as is used with psoralens photosensitizers and is commonly known in the art.

The present disclosure provides for, and includes, methods for pathogen reduction having reduced hemolysis comprising removing oxygen from a blood product to prepare an oxygen reduced blood product, reducing blood pathogens from the blood product comprising adding riboflavin to a final concentration of between 40 to 60 µM, irradiating said riboflavin containing blood product with UV light between 265 to 400 nm. In certain aspects, the method further includes storing said oxygen reduced pathogen reduced blood product under anaerobic conditions. Also included and provided for in the present specification are methods for pathogen reduction having reduced hemolysis comprising removing oxygen and carbon dioxide from a blood product to prepare an oxygen and carbon dioxide reduced blood product, reducing blood pathogens from the blood product comprising adding riboflavin to a final concentration of between 40 to 60 µM, irradiating said riboflavin containing blood product with UV light between 265 to 400 nm. As used herein, "anaerobic conditions" includes both carbon dioxide depleted and carbon dioxide containing conditions. In most aspects, anaerobic conditions refer to both oxygen and carbon dioxide depleted storage conditions.

The present disclosure provides for, and includes, methods for pathogen reduction having reduced hemolysis comprising removing oxygen from a blood product to prepare an oxygen reduced blood product, reducing blood pathogens from the blood product comprising adding S-303 to a final concentration of between approximately 0.1 to 0.5 mM and adding glutathione (GSH) to a final concentration of between 2 to 20 mM. In certain aspects, the methods for pathogen reduction having reduced hemolysis comprise removing oxygen from a blood product to prepare an oxygen reduced blood product prior to reducing blood pathogens. In other aspects, the methods for pathogen reduction having reduced hemolysis comprise removing oxygen from a blood product to prepare an oxygen reduced blood product after reducing blood pathogens. In other aspects, the methods for pathogen reduction having reduced hemolysis comprise removing oxygen from a blood product to prepare an oxygen reduced blood product at the same time as reducing blood pathogens. Also included and provided for in the present specification are methods for pathogen reduction having reduced hemolysis comprising removing oxygen and carbon dioxide from a blood product to prepare an oxygen and carbon dioxide reduced blood product, reducing blood pathogens from the blood product comprising adding S-303 to a final concentration of approximately 0.2 mM and adding glutathione (GSH) to a final concentration of between 5 to 20 mM. In other aspects, the methods for pathogen reduction having reduced hemolysis comprise removing oxygen and carbon dioxide from a blood product to prepare an oxygen and carbon dioxide reduced blood product, and reducing blood pathogens from the blood product comprising adding S-303 to a final concentration of between approximately 0.1 to 0.5 mM and adding glutathione (GSH) to a final concentration of between 2 to 20 mM. In another aspect, the methods for pathogen reduction having reduced hemolysis comprise removing oxygen and carbon dioxide from a blood product to prepare an oxygen and carbon dioxide reduced blood product, and reducing blood pathogens from the blood product comprising adding S-303 to a final concentration of between approximately 0.1 to 0.4 mM and adding glutathione (GSH) to a final concentration of between 5 to 20 mM. In yet another aspect, the methods for pathogen reduction having reduced hemolysis comprise removing oxygen and carbon dioxide from a blood product to prepare an oxygen and carbon dioxide reduced blood product, and reducing blood pathogens from the blood product comprising adding S-303 to a final concentration of between approximately 0.1 to 0.3 mM and adding glutathione (GSH) to a final concentration of between 5 to 10 mM. In a further aspect, the methods for pathogen reduction having reduced hemolysis comprise removing oxygen and carbon dioxide from a blood product to prepare an oxygen and carbon dioxide reduced blood product, and reducing blood pathogens from the blood product comprising adding S-303 to a final concentration of between approximately 0.1 to 0.3 mM and adding glutathione (GSH) to a final concentration of between 2 to 10 mM.

As used herein, pathogens include viruses, parasites, and bacteria. Also as used herein, low levels of leukocytes that remain after leukoreduction are considered pathogens. Thus, the methods of pathogen reduction may further provide for the reduction of leukocytes that may remain after leukocyte reduction.

As used herein, the term "reducing", "reduction", or "reduced" is meant to refer to a final amount lower than an initial amount or lower relative to a control sample. A reduced level of a pathogen means that the pathogen level is reduced by at least one order of magnitude when compared to a similar untreated sample. Generally, for purposes of transfusion medicine, the levels of pathogen are reduced by at least 1.8 logs. In an aspect of the present disclosure, the levels of pathogen are reduced by at least 3 logs. In another aspect, the levels of pathogen are reduced by at least 4 logs. In another aspect, the levels of pathogens are reduced by between 3 to 10 logs. In another aspect, the levels of pathogen are reduced by at least 7 logs.

As used herein, "reducing oxygen" or "reducing oxygen saturation" refers to reductions in the oxygen saturation of red blood cells to 25% or less. As used herein, "reducing carbon dioxide" refers to reducing the carbon dioxide to 90 mmHg or less when measured at 37° C. An oxygen depleted blood product has an oxygen saturation of less than 25%, generally less than 10%, and can be about 5% SO2. A carbon dioxide depleted blood product is a blood product having a carbon dioxide level of below 20 mmHg when measured at 37° C.

As used herein, "blood product" includes whole blood or any component derived from whole blood including red blood cells, platelets, plasma, and white blood cells.

As used herein, "whole blood" includes white blood cells (WBCs), platelets suspended in plasma, and includes electrolytes, hormones, vitamins, antibodies, etc. In whole blood, white blood cells are normally present in the range of between 4.5 and $11.0 \times 10^9$ cells/L, and the normal RBC range at sea level is $4.6\text{-}6.2 \times 10^{12}$/L for men and $4.2\text{-}5.4 \times 10^{12}$/L for women. The normal hematocrit, or percent packed cell volume, is about 40-54% for men and about 38-47% for women. The platelet count is normally $150\text{-}450 \times 10^9$/L for both men and women. Whole blood is collected from a blood donor, and is usually combined with an anticoagulant. Whole blood, when collected is initially at about 37° C. and rapidly cools to about 30° C. during and shortly after collection, but slowly cools to ambient temperature over about 6 hours. Whole blood may be processed according to methods of the present disclosure at collection, beginning at 30-37° C., or at room temperature (typically about 25° C.).

As used herein, "red blood cells" (RBCs), stored red blood cells, oxygen reduced red blood cells, and oxygen and carbon dioxide reduced red blood cells, include RBCs present in whole blood, leukoreduced RBCs, platelet reduced RBCs, leukocyte and platelet reduced RBCs, and packed red blood cells (pRBCs). Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%. As used herein, oxygen reduced RBC (OR-RBC) can include oxygen and carbon dioxide reduced (OCR-) RBC (OCR-RBC)

As used herein, "leukoreduced whole blood" (LRWB) includes whole blood having an anticoagulant that has been treated to remove white blood cells and platelets, usually by filtration or centrifugation. Leukoreduced whole blood has levels of white blood cells that are reduced by at least 5 logs.

As used herein, "oxygen reduced leukoreduced whole blood" (OR-LRWB) can include oxygen and carbon dioxide reduced leukoreduced whole blood (OCR-LRWB).

As used herein, "leukoreduced packed red blood cells" (LRpRBC) includes packed red blood cells having oxygen reduced (OR-) whole blood that has been treated to remove white blood cells. As used herein, oxygen reduced leukoreduced packed red blood cells (OR-LRpRBC) can include oxygen and carbon dioxide reduced leukoreduced packed red blood cells (OCR-LRpRBC).

In accordance with aspects of the present specification, viruses reduced by the recited methods include enveloped viruses. In other aspects, the methods provide for reduction of non-enveloped viruses. In aspects of the present specification, viral pathogens that are reduced include one or more of the following: HIV-1, HIV-2, Hepatitis B virus (HBV), Hepatitis C virus (HCV), Human T lymphotropic virus I and II (HTLV-1 and -II), Cell-associated cytomegalovirus (CMV), Bovine viral diarrhea virus (BVDV), Duck hepatitis B virus (DHBV), Pseudorabies virus (PRV), West Nile virus, Human corona virus, Chikungunya virus, Influenza virus, Suid herpesvirus (SuHV-1), Vesicular stomatitis virus (VSV), Sindbis virus, Herpes simplex virus (HSV), Epstein-Barr virus (EBV), Porcine pseudorabies virus (PPRV), Pseudorabies virus (PRV), or Semliki forest virus (SLFV). In some aspects inactivated viruses include non-enveloped viruses comprising Bluetongue virus, Calicivirus, Human Adenovirus-5, Porcine parvovirus (PPV), Encephalomyocarditis virus (EMCV), Hepatitis A virus (HAV), Coxsackie virus, and Polio virus. It will be understood that the methods of viral parasite reduction include all viruses and are not limited to the ones recited above. One of ordinary skill in the art would recognize that the inactivation methods are directed to the genetic material of the various pathogens, while the oxygen reduction reduces, for example hemolysis of the red blood cell component of the blood product, and otherwise improves blood quality.

In aspects according to the present specification, the methods provide for reduced hemolysis and inactivation of parasites. In some aspects of the present specification inactivated parasites include Plasmodium falciparum (malaria), Trypanosoma cruzi (Chagas' disease), Leishmania mexicana, Leishmania major, leishmania infantum (leishmaniosis), Babesia microti, and Babesia divergens (babesiosis). In some aspects inactivated pathogenic bacteria can include *Bacillus cereus, Clostridium perfringens, Escherichia coli, Enterobacter cloacae, Klebsiella pneumoniae, Pseudomonas aeruginosa, Propionibacterium acnes, Serratia marcescens, Staphylococcus aureus, Staphylococcus epidermidis, Pseudomonas fluorescens, Listeria monocytogenes, Streptococcus pyogenes*, and *Acinetobacter baumannii*.

The methods of the present disclosure, provide for, and include, reducing hemolysis of red blood cells after pathogen treatment. Pathogen reduction methods applied to oxygen reduced blood or oxygen and carbon dioxide reduced blood result in significantly reduced levels of hemolysis. Pathogen reduction methods applied to oxygen reduced blood or oxygen and carbon dioxide reduced blood result in significantly reduced levels of microparticles. Incorporating an additional oxygen reduction step to pathogen reduction methods results in improvements to the quality of the stored blood leading to improved shelf life. Importantly, the application of blood oxygen reduction methods to existing methods of pathogen reduction results in significant improvements. Thus, the methods of the present specification can be applied to pathogen reduction methods known in the art. Suitable methods for pathogen removal compatible with reduced oxygen pathogen inactivation include, but are not limited to the methods discussed in Wagner et al., "Developing pathogen reduction technologies for RBC suspensions" in *Vox Sanguinis*, 100:112-121 (2011), Pidcoke et al., "Primary hemostatic capacity of whole blood: a comprehensive analysis of pathogen reduction and refrigeration effects over time" in *Transfusion,* 53:137-149 (2013), Henschler et al., "Development of the S-303 pathogen inactivation technology for red blood cell concentrates" in *Transfusion Medicine and Hemotherapy,* 38:33-42 (2011), Guignard et al., "The clinical and biological impact of new pathogen inactivation technologies on platelet concentrates" in Blood Reviews, 28: 235-241 (2014), Picker et al., "Current methods for the reduction of blood-borne pathogens: a comprehensive literature review" in *Blood Transfusion,* 11:343-348 (2014), Irsch et al., "Pathogen inactivation of platelet and plasma blood components for transfusion using the INTERCEPT Blood System™" in *Transfusion Medicine and Hemotherapy,* 38:19-31 (2010), and U.S. Pat. No. 5,120,659, issued Jun. 9, 1992, to King, et al.

The methods provide for reductions in hemolysis that provide for extending the allowable storage time after pathogen inactivation by maintaining the levels of hemolysis below 0.8% or, in certain aspects, below 1.0%. In an aspect, the hemolysis is no greater than 0.2% after 14 days of storage under anaerobic conditions. In an aspect, hemolysis is no greater than 0.4% after 21 days of storage under anaerobic conditions. In another aspect, hemolysis is no greater than 0.5% after 28 days of storage under anaerobic conditions. In a further aspect, hemolysis is no greater than 0.8% after 35 days of storage under anaerobic conditions. In other aspects, hemolysis is no greater than 0.8% after 42 days of storage under anaerobic conditions. In other aspects, hemolysis is no greater than 0.8% after 49 days of storage under anaerobic conditions. In some aspects, hemolysis is no greater than 1.0% after 35 days of storage under anaerobic conditions. In other aspects, hemolysis is no greater than 1.0% after 42 days of storage under anaerobic conditions. In other aspects, hemolysis is no greater than 1.0% after 49 days of storage under anaerobic conditions. In another aspect, the hemolysis is no greater than 0.1% after 14 days of storage under anaerobic conditions. In another aspect, the hemolysis is between 0.01 to 0.2% after 14 days of storage under anaerobic conditions. In an aspect, hemolysis is between 0.2 to 0.4% after 21 days of storage under anaerobic conditions. In an aspect, hemolysis is between 0.05 to 0.4% after 21 days of storage under anaerobic conditions. In another aspect, hemolysis is no greater than 0.6% after 28 days of storage under anaerobic conditions. In another aspect, hemolysis is between 0.1 to 0.4% after 28 days of storage under anaerobic conditions. In another aspect, hemolysis is between 0.1 to 0.5% after 28 days of storage under anaerobic conditions. In another aspect, hemolysis is no greater than 0.4% after 35 days of storage under anaerobic conditions. In another aspect, hemolysis is between 0.1 to 0.8% after 35 days of storage under anaerobic conditions. In another aspect, hemolysis is between 0.2 to 1.0% after 35 days of storage under anaerobic conditions. In another aspect, hemolysis is between 0.2 to 0.8% after 42 days of storage under anaerobic conditions. In another aspect, hemolysis is between 0.2 to 1.0% after 42 days of storage under anaerobic conditions. In another aspect, hemolysis is between 0.2 to 0.8% after 49 days of storage under anaerobic conditions. In another aspect, hemolysis is between 0.2 to 1.0% after 49 days of storage under anaerobic conditions. Methods of pathogen reduction using oxygen and carbon dioxide reduced blood products provide for the reductions in hemolysis as provided above.

As provided herein, the methods provide for reducing the level of hemolysis in pathogen treated oxygen reduced red blood cells when compared to non-oxygen reduced red blood cells. In an aspect, pathogen reduction under oxygen reduced conditions results in about 30% of the levels of hemolysis observed in pathogen reduction in non-oxygen reduced preparations. In an aspect, at least about 30% reduction is observed after 21 days of anaerobic storage. In an aspect, the about 30% reduction in hemolysis is observed at 35 days of anaerobic storage. In a further aspect, the about 30% reduction is observed at 42 days of anaerobic storage.

As provided herein, the methods provide for reducing the level of hemolysis in pathogen treated oxygen reduced leukoreduced whole blood (OR-LRWB) when compared to non-oxygen reduced leukoreduced whole blood (LRWB). In an aspect, pathogen reduction under oxygen reduced conditions results in about 30% of the levels of hemolysis observed in pathogen reduction in non-oxygen reduced preparations. In an aspect, at least about 30% reduction is observed after 21 days of anaerobic storage. In an aspect, the about 30% reduction in hemolysis is observed at 35 days of anaerobic storage. In a further aspect, the about 30% reduction is observed at 42 days of anaerobic storage.

In some aspects, the reduction of hemolysis when compared to conventional pathogen reduction methods is at least 20%. In an aspect, the at least 20% reduction is observed after 21 days of anaerobic storage. In an aspect, the at least 20% reduction in hemolysis is observed at 35 days of anaerobic storage. In a further aspect, the at least 20% reduction is observed at 42 days of anaerobic storage. In some aspects, the reduction of hemolysis when compared to conventional pathogen reduction methods is at least 25%. In an aspect, the at least 25% reduction is observed after 21 days of anaerobic storage. In another aspect, the at least 25% reduction is observed after 35 days of anaerobic storage. In a further aspect, the at least 25% reduction is observed after 42 days of anaerobic storage. In some aspects, the reduction of hemolysis when compared to conventional pathogen reduction methods is at least 35%. In an aspect, the at least 35% reduction is observed after 21 days of anaerobic storage. In another aspect, the at least 35% reduction is observed after 35 days of anaerobic storage. In a further aspect, the at least 35% reduction is observed after 42 days of anaerobic storage. In some aspects, the reduction of hemolysis when compared to conventional pathogen reduction methods is at least 40%. In an aspect, the at least 40% reduction is observed after 21 days of anaerobic storage. In another aspect, the at least 40% reduction is observed after 35 days of anaerobic storage. In a further aspect, the at least 40% reduction is observed after 42 days of anaerobic storage.

In some aspects, the reduction of hemolysis when compared to conventional pathogen reduction methods is at least 45%. In an aspect, the at least 45% reduction is observed after 21 days of anaerobic storage. In another aspect, the at least 45% reduction is observed after 35 days of anaerobic storage. In a further aspect, the at least 45% reduction is observed after 42 days of anaerobic storage. In some aspects, the reduction of hemolysis when compared to conventional pathogen reduction methods is at least 50%. In an aspect, the at least 50% reduction is observed after 21 days of anaerobic storage. In another aspect, the at least 50% reduction is observed after 35 days of anaerobic storage. In a further aspect, the at least 50% reduction is observed after 42 days of anaerobic storage.

As provided herein, the methods provide for reducing the level of hemolysis in pathogen treated oxygen and carbon dioxide reduced red blood cells when compared to non-oxygen reduced red blood cells. In an aspect, pathogen reduction under oxygen and carbon dioxide reduced conditions results in about 30% of the levels of hemolysis observed in pathogen reduction in non-oxygen and carbon dioxide reduced preparations. In an aspect, at least about 30% reduction is observed after 21 days of anaerobic storage. In an aspect, the about 30% reduction in hemolysis is observed at 35 days of anaerobic storage. In a further aspect, the about 30% reduction is observed at 42 days of anaerobic storage.

As provided herein, the methods provide for reducing the level of hemolysis in pathogen treated oxygen and carbon dioxide reduced leukoreduced whole blood (OR-LRWB) when compared to non-oxygen reduced leukoreduced whole blood (LRWB). In an aspect, pathogen reduction under oxygen and carbon dioxide reduced conditions results in about 30% of the levels of hemolysis observed in pathogen reduction in non-oxygen reduced preparations. In an aspect, at least about 30% reduction is observed after 21 days of anaerobic storage. In an aspect, the about 30% reduction in hemolysis is observed at 35 days of anaerobic storage. In a further aspect, the about 30% reduction is observed at 42 days of anaerobic storage.

In some aspects, the reduction of hemolysis in oxygen and carbon dioxide depleted blood products when compared to conventional pathogen reduction methods is at least 20%. In an aspect, the at least 20% reduction is observed is after 21 days of anaerobic storage. In an aspect, the at least 20% reduction in hemolysis is observed at 35 days of anaerobic storage. In a further aspect, the at least 20% reduction is observed at 42 days of anaerobic storage. In some aspects, the reduction of hemolysis when compared to conventional pathogen reduction methods is at least 25%. In an aspect, the at least 25% reduction is observed after 21 days of anaerobic storage. In another aspect, the at least 25% reduction is observed after 35 days of anaerobic storage. In a further aspect, the at least 25% reduction is observed after 42 days of anaerobic storage. In some aspects, the reduction of hemolysis when compared to conventional pathogen reduction methods is at least 35%. In an aspect, the at least 35% reduction is observed after 21 days of anaerobic storage. In another aspect, the at least 35% reduction is observed after 35 days of anaerobic storage. In a further aspect, the at least 35% reduction is observed after 42 days of anaerobic storage. In some aspects, the reduction of hemolysis when compared to conventional pathogen reduction methods is at least 40%. In an aspect, the at least 40% reduction is observed after 21 days of anaerobic storage. In another aspect, the at least 40% reduction is observed after 35 days of anaerobic storage. In a further aspect, the at least 40% reduction is observed after 42 days of anaerobic storage.

In some aspects, the reduction of hemolysis in oxygen and carbon dioxide depleted blood products, when compared to conventional pathogen reduction methods is at least 45%. In an aspect, the at least 45% reduction is observed after 21 days of anaerobic storage. In another aspect, the at least 45% reduction is observed after 35 days of anaerobic storage. In a further aspect, the at least 45% reduction is observed after 42 days of anaerobic storage. In some aspects, the reduction of hemolysis when compared to conventional pathogen reduction methods is at least 50%. In an aspect, the at least 50% reduction is observed after 21 days of anaerobic storage. In another aspect, the at least 50% reduction is observed after 35 days of anaerobic storage. In a further aspect, the at least 50% reduction is observed after 42 days of anaerobic storage.

Due to the improved health of the red blood cells as indicated by reduced hemolysis, by reducing the level of oxygen in the blood prior to pathogen inactivation, the safe storage period (e.g., shelf life) of a pathogen reduce blood product can be extended. Not to be limited by theory, it is thought that the safety and usefulness of a stored blood product is reflected in a number of measurable parameters. Among the parameters are the overall levels of hemolysis and the level of microparticles. Accordingly the reduced hemolysis and reduced microparticle formation observed using the methods of the present specification may reflect underlying improvements to red blood physiology that are uncharacterized or unknown.

Due to the improved initial health of the red blood cells provided by reducing the oxygen in blood before pathogen treatment, the present specification provides for, and includes, extending the safe storage period (e.g., shelf life) of a pathogen reduced blood product. As provided herein, the shelf life of a pathogen reduced blood product can be increased by a week or more. In an aspect the shelf life can be increased by two weeks. In other aspects, the shelf life can be increased by three weeks wherein the blood retains hemolysis levels below 0.8%.

As provided above, a variety of pathogen reduction methods provide for one of more photosensitizers to be added to the blood product prior to irradiation with one or more wavelengths of light. Table 1 presents a number of suitable photosensitizers. As used herein, photosensitizers include those that produce reactive products as well as photosensitizers that are themselves reactive (for example psoralen related photosensitizers).

TABLE 1

Pathogen reduction photosensitizers and methods

| Author | Blood Component | X-linker | X-linker Conc. (µl) | Radiant Exposure | Citation | Secondary Citation |
|---|---|---|---|---|---|---|
| Pidcoke | WB | Riboflavin | 50 | 80 J/mL @ 265-400nm; 6.2 J/cm$^2$ @ 265-400 nm | Transfusion 2013, Vol. 53, Supplement pp. 139S-149S | n/a |
| Irsch | PLT, Plasma | Amotosalen | 150 | 3 J/cm$^2$ UV-A | Transfus Med Hemother 201138:19-31 DOI: 10.1159/000323937 | Lin L, Dikeman R, Molini B, Lukehart SA, Lane R, Dupuis K, Metzel P, Corash L: Photochemical treatment of platelet concentrates with amotosalen and UVA inactivates a broad spectrum of patho-genic bacteria. Transfusion 2004; 44:1496-1504. |
| Picker | PLT | n/a | n/a | 0.2 J/cm$^2$ UV-C | Blood Trartsfus 2013; 11:343-8 DOI 10.2450/2013.0218-12 | Seltsam A, Müller TH. UVC irradiation for pathogen reduction of platelet concentrates and plasma. Transfus Med Hemother 2011;38: 43-54. |
| Picker | Plasma | Methylene Blue | 1 | 1.0 J/cm$^2$ UV-C followed by 180 J/cm$^2$ @ 590 nm | Blood Transfus 2013; 11:343-8 DOI 10.2450/2013.0218-12 | Sandler SG. The status of pathogen-reduced plasma. Transfus Apher Sci 2010; 43:393-9. |

TABLE 1-continued

Pathogen reduction photosensitizers and methods

| Author | Blood Component | X-linker | X-linker Conc. (μl) | Radiant Exposure | Citation | Secondary Citation |
|---|---|---|---|---|---|---|
| Wagner | RBC | Hypericin | 10 | 19.8 J/cm$^2$ @ 590 nm | Vox Sanguinis (2011) 100, 112-121 | Prince AM, Pascual D, Meraelo D, et al..: Strategies for evaluation of enveloped virus inactivation in RBC concentrates using hypericin. Photochem Photobiol 2000; 71:188-195 |
| Wagner | RBC | Hypericin | 2 | 15 J/cm$^2$ Fluor. light | Vox Sanguinis (2011) 100, 112-121 | " " |
| Wagner | RBC | Aluninum Phthalocyanine | 25 | 44 J/cm$^2$ Red light | Vox Sanguinis (2011) 100, 112-121 | Howorowitz B, Williams 13, Rywkin S, et al..: Inactivation of viruses in blood with aluminum phthalocyanine derivatives. Transfusion 1991; 31:102-108 |
| Wagner | RBC | Silicon Phthalocyanine | 2 | 45 J/cm$^2$ Red light | Vox Sanguinis (2011) 100, 112-121 | Ben-Hur E, Rywkin S, Rosenthal I, et al..: Virus inactivation in RBC concen-trates by photosensitization with phi-halocyanines: protection of RBCs by not of vesicular stomatitis virus with a water-soluble analogue of vitamin E. Transfusion 1995; 35:401-406 |
| Wagner | RBC | Silicon Phthalocyanine | 5 | 15 J/cm$^2$ @ 670 nm | Vox Sanguinis (2011) 100, 112-121 | B en-Hur E, Chan WS, Yim Z, et al..: Photochemical decontamination of red blood cell concentrates with the silicon phthalocyanine PC4 and red light. Dev Biol (Basel) 2000; 102:149-156 |
| Wagner | RBC | Phenothiazine MB dye | 5 | 3.2 J/cm$^2$ Fluor. light | Vox Sanguinis (2011) 100, 112-121 | Wagner SJ, Storry JR, Mallory DA, et al..: RBC membrane alterations associ-ated with virucidal methylene blue phototreatment. Transfusion 1992; 33:30-36 |
| Wagner | RBC | Phenothiazine DMMB dye | 4 | 13.5 J/cm$^2$ Fluor. light | Vox Sanguinis (2011) 100, 112-121 | Wagner SJ, Skripchenko A, Robinette D, et al..: Preservation of RBC properties after virucidal phototreatment with dimethylmethylene blue. Transfusion 1998; 38:729-737 |
| Wagner | RBC | Phenothiazine DMMB dye | 6 | 0.187 J/cm$^2$ @ 670 nm | Vox Sanguinis (2011) 100, 112-121 | Wagner S, Skripchenko A, Thompson-Montgomery D: Use of a flow-cell system to investigate virucidal dimeth-ylmethylene blue phototreatment in two RBC additive solutions. Transfusion 2002; 42:1200-1205 |
| Wagner | RBC | Thiopyrylium | 160 | 1.1 J/cm$^2$ Red light | Vox Sanguinis (2011) 100, 112-121 | Skripchenko A, Balch A, Mackin A, et al..: In vivo recovery and survival of RBCs after photodynamic treatment with thiopyrylium and red light using a canine model. Vox Sang 2007; 92:157-159 |
| Wagner | RBC | Thiazole Orange | 80 | 1.1 J/cm$^2$ Fluor. light | Vox Sanguinis (2011) 100, 112-121 | Skripchenko A, Wagner SJ, Thompson-Montgomery D, et al..: Thiazole orange, a DNA-binding photosensitizer with flexible structure, can inactivate patho-gens in red blood cell suspensions while maintaining RBC storage properties. Transfusion 2006; 46:213-219 |
| Henschler | RBC | S-303 | 200 | n/a | Transfus Med Hemother 2011;38:33-42 | Stassinopoulos A, Mababangloob RS, Dupuis KW, et al..: Bacterial inactivation in leukoreduced PRBC treated with HELINX☐. Transfusion 2000; 40 (Sup-pl):38S (abstract S139-0401) |

In aspects according to the present specification, the pathogen reduction methods may include one or more photosensitizers. In an aspect the photosensitizer is riboflavin. In one aspect of the present disclosure, the final concentration of riboflavin is between 40 to 60 μM. In another aspect, the final concentration of riboflavin is at least 40 μM. In another aspect, the final concentration of riboflavin is at most 60 μM. In another aspect, the final concentration of riboflavin is between 40 to 55 μM. In another aspect, the final concentration of riboflavin is between 45 to 55 μM. In a further aspect, the final concentration of riboflavin is between 50 to 60 μM. In an aspect, the final concentration of riboflavin is 50 μM.

The present disclosure provides for and includes irradiating oxygen reduced blood products having an added photosensitizer to reduce pathogens levels. As used herein, the term "irradiation" is refers to illumination of blood using both visible and ultraviolet wavelengths.

In one aspect of the present disclosure, an oxygen reduced blood product having riboflavin is irradiated between 265 to 400 nm. In another aspect, a blood product is irradiated between 300 to 400 nm. In another aspect, a blood product is irradiated between 265 to 350 nm. Suitable wavelengths for the irradiation of an oxygen reduced blood product are determined based on the photosensitizer, for example as provided in Table 1. As provided by the present specification, the reduction in oxygen levels results in decreased hemolysis and decreased microparticle formation that normally result from the pathogen reduction process and reflects the improved health of the red blood cells in the pathogen inactivated blood products.

The present specification provides for, and includes, irradiating the oxygen reduced blood product having riboflavin with a UV radiant exposure f between 3.2 to 7.0 J/cm². In another aspect, oxygen reduced whole blood containing riboflavin is irradiated with a UV radiant exposure of between 5 to 7.0 J/cm². In another aspect, oxygen reduced whole blood containing riboflavin is irradiated with a UV radiant exposure of between 5 to 6.0 J/cm². In another aspect, oxygen reduced whole blood containing riboflavin is irradiated with a UV radiant exposure of between 4 to 7.0 J/cm². In another aspect, oxygen reduced whole blood containing riboflavin is irradiated with a UV radiant exposure of at least 3.2 J/cm². In another aspect, oxygen reduced whole blood containing riboflavin is irradiated with a UV radiant exposure of at least 5 J/cm². In a further aspect, oxygen reduced whole blood containing riboflavin is irradiated with a UV radiant exposure of at most 7.0 J/cm². The present disclosure provides for, and included, total dosages of up to 100 J/mL. In an aspect, the dosage is between 10 and 100 J/mL. In another aspect, the dosage is between 50 and 100 J/mL. In another aspect, the dosage is between 50 and 80 J/mL. In other aspect, the dosage is less than 150 J/mL. In an aspect, the dosage is at least 25 J/mL. Other suitable dosages can be determined, The present specification provides for, and includes, a method of pathogen inactivation that reduces the level of microparticles in stored blood. In aspects according to the present specification, the method comprises obtaining an oxygen reduced blood product, adding a photosensitizer, and irradiating said photosensitizer containing oxygen reduced blood product. In certain aspects, the method further includes storing the irradiated photosensitizer containing oxygen reduced blood product for a storage period. In other aspects, the irradiated photosensitizer containing oxygen reduced blood product is stored under anaerobic conditions for a storage period.

As provided herein, the storage period may be up to 9 weeks under either aerobic or anaerobic conditions and provides for reduced microparticle formation. In an aspect, the storage period under either aerobic or anaerobic conditions is 2 weeks. In another aspect, the storage period under either aerobic or anaerobic conditions is 3 weeks. In a further aspect, the storage period under either aerobic or anaerobic conditions is 3 weeks. The present methods further provide for storage periods under either aerobic or anaerobic conditions of 4 weeks. In other aspects, the storage period following pathogen inactivation may be 5 weeks. In yet other aspects, the aerobic or anaerobic storage period is 6 weeks. In an additional aspect, the aerobic or anaerobic storage period is 6 weeks. Notably, as the storage period is extended, the observed improvement in blood cell quality increases. Not to be limited by theory, it is thought that the reduction in microparticle formation is the result of improved red blood cell quality that is immediate. That is, the red blood cell quality is improved prior to storage and the decreased microparticle formation is evidence of that improvement. It is believed that other, uncharacterized changes in the red blood cells, may underlie the observed microparticle reduction.

In aspects according to the present specification, the pathogen reduction methods providing for reduced microparticle formation may include one or more photosensitizers. In an aspect the photosensitizer is riboflavin. In one aspect of the present disclosure, the final concentration of riboflavin is between 40 to 60 µM. In another aspect, the final concentration of riboflavin is at least 40 µM. In another aspect, the final concentration of riboflavin is at most 60 µM. In another aspect, the final concentration of riboflavin is between 40 to 55 µM. In another aspect, the final concentration of riboflavin is between 45 to 55 µM. In a further aspect, the final concentration of riboflavin is between 50 to 60 µM. In an aspect, the final concentration of riboflavin is 50 µM.

The present disclosure provides for and includes irradiating oxygen reduced blood products having an added photosensitizer to reduce pathogens levels and reduce microparticle formation. As used herein, the term "irradiation" is refers to illumination of blood using both visible and ultraviolet wavelengths.

In one aspect of the present disclosure, an oxygen reduced blood product having riboflavin is irradiated between 265 to 400 nm to result in reduced microparticle formation. In another aspect, a blood product is irradiated between 300 to 400 nm. In another aspect, a blood product is irradiated between 265 to 350 nm. Suitable wavelengths for the irradiation of an oxygen reduced blood product are determined based on the photosensitizer, for example as provided in Table 1. As provided by the present specification, the reduction in oxygen levels results in decreased microparticle formation that normally result from the pathogen reduction process and reflects the improved health of the red blood cells in the pathogen inactivated blood products.

Reductions in microparticle formation can be measured by methods known in the art. Suitable methods for microparticle formation include Schubert et al. (Schubert, et al., "Whole blood treated with riboflavin and ultraviolet light: Quality assessment of all blood components produced by the buffy coat method," Transfusion 55(4):815-823 (2015)). While absolute values of the numbers of microparticles can be determined, in general, the reduction of microparticles is determined relative to a control sample. In the present specification, the control comprises a non-oxygen reduced blood product. Absolute values may be determined by preparing a set of standards.

The methods of the present specification provide for reductions in microparticle formation in stored blood. In some aspects, the stored blood is stored under anaerobic conditions, thus maintaining the oxygen reduced state obtained for the pathogen inactivation process. In other aspects, the stored blood is maintained under conventional storage conditions. Though conventional storage conditions allow for the ingress of oxygen over time and diminishes the improvements to ATP and 2,3-DPG for example, conventional storage may decrease costs and reduce disruption to existing blood banking facilities. In most aspects however, it is expected that storage would occur under anaerobic conditions, either with or without carbon dioxide.

As provided herein, microparticle formation is decreased by reducing oxygen to 25% SO2 or below before completing the pathogen inactivation methods. In an aspect, the microparticles are reduced by about two-fold in oxygen reduced samples compared to equivalently treated aerobic samples after 2 days. The methods further provide for at least two-fold reductions in microparticles after one week. In an aspect, the level of microparticles is reduced by greater than five-fold after two weeks of storage. In an aspect, microparticles are reduced by 9-fold after 3 weeks storage. In a further aspect, the number of microparticles is reduced by 9-fold after 6 weeks of storage. The present methods provide for at least a two-fold reduction in microparticle formation after 9 weeks of storage under anaerobic conditions. In other aspects, the methods provide for at least a two-fold reduction in microparticle formation after 9 weeks of storage under aerobic conditions.

Also provided by the present methods are reductions in microparticle formation of at least three fold when compared to pathogen reduction methods performed in the presence of oxygen. When measured at two to 6 weeks, the level of microparticles remains at least three fold less compared to similarly treated oxygen containing samples. In other aspects, the reduced microparticle formation results in at least a five-fold reduction after two weeks of storage.

In aspects of the present specification, the level of microparticle formation are reduced to levels of non-pathogen treated samples. Accordingly, using the methods of the present specification, the increase in microparticle formation that results from pathogen inactivation are reversed.

The present specification provides for, and includes, improved blood compositions that have extended shelf lives. In an aspect, the present disclosure provides for and includes, oxygen reduced whole blood comprising whole blood collected in CPD, having between 40 to 60 µM riboflavin, having an oxygen saturation (SO2) of from 1 to 25%, and having a pCO2 of 90 mmHg or less at 37° C., wherein said oxygen reduced whole blood has been irradiated with UV light between 265 to 400 nm.

In aspects according to the present specification, oxygen reduced whole blood comprising whole blood having an oxygen saturation (SO2) of less than 25% may have an SO2 of less than 20%. In other aspects, the riboflavin containing pathogen reduced blood may have an SO2 of less than 15%. In an aspect, the SO2 level in the riboflavin containing oxygen reduced blood products may have an SO2 of less than 10%. In certain aspects, the riboflavin containing pathogen reduced blood may have an SO2 of 5%. The present specification further provides for oxygen reduced whole blood having an SO2 of between 5 and 20%. In another aspect, the SO2 may be between 5 and 25%. In another aspect, the SO2 may be between 5 and 15%. In a further aspect, the SO2 is reduced to between 5 and 10%.

In aspects according to the present specification, oxygen reduced whole blood containing riboflavin is irradiated with a UV dosage of between 3.2 to 7.0 J/cm$^2$. In another aspect, oxygen reduced whole blood containing riboflavin is irradiated with a UV dosage of between 5 to 7.0 J/cm$^2$. In another aspect, oxygen reduced whole blood containing riboflavin is irradiated with a UV dosage of between 5 to 6.0 J/cm$^2$. In another aspect, oxygen reduced whole blood containing riboflavin is irradiated with a UV dosage of between 4 to 7.0 J/cm$^2$. In another aspect, oxygen reduced whole blood containing riboflavin is irradiated with a UV dosage of at least 3.2 J/cm$^2$. In another aspect, oxygen reduced whole blood containing riboflavin is irradiated with a UV dosage of at least 5 J/cm$^2$. In a further aspect, oxygen reduced whole blood containing riboflavin is irradiated with a UV dosage of at most 7.0 J/cm$^2$.

The present specification provides for, and includes, improved blood compositions that have extended shelf lives. In an aspect, the present disclosure provides for and includes, oxygen and carbon dioxide reduced whole blood comprising whole blood collected in CPD, having between 40 to 60 µM riboflavin, having an oxygen saturation (SO2) of from 1 to 25%, and having a pCO2 of 20 mmHg or less at 37° C., wherein said oxygen reduced whole blood has been irradiated with UV light between 265 to 400 nm. In another aspect, the oxygen and carbon dioxide reduced whole blood comprising whole blood collected in CPD, having between 40 to 60 µM riboflavin, having an oxygen saturation (SO2) of from 1 to 25%, and having a pCO2 of between 20 and 40 mmHg at 37° C., wherein said oxygen reduced whole blood has been irradiated with UV light between 265 to 400 nm. In another aspect, the oxygen and carbon dioxide reduced whole blood comprising whole blood collected in CPD, having between 40 to 60 µM riboflavin, having an oxygen saturation (SO2) of from 1 to 25%, and having a pCO2 of between 40 and 70 mmHg at 37° C., wherein said oxygen reduced whole blood has been irradiated with UV light between 265 to 400 nm. In another aspect, the oxygen and carbon dioxide reduced whole blood comprising whole blood collected in CPD, having between 40 to 60 µM riboflavin, having an oxygen saturation (SO2) of from 1 to 25%, and having a pCO2 of between 10 and 20 mmHg at 37° C., wherein said oxygen reduced whole blood has been irradiated with UV light between 265 to 400 nm. In another aspect, the oxygen and carbon dioxide reduced whole blood comprising whole blood collected in CPD, having between 40 to 60 µM riboflavin, having an oxygen saturation (SO2) of from 1 to 25%, and having a pCO2 of less than 15 mmHg at 37° C., wherein said oxygen reduced whole blood has been irradiated with UV light between 265 to 400 nm.

The methods of the present specification provide for and include improvement in parameters selected from the group comprising complete blood count (CBC), concentration of residual pathogen, percent hemolysis, ATP, 2,3-DPG, deformability, microparticles formation, phosphatidylserine exposure on the cell membrane surface, % SO2, and decomposition kinetics of S-303, and a combination thereof in stored blood when compared to pathogen reduction methods performed in the presence of oxygen. In some aspects, the stored blood is stored under anaerobic conditions, thus maintaining the oxygen reduced state obtained for the pathogen inactivation process. In other aspects, the stored blood is maintained under conventional storage conditions. Though conventional storage conditions allow for the ingress of oxygen over time and diminishes the improvements to ATP and 2,3-DPG for example, conventional storage may decrease costs and reduce disruption to existing blood banking facilities. In most aspects however, it is expected that storage would occur under anaerobic conditions, either with or without carbon dioxide.

The methods of the present specification provide for reductions in hemolysis of a blood product comprising removing oxygen from a blood product, adding S-303 to a final concentration of 0.2 mM, and adding GSH to a final concentration of between 2 to 20 mM. In another aspect, the reduction of hemolysis comprises removing oxygen from a blood product, adding S-303 to a final concentration of 0.2 mM, and adding GSH to a final concentration of between 5 to 10 mM. In other aspects, the reduction of hemolysis comprises removing oxygen and carbon dioxide from a blood product, adding S-303 to a final concentration of 0.2 mM, and adding GSH to a final concentration of between 2 to 20 mM. In a further aspect, reductions in hemolysis comprises removing oxygen from a blood product, adding S-303 to a final concentration of 0.2 mM, adding GSH to a final concentration of between 2 to 20 mM, and storing under anaerobic conditions. In yet another aspect, reduction of hemolysis of a blood product comprises mixing an additive solution with the blood product, removing oxygen from a blood product, adding S-303 to a final concentration of 0.2 mM, adding GSH to a final concentration of between 2 to 20 mM, and storing under anaerobic conditions. The methods of the present specification also provide for reductions in hemolysis in S-303 pathogen inactivated and oxygen reduced blood products, by maintaining the levels of hemolysis below 1.0%. In an aspect, hemolysis is below 0.8%. In another aspect, hemolysis is no greater than 0.2%. In a further aspect, hemolysis is no greater than 0.4%. In yet another aspect, hemolysis is no greater than 0.6%. In another aspect, hemolysis is between 0.01 to 0.2%. In certain aspects, hemolysis is between 0.2 and 0.8%. In other aspects, hemolysis is between 0.2 and 0.6%. In another aspect, hemolysis is between 0.5 and 1.0%.

The methods of the present specification provide for having reduced microparticle formation of a blood product comprising removing oxygen from a blood product, adding S-303 to a final concentration of 0.2 mM, and adding GSH to a final concentration of between 2 to 20 mM. In another aspect, the reduction in microparticle formation comprises removing oxygen from a blood product, adding S-303 to a final concentration of 0.2 mM, and adding GSH to a final concentration of between 2 to 10 mM. In other aspects, the reduction in microparticle formation comprises removing oxygen and carbon dioxide from a blood product, adding S-303 to a final concentration of 0.2 mM, and adding GSH to a final concentration of between 2 to 20 mM. In a further aspect, reduction in microparticle formation comprises removing oxygen from a blood product, adding S-303 to a final concentration of 0.2 mM, adding GSH to a final concentration of between 2 to 20 mM, and storing under anaerobic conditions. In yet another aspect, reduction in microparticle formation of a blood product comprises mixing an additive solution with the blood product, removing oxygen from a blood product, adding S-303 to a final concentration of 0.2 mM, adding GSH to a final concentration of between 2 to 20 mM, and storing under anaerobic conditions. In a further aspect, reduction in microparticle formation of a blood product comprises mixing an additive solution with the blood product, removing oxygen from a blood product, adding S-303 to a final concentration of 0.2 mM, adding GSH to a final concentration of between 2 to 20 mM, centrifuging the blood product. and storing under anaerobic conditions. The methods of the present specification also provide for reductions in microparticle formation in S-303 pathogen inactivated and oxygen reduced blood products, by reducing the level of microparticles by greater than five-fold after at least one week of storage. In an aspect, the level of microparticles is reduced by greater than four-fold after at least one week of storage. In another aspect, the level of microparticles is reduced by greater than three-fold after at least one week of storage. In yet another aspect, the level of microparticles is reduced by greater than two-fold after at least one week of storage. In an aspect, the level of microparticles is reduced by greater than 10% after at least one week of storage. In another aspect, the level of microparticles is reduced by greater than 25% after at least one week of storage. In a further aspect, the level of microparticles is reduced by between 10 and 50% after at least one week of storage. In another aspect, the level of microparticles is reduced by between 20 and 60% after at least one week of storage. In a further aspect, the level of microparticles is reduced by greater than 60% after at least one week of storage. In an aspect, the level of microparticles is reduced by between 60 and 90% after at least one week of storage. In another aspect, the level of microparticles is reduced by between 90 and 100% after at least one week of storage. In another aspect, the level of microparticles is reduced by greater than 80% after at least one week of storage. The methods of the present specification also provide for reductions in microparticle formation in S-303 pathogen inactivated and oxygen reduced blood products, by reducing the level of microparticles by greater than five-fold after at least three weeks of storage. In an aspect, the level of microparticles is reduced by greater than four-fold after at least three weeks of storage. In another aspect, the level of microparticles is reduced by greater than three-fold after at least three weeks of storage. In yet another aspect, the level of microparticles is reduced by greater than two-fold after at least three weeks of storage. In an aspect, the level of microparticles is reduced by greater than 10% after at least three weeks of storage. In another aspect, the level of microparticles is reduced by greater than 25% after at least three weeks of storage. In a further aspect, the level of microparticles is reduced by between 10 and 50% after at least three weeks of storage. In another aspect, the level of microparticles is reduced by between 20 and 60% after at least three weeks of storage. In a further aspect, the level of microparticles is reduced by greater than 60% after at least three weeks of storage. In an aspect, the level of microparticles is reduced by between 60 and 90% after at least three weeks of storage. In another aspect, the level of microparticles is reduced by between 90 and 100% after at least three weeks of storage. In another aspect, the level of microparticles is reduced by greater than 80% after at least three weeks of storage. The methods of the present specification also provide for reductions in microparticle formation in S-303 pathogen inactivated and oxygen reduced blood products, by reducing the level of microparticles by greater than five-fold after three weeks of storage. In an aspect, the level of microparticles is reduced by greater than four-fold after three weeks of storage. In another aspect, the level of microparticles is reduced by greater than three-fold after three weeks of storage. In yet another aspect, the level of microparticles is reduced by greater than two-fold after three weeks of storage. In an aspect, the level of microparticles is reduced by greater than 10% after three weeks of storage. In another aspect, the level of microparticles is reduced by greater than 25% after three weeks of storage. In a further aspect, the level of microparticles is reduced by between 10 and 50% after three weeks of storage. In another aspect, the level of microparticles is reduced by between 20 and 60% after three weeks of storage. In a further aspect, the level of microparticles is reduced by greater than 60% after three weeks of storage. In an aspect, the level of microparticles is reduced by between 60 and 90% after three weeks of storage. In another aspect, the level of microparticles is reduced by between 90 and 100% after three weeks of storage. In another aspect, the level of microparticles is reduced by greater than 80% after three weeks of storage. The methods of the present specification also provide for reductions in microparticle formation in S-303 pathogen inactivated and oxygen reduced blood products, by reducing the level of microparticles by greater than five-fold after at least six weeks of storage. In an aspect, the level of microparticles is reduced by greater than four-fold after at least six weeks of storage. In another aspect, the level of microparticles is reduced by greater than three-fold after at least six weeks of storage. In yet another aspect, the level of microparticles is reduced by greater than two-fold after at least six weeks of storage. In an aspect, the level of microparticles is reduced by greater than 10% after at least six weeks of storage. In another aspect, the level of microparticles is reduced by greater than 25% after at least six weeks of storage. In a further aspect, the level of microparticles is reduced by between 10 and 50% after at least three weeks of storage. In another aspect, the level of microparticles is reduced by between 20 and 60% after at least six weeks of storage. In a further aspect, the level of microparticles is reduced by greater than 60% after at least six weeks of storage. In an aspect, the level of microparticles is reduced by between 60 and 90% after at least six weeks of storage. In another aspect, the level of microparticles is reduced by between 90 and 100% after at least six weeks of storage. In another aspect, the level of microparticles is reduced by greater than 80% after at least six weeks of storage.

The present specification provides for, and includes, improved blood compositions that have extended shelf lives. In an aspect, the present disclosure provides for and includes, oxygen reduced red blood cells comprising red blood cells having a final concentration of approximately 0.2 mM S-303, having an oxygen saturation (SO2) of less than 25%, and having a pCO2 of 90 mmHg or less at 37° C. In another aspect, oxygen reduced red blood cells comprising red blood cells having a final concentration of approximately 0.2 mM S-303 and a final concentration of between approximately 5 to 20 mM GSH. In an aspect, the oxygen reduced red blood cells are also carbon dioxide reduced red blood cells comprising red blood cells having a final concentration of approximately 0.2 mM S-303, having an oxygen saturation (SO2) of less than 25%, and having a pCO2 of 90 mmHg or less at 37° C. In another aspect, oxygen and carbon dioxide reduced red blood cells comprise red blood cells having a final concentration of approximately 0.2 mM S-303 and a final concentration of between approximately 2 to 20 mM GSH. The present specification also provides for, and includes, improved blood compositions having improvement in at least one, at least two, at least three, at least four, or at least five, parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303. In an aspect, the improved blood compositions have improvement in two parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303. In another aspect, the improved blood compositions have improvement in three parameters selected from the group consisting of CBC, concentration of residual pathogen, percent homolysis, ATP, 2,3-DPG, deformability, microparticles formation, phosphatidylserine exposure on the cell membrane surface, % SO2, and decomposition kinetics of S-303. In a further aspect, the improved blood compositions have improvement in three parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303. In yet another aspect, the improved blood compositions have improvement in four parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303. In another aspect, the improved blood compositions have improvement in five parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303. In another aspect, the improved blood compositions have improvement in between five to nine parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303.

The present specification provides for S-303 pathogen inactivated and oxygen reduced improved blood compositions having an improved concentration of residual pathogens by reducing the level of pathogens by greater than 10%. In certain aspects, the concentration of residual pathogens is reduced by greater than 20%. In other aspects, the concentration of residual pathogens is reduced by 30%. In another aspect, the concentration of residual pathogens is reduced by greater than 40%. In yet another aspect, the concentration of residual pathogens is reduced by greater than 60%. In a further aspect, the concentration of residual pathogens is reduced by greater than 80%. In certain aspects, the concentration of residual pathogens is reduced by between 10 to 50%. In other aspects, the concentration of residual pathogens is reduced by between 50 to 95%. In another aspect, the concentration of residual pathogens is reduced by between 60 to 100%. In some aspects, the present specification provides for S-303 pathogen inactivated and oxygen reduced improved blood compositions having an improved concentration of residual pathogens by also having reduced carbon dioxide.

The present specification provides for S-303 pathogen inactivated and oxygen reduced improved blood compositions having levels of hemolysis is below 1.0%. In an aspect, hemolysis is below 0.8%. In another aspect, hemolysis is no greater than 0.2%. In a further aspect, hemolysis is no greater than 0.4%. In yet another aspect, hemolysis is no greater than 0.6%. In another aspect, hemolysis is between 0.01 to 0.2%. In certain aspects, hemolysis is between 0.2 and 0.8%. In other aspects, hemolysis is between 0.2 and 0.6%. In another aspect, hemolysis is between 0.5 and 1.0%. In some aspects, the present specification provides for S-303 pathogen inactivated and oxygen reduced improved blood compositions having improved hemolysis by also having reduced carbon dioxide.

The present specification provides for S-303 pathogen inactivated and oxygen reduced improved blood compositions having improved deformability. In certain aspects, deformability is increased by greater than 5%. In other aspects, deformability is increased by greater than 10%. In another aspect, deformability is increased by between 10 to 50%. In other aspects, deformability is increased by greater than 50%. In some aspects, the present specification provides for S-303 pathogen inactivated and oxygen reduced improved blood compositions having improved deformability by also having reduced carbon dioxide.

The present specification provides for S-303 pathogen inactivated and oxygen reduced improved blood compositions having improved levels of ATP by having increased levels of ATP. In certain aspects, the level of ATP is increased by greater than 10%. In other aspects, the level of ATP is increased by between 5 to 40%. In another aspect, the level of ATP is increased after one week of storage. In other aspects, the level of ATP is increased after two weeks of storage. In another aspect, the level of ATP is increased after four weeks of storage. In yet another aspect, the level of ATP is increased after five weeks of storage. In a further aspect, the level of ATP is increased after 6 weeks of storage. In some aspects, the present specification provides for S-303 pathogen inactivated and oxygen reduced improved blood compositions having an improved level of ATP by also having reduced carbon dioxide.

The present specification provides for S-303 pathogen inactivated and oxygen reduced improved blood compositions having improved levels of 2,3-DPG by having increased levels of 2,3-DPG. In certain aspects, the level of 2,3-DPG is increased by greater than 10%. In other aspects, the level of 2,3-DPG is increased by greater than 20%. In further aspects, the level of 2,3-DPG is increased by greater than 30%. In other aspects, the level of 2,3-DPG is increased by between 5 to 40%. In another aspect, the level of 2,3-DPG is increased after one week of storage. In other aspects, the level of 2,3-DPG is increased after two weeks of storage. In another aspect, the level of 2,3-DPG is increased after four weeks of storage. In yet another aspect, the level of 2,3-DPG is increased after five weeks of storage. In a further aspect, the level of 2,3-DPG is increased after 6 weeks of storage. In some aspects, the present specification provides for S-303 pathogen inactivated and oxygen reduced improved blood compositions having an improved level of 2,3-DPG by also having reduced carbon dioxide.

The present specification provides for S-303 pathogen inactivated and oxygen reduced improved blood compositions having improved levels of microparticles by reducing the levels of microparticles by five-fold after at least one week of storage. In an aspect, the level of microparticles is reduced by greater than four-fold after at least one week of storage. In another aspect, the level of microparticles is reduced by greater than three-fold after at least one week of storage. In yet another aspect, the level of microparticles is reduced by greater than two-fold after at least one week of storage. In an aspect, the level of microparticles is reduced by greater than 10% after at least one week of storage. In another aspect, the level of microparticles is reduced by greater than 25% after at least one week of storage. In a further aspect, the level of microparticles is reduced by between 10 and 50% after at least one week of storage. In another aspect, the level of microparticles is reduced by between 20 and 60% after at least one week of storage. In a further aspect, the level of microparticles is reduced by greater than 60% after at least one week of storage. In an aspect, the level of microparticles is reduced by between 60 and 90% after at least one week of storage. In another aspect, the level of microparticles is reduced by between 90 and 100% after at least one week of storage. In another aspect, the level of microparticles is reduced by greater than 80% after at least one week of storage. In an aspect, the level of microparticles is reduced by greater than 10% after at least three weeks of storage. In another aspect, the level of microparticles is reduced by greater than 25% after at least three weeks of storage. In a further aspect, the level of microparticles is reduced by between 10 and 50% after at least three weeks of storage. In another aspect, the level of microparticles is reduced by between 20 and 60% after at least three weeks of storage. In a further aspect, the level of microparticles is reduced by greater than 60% after at least three weeks of storage. In an aspect, the level of microparticles is reduced by between 60 and 90% after at least three weeks of storage. In another aspect, the level of microparticles is reduced by between 90 and 100% after at least three weeks of storage. In another aspect, the level of microparticles is reduced by greater than 80% after at least three weeks of storage. In an aspect, the level of microparticles is reduced by greater than 10% after at least six weeks of storage. In another aspect, the level of microparticles is reduced by greater than 25% after at least six weeks of storage. In a further aspect, the level of microparticles is reduced by between 10 and 50% after at least six weeks of storage. In another aspect, the level of microparticles is reduced by between 20 and 60% after at least six weeks of storage. In a further aspect, the level of microparticles is reduced by greater than 60% after at least six weeks of storage. In an aspect, the level of microparticles is reduced by between 60 and 90% after at least six weeks of storage. In another aspect, the level of microparticles is reduced by between 90 and 100% after at least six weeks of storage. In another aspect, the level of microparticles is reduced by greater than 80% after at least six weeks of storage. In some aspects, the present specification provides for S-303 pathogen inactivated and oxygen reduced improved blood compositions having improved levels of microparticles by also having reduced carbon dioxide.

The present specification also provides for S-303 pathogen inactivated and oxygen reduced improved blood compositions having improved phosphatidylserine exposure on the cell membrane surface by maintaining asymmetrical distribution of phosphatidylserine along the cytosolic surface of the cell membrane. In certain aspects, phosphatidylserine expression can be measured through labeling cell membrane with fluorescent annexin-V and quantifying with flow cytometry or microscopy. In some aspects, the present specification provides for S-303 pathogen inactivated and oxygen reduced improved blood compositions also having reduced carbon dioxide.

The present specification provides for S-303 pathogen inactivated and oxygen reduced improved blood compositions having improved levels of % SO2 by having a % SO2 of less than 30%. In an aspect, the % SO2 is less than 25%. In another aspect, the % SO2 is less than 20%. In yet another aspect, the % SO2 is less than 20%. In a further aspect, the % SO2 is less than 10%. In another aspect, the % SO2 is less than 5%. In certain aspects, the % SO2 is between 5 to 20%. In other aspects, the % SO2 is between 3 to 15%. In some aspects, the present specification provides for S-303 pathogen inactivated and oxygen reduced improved blood compositions also having reduced carbon dioxide.

The present specification provides for S-303 pathogen inactivated and oxygen reduced improved blood compositions having reduced levels of S-303 after the pathogen inactivation process of 3 hrs. In an aspect, the levels of S-303 are reduced after the pathogen inactivation process of 6 hrs. In another aspect, the levels of S-303 are reduced after the pathogen inactivation process of 9 hrs. In yet another aspect, the levels of S-303 are reduced after the pathogen inactivation process of 12 hrs. In a further aspect, the levels of S-303 are reduced after the pathogen inactivation process of 24 hrs. In some aspects, the present specification provides for S-303 pathogen inactivated and oxygen reduced improved blood compositions also having reduced carbon dioxide.

The methods of the present specification provide for improving the efficacy of pathogen inactivation of S-303 in a blood product comprising removing oxygen from red blood cells, adding S-303 to a final concentration of 0.2 mM, and adding GSH to a final concentration of between 2 to 20 mM. In another aspect, the improvement to the efficacy of pathogen inactivation of S-303 in a blood product comprises removing oxygen from a blood product, adding S-303 to a final concentration of 0.2 mM, and adding GSH to a final concentration of between 2 to 10 mM. In other aspects, the improvement to the efficacy of pathogen inactivation of S-303 in a blood product comprises removing oxygen and carbon dioxide from a blood product, adding S-303 to a final concentration of 0.2 mM, and adding GSH to a final concentration of between 2 to 20 mM. In a further aspect, the improvement to the efficacy of pathogen inactivation of S-303 in a blood product comprises removing oxygen from a blood product, adding S-303 to a final concentration of 0.2 mM, adding GSH to a final concentration of between 2 to 20 mM, and storing under anaerobic conditions. In yet another aspect, the improvement to the efficacy of pathogen inactivation of S-303 in red blood cells comprises mixing an additive solution with the blood product, removing oxygen from a blood product, adding S-303 to a final concentration of 0.2 mM, adding GSH to a final concentration of between 2 to 20 mM, and storing under anaerobic conditions. In certain aspects, the improvement to the efficacy of pathogen inactivation of S-303 is by reducing the concentration of residual pathogens by greater than 10%. In certain aspects, the concentration of residual pathogens is reduced by greater than 20%. In other aspects, the concentration of residual pathogens is reduced by 30%. In another aspect, the concentration of residual pathogens is reduced by greater than 40%. In yet another aspect, the concentration of residual pathogens is reduced by greater than 60%. In a further aspect, the concentration of residual pathogens is reduced by greater than 80%. In certain aspects, the concentration of residual pathogens is reduced by between 10 to 50%. In other aspects, the concentration of residual pathogens is reduced by between 50 to 95%. In another aspect, the concentration of residual pathogens is reduced by between 60 to 100%.

In a further aspect, reduction in microparticle formation of a blood product comprises mixing an additive solution with the blood product, removing oxygen from a blood product, adding S-303 to a final concentration of 0.2 mM, adding GSH to a final concentration of between 2 to 20 mM, centrifuging the blood product, and storing under anaerobic conditions. In certain aspects, the reduction in microparticle formation in a blood product comprises reducing the levels of microparticles by five-fold after at least one week of storage. In an aspect, the level of microparticles is reduced by greater than four-fold after at least one week of storage. In another aspect, the level of microparticles is reduced by greater than three-fold after at least one week of storage. In yet another aspect, the level of microparticles is reduced by greater than two-fold after at least one week of storage. In an aspect, the level of microparticles is reduced by greater than 10% after at least one week of storage. In another aspect, the level of microparticles is reduced by greater than 25% after at least one week of storage. In a further aspect, the level of microparticles is reduced by between 10 and 50% after at least one week of storage. In another aspect, the level of microparticles is reduced by between 20 and 60% after at least one week of storage.

The present specification provides for S-303 pathogen inactivated and oxygen reduced blood compositions having improved parameters selected from the group consisting of CBC, concentration of residual pathogen, percent hemolysis, ATP, 2,3-DPG, deformability, microparticles formation, phosphatidylserine exposure on the cell membrane surface, % SO2, and decomposition kinetics of S-303 in stored blood when compared to a pooled sample of blood. In certain aspects, the improvements in CBC, concentration of residual pathogen, percent hemolysis, ATP, 2,3-DPG, deformability, microparticles formation, phosphatidylserine exposure on the cell membrane surface, % SO2, and decomposition kinetics of S-303 in stored blood are as described above.

The present specification provides for units of S-303 pathogen inactivated and oxygen reduced blood having improved parameters selected from the group comprising CBC, concentration of residual pathogen, percent hemolysis, ATP, 2,3-DPG, deformability, microparticles formation, phosphatidylserine exposure on the cell membrane surface, % SO2, and decomposition kinetics of S-303 in stored blood when compared to units of blood having pathogen reduction methods performed in the presence of oxygen.

The terms "comprises," "comprising," "includes," "including," "having," and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" may include a plurality of compounds, including mixtures thereof.

While the present disclosure has been described with reference to particular aspects, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular aspects disclosed as the best mode contemplated for carrying out the present disclosure, but that the present disclosure will include all aspects falling within the scope and spirit of the appended claims.

EXAMPLES

Example 1: Collection of Blood and Sample Preparation

Six ABO-matched whole blood units are collected, pooled, and split into 6 samples in three pairs as provided in Table 2. Six units of whole blood (450 mL+10%) is collected in CPD and held on cooling trays until pathogen inactivation treatment. On the day of donation ($D_0$) these six whole blood units are pooled and split. Deoxygenation of whole blood is performed as described below. Units are treated provided with saline or riboflavin as indicated in Table 2. Samples 3 and 4 are oxygen reduced after pathogen treatment and component separation and preparation of packed red blood cells. Samples 5 and 6 are oxygen reduced at the whole blood stage and pathogen reduced prior to component separation and preparation of packed red blood cells. Riboflavin containing units are transferred to a MIRASOL® whole blood illumination bag and all the units placed on a cooling tray. Within 24 hours of donation, whole blood units are processed by the buffy coat method and red cell concentrates stored after addition of SAGM additive solution. Oxygen reduced red blood cell concentrates are prepared as described in Example 2.

TABLE 2

Samples for Pathogen Reduction with Riboflavin Photosensitiser

| Treatment | Sample 1 | Sample 2 | Sample 3 | Sample 4 | Sample 5 | Sample 6 |
|---|---|---|---|---|---|---|
| Oxygen reduced | No | No | RBCs | RBCs | Whole Blood | Whole Blood |
| Riboflavin (50 µM final) | No | 35 ml | No | 35 ml | No | 35 ml |
| Sterile Saline | 35 ml | No | 35 ml | No | 35 ml | No |
| O₂ removed prior to Pathogen reduction | n/a | No | n/a | No | n/a | Yes |

Example 2: Collection, Leukoreduction and Gas Depletion of Whole Blood

Pooled and split red blood cell units ("Blood units") in CPD are leukoreduced according to manufacturer's instructions after Mirasol treatment and component separation.

Each whole blood unit (sample 5 and 6) is processed for oxygen depletion by transferring to a whole blood in collection bag connected to an Sorin D100 membrane oxygenator and at a flow rate of 700 ml/minute with a mixture of 95% $N_2$ and 5% $CO_2$ gas to achieve pre-storage % SO2 of less than 3% and $pCO_2$ of 70 mmHg (37° C.). For Sample 6, $O_2$ from Mirasol® disposables (not including the riboflavin solution) are purged of oxygen prior to processing Immediately following the preparation of each sample, ABL90 blood gas levels are determined according to manufacturer's instructions to establish baseline $SO_2$ and $pCO_2$ levels (e.g., $T_0$). For Sample 6, oxygen-reduced blood is then transferred to the Mirasol treatment bag. After adding riboflavin, it is placed in the Mirasol photosensitizing device and exposed to UV according to manufacturer's instructions. After Mirasol treatment (Sample 6), the content is transferred back into original blood collection bag then component processed according to the standard top-bottom buffy coat method. Separated RBCs are leukoreduced with attached leukoreduction filter and stored in an anaerobic canister. For Sample 5, the Mirasol treatment steps are skipped from above.

For Samples 3 and 4, a separated and leukoreduced. RBC bag is connected to an Sorin D100 membrane oxygenator and at a flow rate of 700 ml/minute with a mixture of 95% $N_2$ and 5% $CO_2$ gas to achieve pre-storage % SO2 of less than 3% and $pCO_2$ of 70 mmHg (37° C.) Immediately following the preparation of each sample, ABL90 blood gas levels are determined according to manufacturer's instructions to establish baseline $SO_2$ and $pCO_2$ levels (e.g., $T_0$). O2-reduced RBC are transferred back into the original RBC storage bag and stored in anaerobic canister.

Example 3: Mirasol® Pathogen Reduction

Samples are processed using the Mirasol Illuminator according to manufacturer's instructions. The experiment is replicated five times for a total of n=5 samples at each data point.

Example 4: Storage of Anaerobic Test Products

Oxygen reduced and oxygen and carbon dioxide reduced blood in transfer bags are wrapped in mesh, secured with elastic and placed in anaerobic canisters with 4 sorbent sachets (Mitsubishi, SS-300). Canisters are sealed and the canister purged of air using nitrogen gas. Anaerobic and aerobic blood is placed in a Blood Bank refrigerator at 1 to 6° C. Canister gauges are monitored daily to ensure that they read 5±1 psi. Canisters that fall below 2 psi are adjusted.

Example 5: Sample Analysis

At days 2, 7, 14, 21, 28, and 42, the following measurements are performed from each of the six samples prepared according to the Examples above. The experiment is replicated five times for a total of n=5 samples at each data point.

a. Sample Preparation

These methods are known to those of skill in the art. Red blood cell-supernatant is prepared for microvesicle MV counts using the procedure of Schubert et al. (Schubert, et al., "Whole blood treated with riboflavin and ultraviolet light: Quality assessment of all blood components produced by the buffy coat method," Transfusion 55(4):815-823 (2015)). Red blood cell count, the mean corpuscle volume (MCV) and total hemoglobin in the individual samples are determined in a hematology analyzer (ADVIA 120, Siemens). Haematocrit is determined using the HAEMATOKRIT 210 device from Hettrich Zentrifugen according to the manufacturers' instructions. Metabolites (glucose and lactate) and potassium ($K^+$) are quantified using a Gem Premier 3000 blood gas analyzer (Instrumentation Laboratories). pH is measured with an Orion Ross Ultra Semi-Micro pH probe (Thermo Scientific). After day 1 measurements, hemoglobin and blood gas status is determined using Gem Premier 3000 blood gas analyzer (Instrumentation Laboratories) (% SO2, pCO2, pH, glucose, % Hb-O2, % Hb-CO, % met-Hb, % Hb). The degree of hemolysis is determined by the Harboe method of Han et. al, (2010) Vox Sang; 98:116-23). The level of ATP in red cells is quantified by HPLC after perchloric acid extraction of the red cells. Bacterial testing is performed at day 42 using the BacT/ALERT system (bioMérieux).

Figure 4:
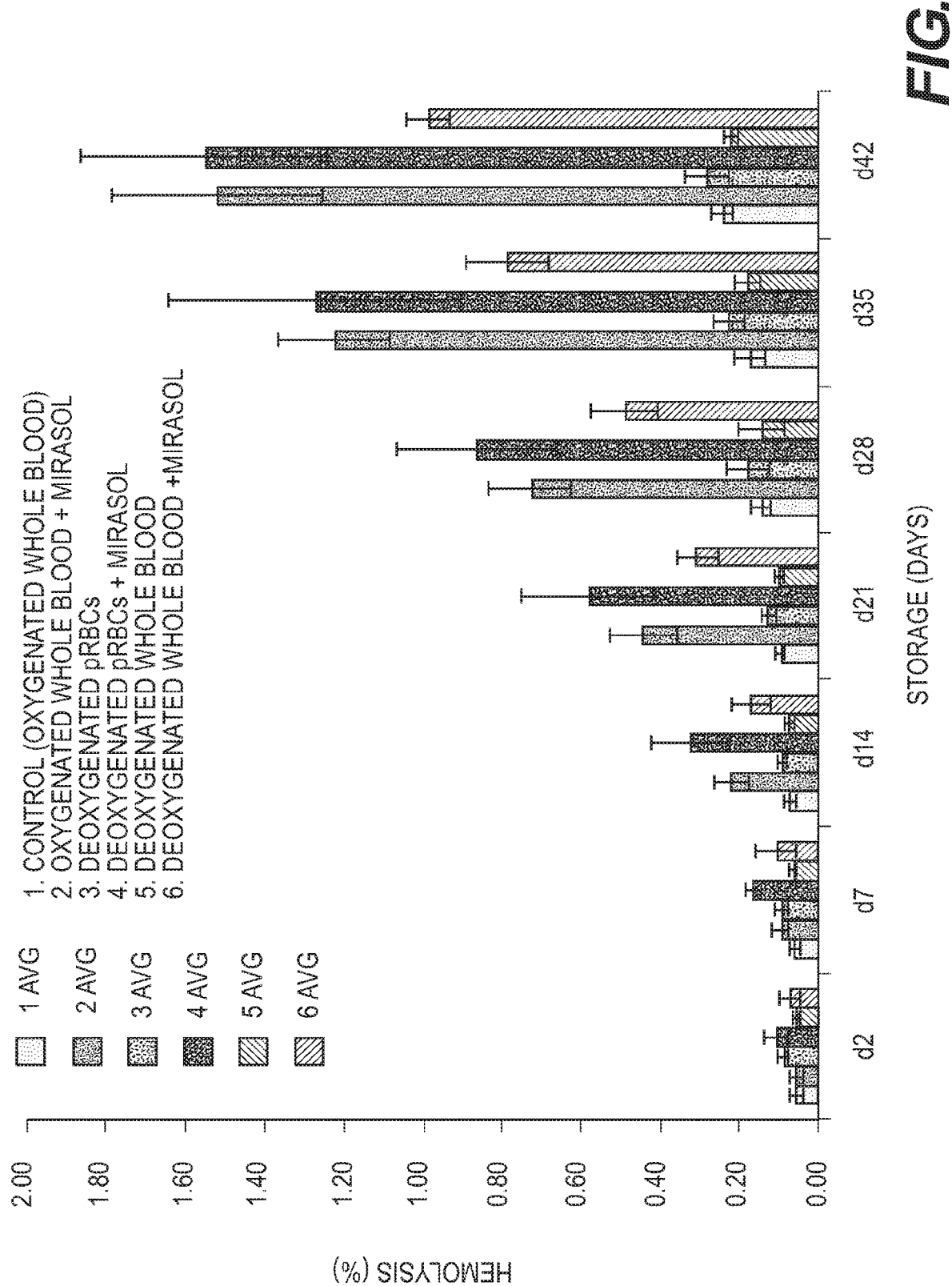
FIG. 4 is a graph presenting the results of an experiment according to the present disclosure, comparing the average hemolysis of control whole blood with sterile saline (1 avg), control whole blood with riboflavin (2 avg), oxygen reduced packed RBCs with sterile saline (3 avg), oxygen reduced pRBCs with riboflavin (4 avg), oxygen reduced whole blood with sterile saline (5 avg), and oxygen reduced whole blood with riboflavin (6 avg).

The results of a hemolysis analyses is presented in 4. As shown in FIG. 4, oxygen reduction prior to pathogen reduction greatly reduces hemolysis at all time points. The improvement to the storability of the red blood cells become evident beginning at day 14, though improvements are seen at earlier times.

Figure 5:
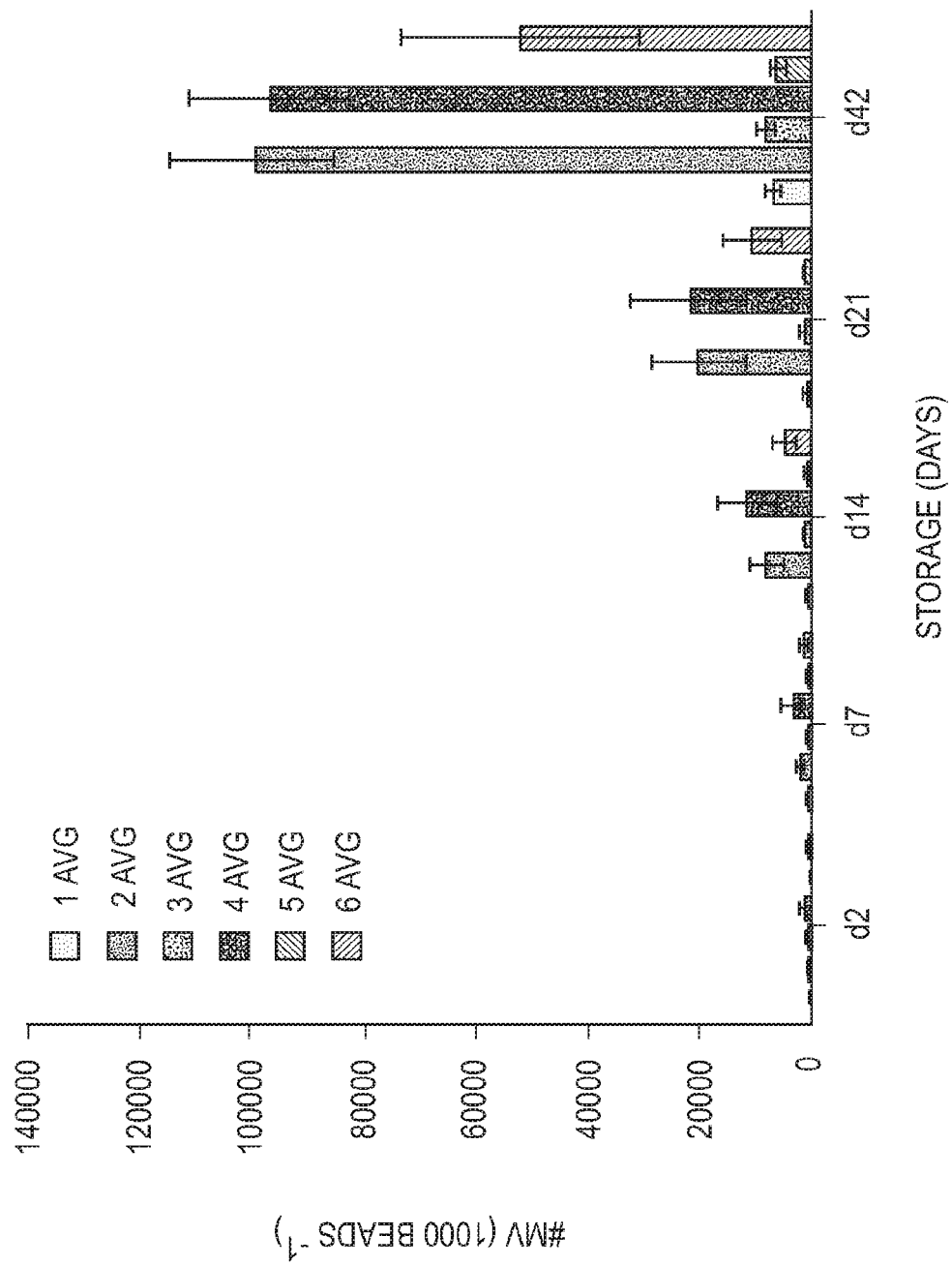
FIG. 5 is a graph presenting the results of an experiment according to the present disclosure, comparing the average amount of microparticles of control whole blood with sterile saline (1 avg), control whole blood with riboflavin (2 avg), oxygen reduced packed RBCs with sterile saline (3 avg), oxygen reduced pRBCs with riboflavin (4 avg), oxygen reduced whole blood with sterile saline (5 avg), and oxygen reduced whole blood with riboflavin (6 avg).
Figure 6A:
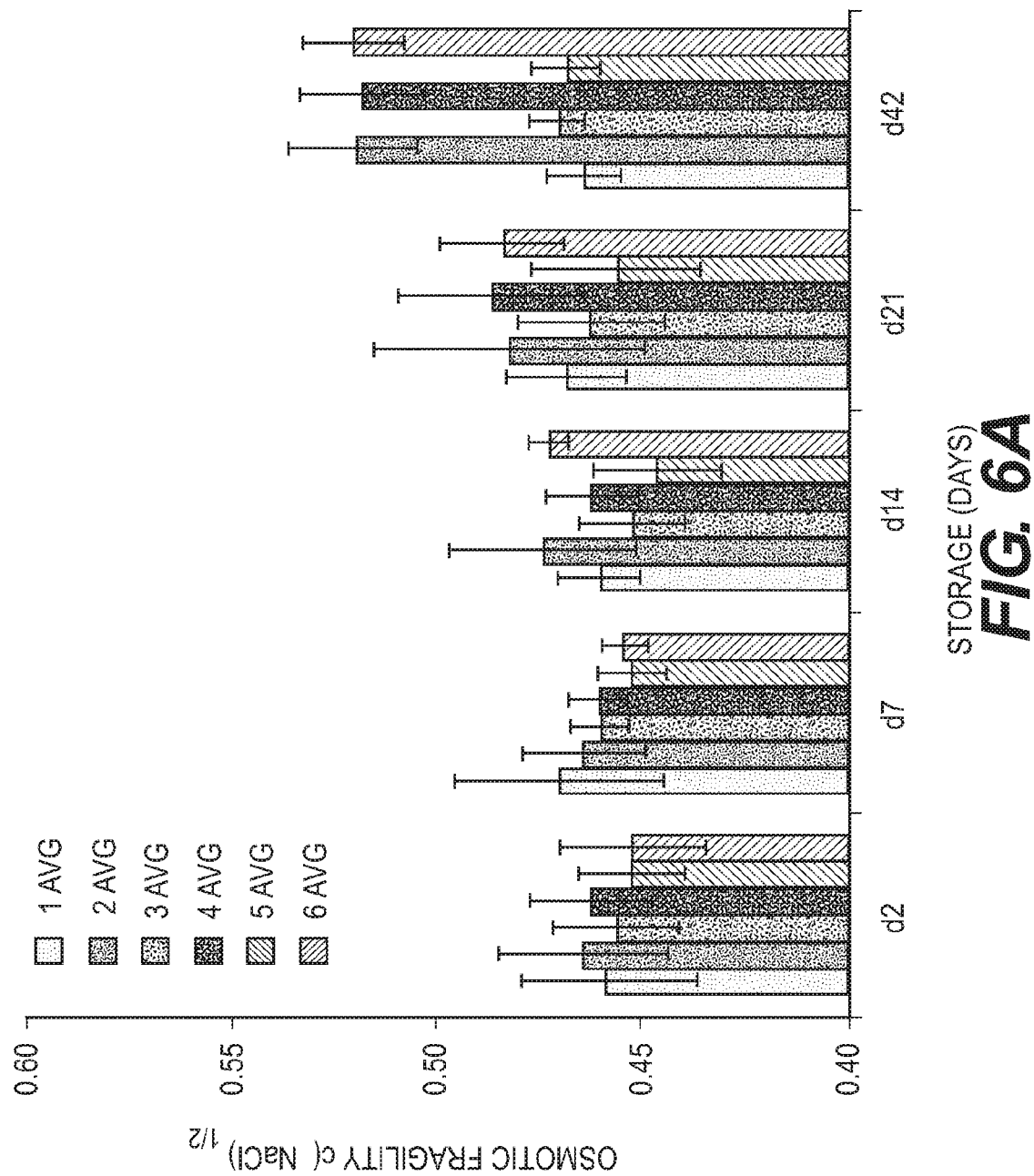
Figure 6B:
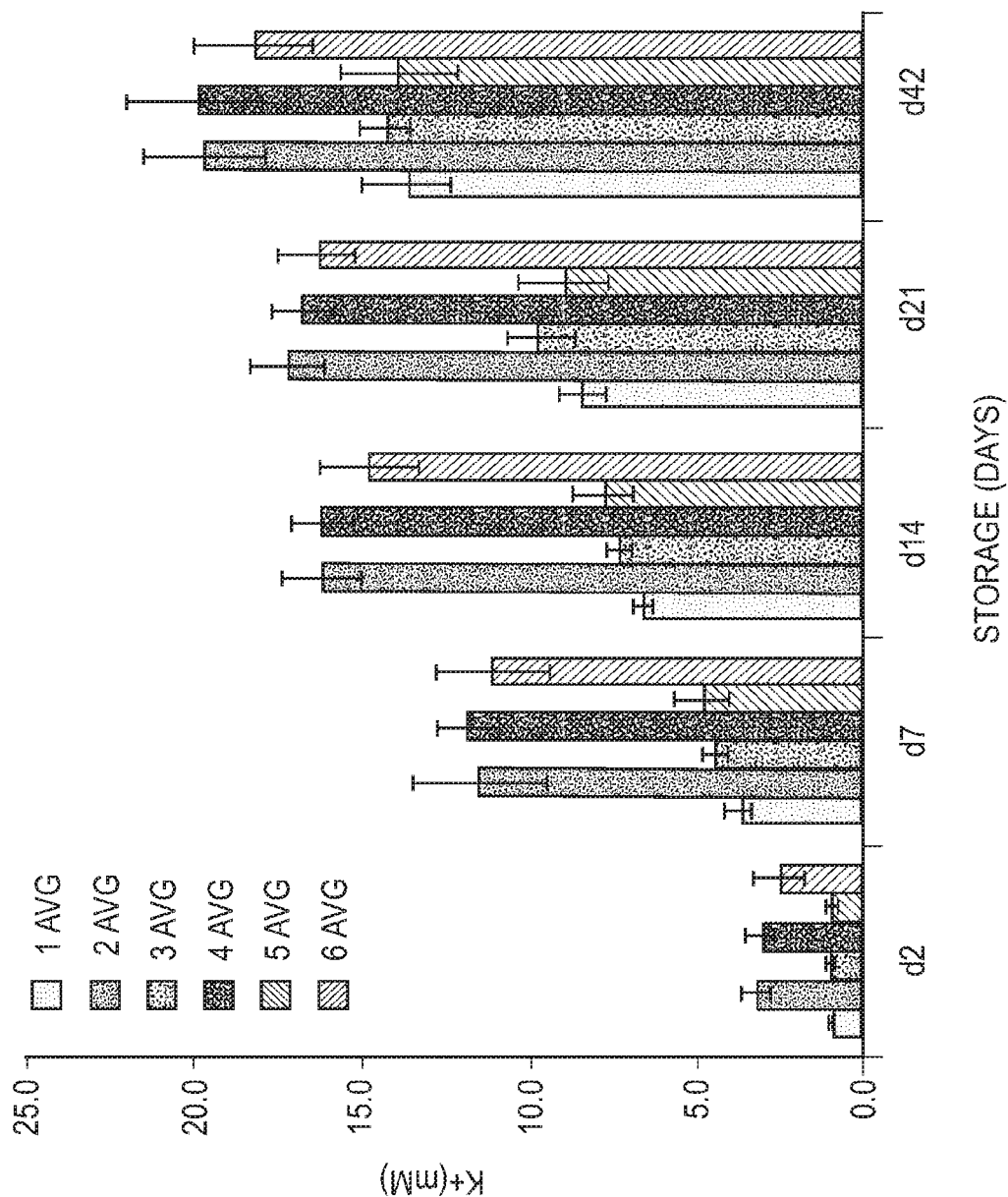
Figure 6D:
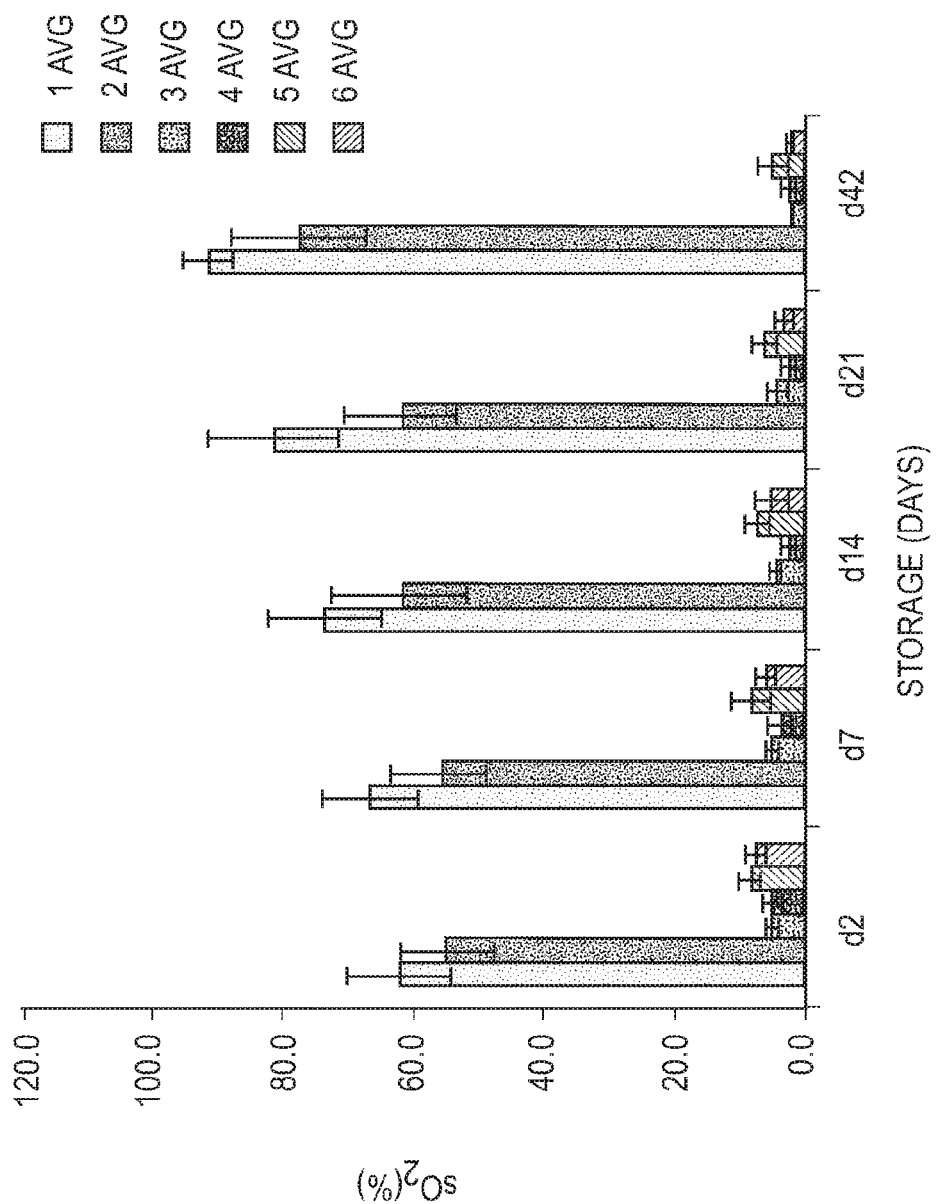
Figure 6E:
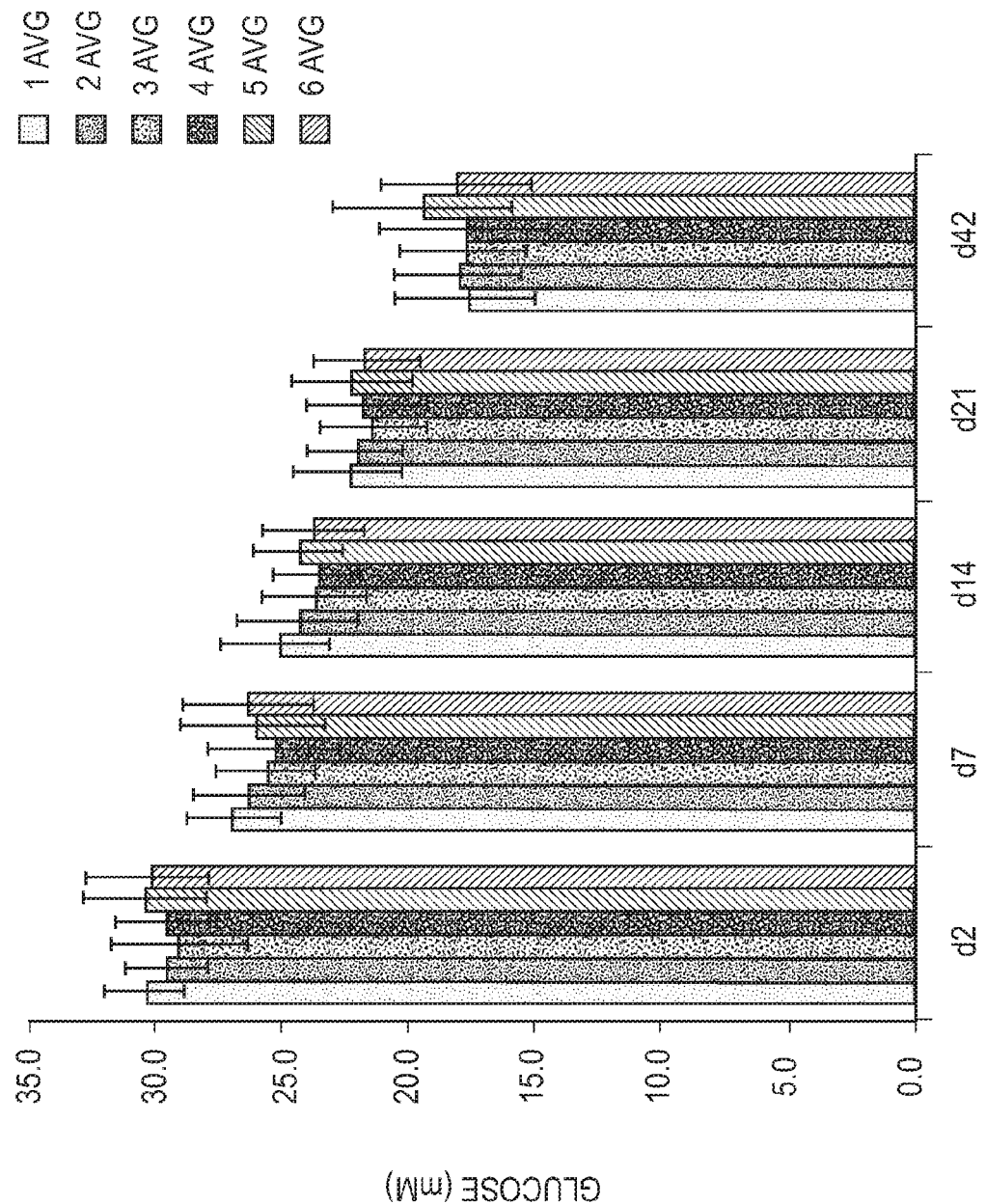
Figure 6F:
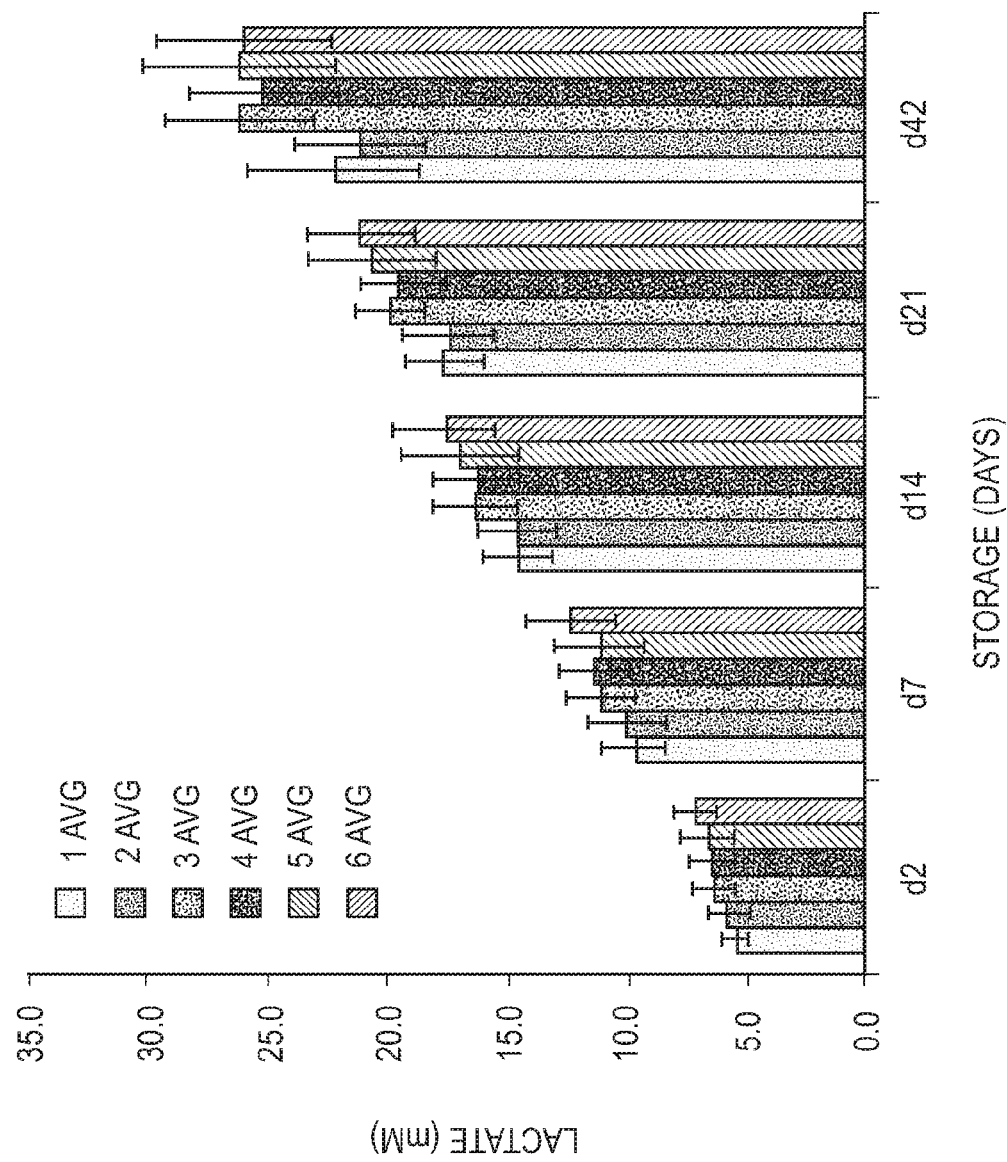
Figure 6G:
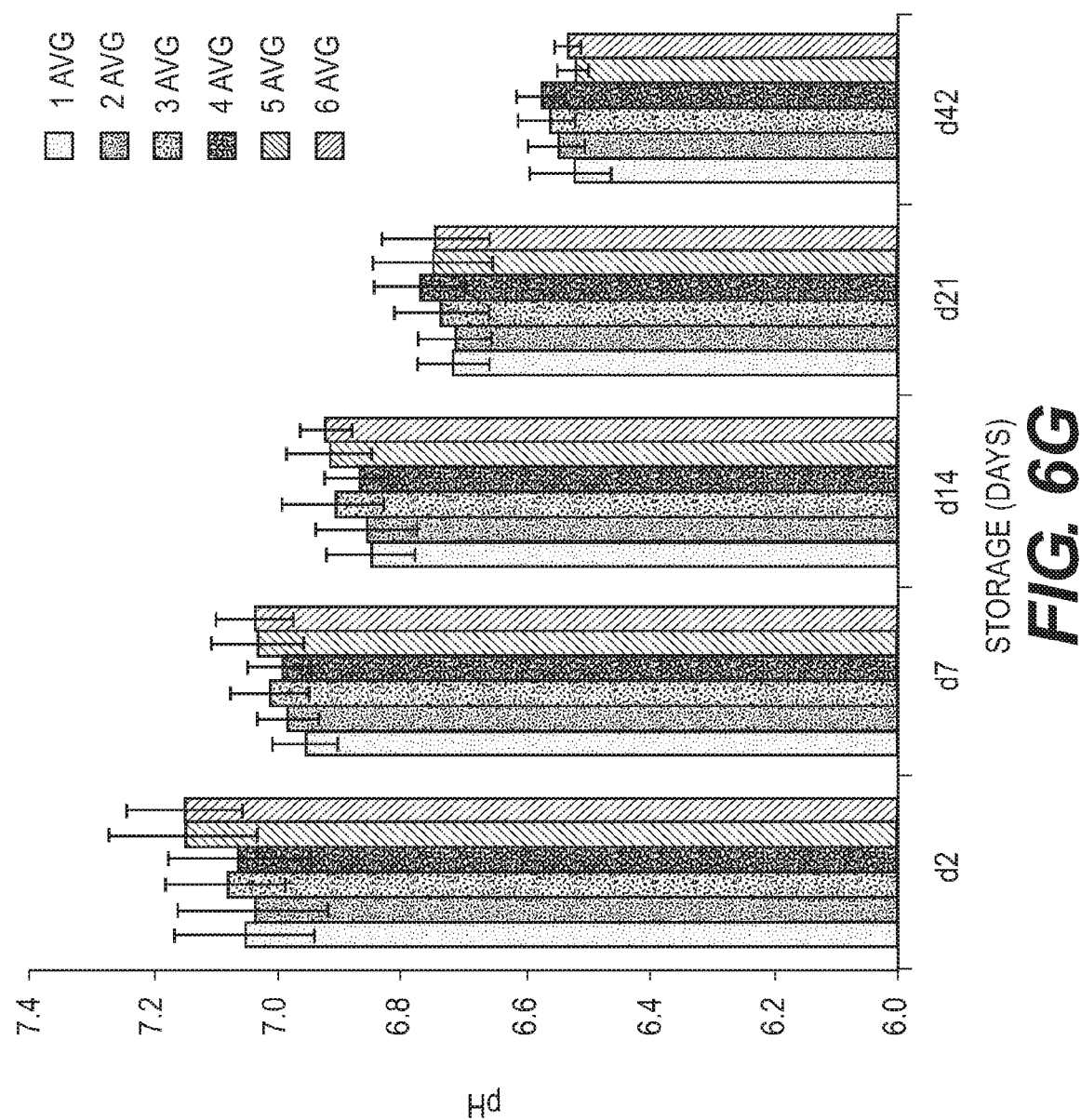

The results of a microparticle analysis showing the relative reduction in microparticle is presented in FIG. 5. As shown in FIG. 5, oxygen reduction prior to pathogen reduction greatly reduces the formation of microparticles at all time points. The improvement to the storability of the red blood cells become evident beginning at day 14, though improvements are seen at earlier times.

The results of osmotic fragility (6A), potassium (6B), total hemoglobin (6C), oxygen saturation (6D), glucose (6E), lactate (6F) and pH (6G) of control whole blood with sterile saline (1 avg), control whole blood with riboflavin (2 avg), oxygen reduced packed RBCs with sterile saline (3 avg), oxygen reduced pRBCs with riboflavin (4 avg), oxygen reduced whole blood with sterile saline (5 avg), and oxygen reduced whole blood with riboflavin (6 avg).

Example 6: Pathogen Inactivation Methods for Oxygen Reduced Blood

A sample of blood to be treated for pathogen inactivation is first processed for oxygen depletion by transferring to a whole blood collection bag connected to a Sorin D100 membrane oxygenator (Sorin Group, Arvada, CO) and pumped at a flow rate of 700 ml/minute with a mixture of 95% N2 and 5% CO2 gas to achieve pre-processing % SO2 of less than 25% and pCO2 of about 70 mmHg at about 23° C. For a desired blood component of whole blood with anticoagulant (WB), a volume of 500+/−50 mL is used; for a desired blood component of leukoreduced packed red blood cells with additive solution (LRpRBC), a volume of 500+/−50 mL is used; for desired blood component of suspended platelets (PLT), samples are combined for a total volume of about 400+/−50 mL; for a desired blood component of plasma, two units of about 200 mL each are combined for a volume of 400+/−50 mL. The blood sample is transferred into a polyvinyl chloride illumination bag (Terumo BCT, Lakewood, CO) and the bag is infused and mixed with the calculated dose of crosslinking agent. The illumination bag is then placed on a tray and illuminated with the appropriate illumination source according to the crosslinking agent, and the duration of illumination is calculated according to the dose required for the given volume and dose required for the given cross linking agent, according to the table. The tray is gently agitated during illumination to provide uniform exposure of the contents to the illumination source during the exposure period. Upon completion of the illumination cycle the blood sample is transferred from the illumination bag into an anaerobic storage bag for refrigerated storage. A whole blood sample may be further processed by centrifugation and separation into the separate blood components. Pathogen inactivation methods suitable for the methods of the present specification include the methods presented in Table 1

Example 7: Apheresis Collection and UV Treatment of Blood Components

A blood donor is accessed with venous puncture using a 17 gauge hypodermic needle and connected to an apheresis system. About 450 mL of whole blood (WB) is aspirated from the donor into the apheresis system and mixed with anticoagulant before centrifugation and separation of the blood components. The separated red blood cells (RBC's) are then mixed with additive solution and riboflavin, followed by passage through a UV illumination chamber and irradiation with UV light to inactivate pathogens and also inactivate any residual leukocytes. After UV irradiation, the RBC's are collected in a separate storage bag. The separated PLT's are then mixed with PLT additive solution and riboflavin, followed by passage through a UV illumination chamber and irradiation with UV light to inactivate pathogens. After UV irradiation, the PLT's are collected in a separate storage bag. The separated plasma is then mixed with riboflavin, followed by passage through a UV illumination chamber and irradiation with UV light to inactivate pathogens. After UV irradiation, the plasma is collected in a separate storage bag. A replacement fluid volume of 0.9% saline and crystalloid is returned to the donor before removal of the phlebotomy needle.

Example 8: Apheresis Collection and Uv Treatment of Whole Blood

A blood donor is accessed with venous puncture using a 17 gauge hypodermic needle and connected to an apheresis system. About 450 mL whole blood (WB) is aspirated from the donor into the apheresis system and mixed with anticoagulant and riboflavin before passage through an irradiation chamber and irradiation with UV light to inactivate pathogens, followed by centrifugation and separation of the blood components. After centrifugation and separation of the blood components, the RBC's are mixed with additive solution and collected in a separate storage bag. The separated PLT's are then mixed with PLT additive solution collected in a separate storage bag. The separated plasma is collected in a separate storage bag. A replacement fluid volume of 0.9% saline and crystalloid is returned to the donor before removal of the phlebotomy needle.

Example 9: Examining the Quality of Pathogen Inactivation (S-303) Treated RBC Five units of leukoreduced packed red blood cells with additive solution (e.g. AS3) (LRpRBC) are measured for complete blood counts (CBC) and percent oxygen saturation (% SO2). The five units are pooled together into a 2-3 liter blood bag to create a homogenous pool. The CBC and % SO2 is determined for the pooled LRpRBCs. Equal aliquots of 300 mL LRpRBC are placed into 5 storage containers, labelled A through E, treated as outlined in Table 3, and stored inside a standard blood bank refrigerator at 4° C. for 42 days.

Using the methods described in Example 5, aliquots of samples A to E are collected on days 0 (prior to storage), 7, 14, 21, and 42, and tested for the following parameters: CBC, percent hemolysis, ATP, 2,3-DPG, deformability using the MVA, microparticles, Phosphatidylserine (PS) exposure on red cell membrane, % SO2, RBC morphology, and RBC aggregation. The concentration of S-303 and S-300 is determined from aliquots of samples A to E collected at 0, 3, 6, 9, 12, and 24 hrs. The experiment is replicated five times for a total of n=5 samples at each data point.

The central trend in the data is measured using the mean and median values and the spread of the data is determined with the standard deviation.

TABLE 3

| Treatment Conditions of LRpRBC | |
|---|---|
| SAMPLE | TREATMENT CONDITION |
| A | Unprocessed control followed by conventional storage at 4° C. for 42 days |
| B | Pathogen inactivation followed by conventional storage at 4° C. for 42 days |
| C | Pathogen inactivation followed by oxygen reduction in Oxygen-Reduction Bag (ORB) |
| D | Oxygen reduction of RBC followed by pathogen inactivation |
| E | Conduct overnight pathogen inactivation inside ORB |

Example 10: Examining the Efficacy of S-303 Pathogen Inactivation Under Anaerobic Conditions Five units of leukoreduced packed red blood cells (LR-pRBC) with AS3 additive solution are measured for complete blood counts (CBC) and percent oxygen saturation (% SO2). The five units are pooled together into a 2-3 liter blood bag to create a homogenous pool. The CBC and % SO2 is determined for the pooled LRpRBCs. The pooled blood is spiked with a selected pathogen or model virus according to manufacturer's instructions. Equal aliquots of 300 mL LRpRBC are placed into 5 storage containers, labelled A through E, treated as outlined in Table 3. Sample B is treated with approximately 0.2 mM S-303 and approximately 2-20 mM glutathione (GSH) under aerobic conditions. Samples C and D are treated with approximately 0.2 mM S-303 and approximately 2-20 mM GSH, prior to and post oxygen reduction, respectively. Sample E is treated with approximately 0.2 mM S-303 and approximately 2-20 mM GSH overnight in an ORB. Following the outlined treatment, all samples are stored inside a standard blood bank refrigerator at 4° C. for 42 days. Alternatively, residual amount of S-300 in the samples is removed by centrifugation and replacement of fresh AS3.

Using the methods described in Example 5, aliquots of samples A to E are collected on days 0 (prior to storage), 7, 14, 21, and 42, and tested for the following parameters: CBC, concentration of residual pathogen, percent hemolysis, ATP, 2,3-DPG, deformability using the MVA, microparticles, Phosphatidylserine (PS) exposure on red cell membrane, and % SO2. The concentration of S-303 and S-300 is determined from aliquots of samples A to E collected at 0, 3, 6, 9, 12, and 24 hrs. The experiment is replicated five times for a total of n=5 samples at each data point.

The central trend in the data is measured using the mean and median values and the spread of the data is determined with the standard deviation. Differences between the various sample conditions are analyzed with the repeated measures of analysis of variance with Neuman-Keuls multiple comparison test and the probability level of less than 0.05 is considered significant.

The invention claimed is:

1. A method for reducing microparticle formation in a whole blood product comprising:
    reducing oxygen from whole blood to prepare an oxygen reduced whole blood product having an oxygen saturation (SO2) of less than 25%;
    reducing blood pathogens from the oxygen reduced whole blood product comprising:
        adding riboflavin to a concentration of between 40 and 60 micromolar (μM); and
        irradiating the riboflavin containing whole blood product with UV light between 265 and 400 nanometers (nm), thereby obtaining an oxygen reduced pathogen reduced whole blood product,
        wherein said microparticles are reduced by between 20 and 60% relative to a whole blood product from which blood pathogens are reduced and oxygen is not reduced.

2. The method of claim 1, further comprising storing the oxygen reduced pathogen reduced whole blood product under oxygen reduced conditions to maintain an SO2 of less than 25% in the oxygen reduced pathogen reduced whole blood product during storage.

3. The method of claim 1, further comprising reducing carbon dioxide from the oxygen reduced whole blood product to a partial pressure of carbon dioxide (pCO2) of 90 millimeters of mercury (mmHg) or less at 37° C.

4. The method of claim 3, further comprising storing the oxygen reduced pathogen reduced whole blood product under oxygen and carbon dioxide reduced conditions to maintain an SO2 of less than 25% and a pCO2 of 90 mmHg or less at 37° C. in the oxygen reduced pathogen reduced whole blood product during storage.

5. The method of claim 1, wherein the number of microparticles are reduced by at least 5 fold at 14 days, reduced by at least 5 fold at 21 days, or reduced by at least 5 fold at 42 days relative to a whole blood product from which blood pathogens are reduced and oxygen is not reduced.

6. The method of claim 1, wherein the riboflavin concentration is about 50 μM.

7. The method of claim 1, wherein the whole blood product is collected citrate phosphate dextrose (CPD), citrate phosphate double dextrose (CP2D), or citrate phosphate dextrose adenine (CPDA1).

8. The method of claim 1, wherein the oxygen reduced pathogen reduced whole blood product is leukoreduced, oxygen reduced and pathogen reduced whole blood.

\* \* \* \* \*